(12) United States Patent
Murphy et al.

(10) Patent No.: US 12,364,704 B2
(45) Date of Patent: Jul. 22, 2025

(54) FOSPROPOFOL SALTS, METHODS AND COMPOSITIONS

(71) Applicant: Epalex Corporation, Mountain View, CA (US)

(72) Inventors: Randall B. Murphy, Mountain View, CA (US); Steven L. Krill, San Clemente, CA (US); Samuel Andrew, Cambridge (GB)

(73) Assignee: EPALEX CORPORATION, Mountain View, CA (US)

( * ) Notice: Subject to any disclaimer, the term of this patent is extended or adjusted under 35 U.S.C. 154(b) by 5 days.

(21) Appl. No.: 18/062,683

(22) Filed: Dec. 7, 2022

(65) Prior Publication Data

US 2023/0172952 A1    Jun. 8, 2023

Related U.S. Application Data

(62) Division of application No. 17/168,365, filed on Feb. 5, 2021, now Pat. No. 11,547,714.

(60) Provisional application No. 62/970,324, filed on Feb. 5, 2020.

(51) Int. Cl.
 *A61K 31/661* (2006.01)
 *A61P 25/06* (2006.01)

(52) U.S. Cl.
 CPC ............ *A61K 31/661* (2013.01); *A61P 25/06* (2018.01); *C07B 2200/13* (2013.01)

(58) Field of Classification Search
 CPC .................................................. A61K 31/661
 See application file for complete search history.

(56) References Cited

U.S. PATENT DOCUMENTS

| | | | |
|---|---|---|---|
| 6,383,471 B1 | 5/2002 | Chen et al. | |
| 7,230,003 B2 | 6/2007 | Gallop et al. | |
| 7,241,807 B2 | 7/2007 | Xu et al. | |
| 7,538,092 B2 | 5/2009 | Orlando et al. | |
| 7,550,155 B2 | 6/2009 | Zhang et al. | |
| 7,645,792 B2 | 1/2010 | Xu et al. | |
| 8,354,454 B2 | 1/2013 | Mills et al. | |
| 8,383,687 B2 | 2/2013 | Harris et al. | |
| 8,470,861 B2 | 6/2013 | Anders et al. | |
| 8,541,400 B2 | 9/2013 | Johnsson et al. | |
| 8,962,696 B2 | 2/2015 | Harris et al. | |
| 9,023,813 B2 | 5/2015 | Shull | |
| 9,272,978 B2 | 3/2016 | Zhang et al. | |
| 9,339,553 B2 | 5/2016 | Zhang et al. | |
| 9,556,156 B2 | 1/2017 | Dugar et al. | |
| 9,643,917 B2 | 5/2017 | Li et al. | |
| 9,757,334 B2 | 9/2017 | Lovell et al. | |
| 10,239,851 B2 | 3/2019 | Li et al. | |
| 10,568,834 B2 | 2/2020 | Garti et al. | |
| 11,207,334 B1 | 12/2021 | Krill et al. | |
| 11,628,178 B2 * | 4/2023 | Krill ..................... | A61K 31/661 514/130 |
| 2005/0004381 A1 | 1/2005 | Gallop et al. | |
| 2006/0205969 A1 | 9/2006 | Xu et al. | |
| 2007/0135390 A1 | 6/2007 | West et al. | |
| 2007/0202158 A1 | 8/2007 | Slusher et al. | |
| 2007/0259933 A1 | 11/2007 | Virsik et al. | |
| 2008/0161400 A1 | 7/2008 | Virsik et al. | |
| 2008/0214508 A1 | 9/2008 | Slusher et al. | |
| 2008/0306285 A1 | 12/2008 | Hale et al. | |
| 2009/0076141 A1 | 3/2009 | Virsik | |
| 2009/0156562 A1 | 6/2009 | Winch | |
| 2009/0221532 A1 | 9/2009 | Gibiansky et al. | |
| 2009/0286763 A1 | 11/2009 | Xu et al. | |
| 2010/0311698 A1 | 12/2010 | Patel et al. | |
| 2011/0269844 A1 | 11/2011 | LeDonne | |
| 2012/0289470 A1 | 11/2012 | Heit et al. | |
| 2012/0295866 A1 | 11/2012 | Shull et al. | |
| 2012/0316247 A1 | 12/2012 | Xie et al. | |
| 2019/0151458 A1 | 5/2019 | Ciufolini et al. | |
| 2019/0224123 A1 | 7/2019 | Theisinger et al. | |
| 2020/0289404 A1 | 9/2020 | Slusher et al. | |

FOREIGN PATENT DOCUMENTS

| | | | | |
|---|---|---|---|---|
| CN | 1698588 A | 11/2005 | | |
| CN | 101675917 A | 3/2010 | | |
| CN | 101675918 A | 3/2010 | | |
| CN | 102351895 A | 2/2012 | | |
| CN | 102382005 A | 3/2012 | | |
| CN | 103172658 | * 6/2013 | ........... | A61K 31/661 |
| CN | 103816542 A | 5/2014 | | |
| CN | 106138015 A | 11/2016 | | |
| WO | WO 2000/008033 A1 | 2/2000 | | |
| WO | WO 2000/048572 A1 | 8/2000 | | |
| WO | WO 2002/013810 A1 | 2/2002 | | |
| WO | WO 2003/057153 A2 | 7/2003 | | |
| WO | WO 2003/086413 A1 | 10/2003 | | |
| WO | WO 2004/030658 A1 | 4/2004 | | |
| WO | WO 2004/032971 A1 | 4/2004 | | |
| WO | WO 2005/044201 A2 | 5/2005 | | |

(Continued)

OTHER PUBLICATIONS

Soleimanpour, International Journal of Emergency Medicine 2012, 5:19.*
Bengalorkar, J Anaesthesiol Clin Pharmacol. Jan.-Mar. 2011; 27(1): 79-83.*
Singhal, Advanced Drug Delivery Reviews 56 (2004) 335-347.*
International Patent Application No. PCT/US2021/065225; Int'l Search Report and the Written Opinion; dated Mar. 15, 2022; 15 pages.
Abdelmalak et al.; "Fospropofol, A New Sedative Anesthetic, and Its Utility in the Perioperative Period"; Current Pharmaceutical Design; vol. 18; 2012; p. 6241-6252.
Meek et al.; "Comparing propofol with placebo for early resolution of acute migraine in adult emergency department patients: A double-blind randomised controlled trial"; Emergency Medicine Australasia; 2020; 8 pages.
Mitra et al.; "Propofol for migraine in the emergency department: A pilot randomised controlled trial"; Emergency Medicine Australasia; vol. 32; 2020; p. 542-547.

(Continued)

*Primary Examiner* — Nizal S Chandrakumar
(74) *Attorney, Agent, or Firm* — BakerHostetler

(57) ABSTRACT

The present disclosure pertains to pharmaceutically acceptable salts of fospropofol and their use to treat migraine.

3 Claims, 43 Drawing Sheets

(56) References Cited

FOREIGN PATENT DOCUMENTS

| WO | WO 2006/017351 A1 | | 2/2006 | | |
|---|---|---|---|---|---|
| WO | WO 2006033911 | * | 3/2006 | ............... | A61K 9/00 |
| WO | WO-2006033911 A2 | * | 3/2006 | ............ | A61K 31/66 |
| WO | WO 2008/157627 A1 | | 12/2008 | | |
| WO | WO 2009/016269 A1 | | 2/2009 | | |
| WO | WO 2011/160267 A1 | | 12/2011 | | |
| WO | WO 2011/160268 A1 | | 12/2011 | | |
| WO | WO 2013/093931 A2 | | 6/2013 | | |
| WO | WO 2017/205632 A1 | | 11/2017 | | |

OTHER PUBLICATIONS

Piatka et al.; "Propofol for Treatment of Acute Migraine in the Emergency Department: A Systematic Review"; Academic Emergency Medicine; 2019; 13 pages.
Wei et al.; "Oral Delivery of Propofol with Methoxymethylphosphonic Acid as the Delivery Vehicle"; Journal of Medicinal Chemistry; vol. 60; 2017; p. 8580-8590.
Supplemental Tables S1 and S2 from Wozniak et al.; "Gastrointestinal delivery of propofol from fospropofol: its bioavailability and activity in rodents and human volunteers"; Journal of Translational Medicine; vol. 13; 2015; 3 pages.
Ahmad et al.; "Interactions between opioid drugs and propofol in laboratory models of seizures"; British Journal of Anaesthesia; vol. 74; 1995; p. 311-314.
Alessandri et al.; "Seizures and Sepsis: A Narrative Review"; Journal of Clinical Medicine; vol. 10; 2021; 10 pages.
Al-Hader et al.; "The Comparative Effects of Propofol, Thiopental, and Diazepam, Administered Intravenously, on Pentylenetetrazol Seizure Threshold in The Rabbit"; Life Sciences; vol. 51; 1992; p. 779-786.
"The American Headache Society Position Statement On Integrating New Migraine Treatments Into Clinical Practice"; Headache; vol. 59; 2019; 18 pages.
Bauman et al.; "Seizure Clusters: Morbidity and Mortality"; Frontier in Neurology; vol. 12; Feb. 2021; 5 pages.
Baumgartner et al.; "A survey of the European Reference Network EpiCARE on clinical practice for selected rare epilepsies"; Epilepsia Open; vol. 6; 2021; p. 160-470.
Beghi; "Addressing the burden of epilepsy: Many unmet needs"; Pharmacological Research; vol. 107; 2016; p. 79-84.
Beghi; "The Epidemiology of Epilepsy"; Neuroepidemiology; vol. 54; 2020; p. 185-191.
Begley et al.; "The direct cost of epilepsy in the United States: A systematic review of estimates"; Epilepsia; vol. 56; 2015; p. 1376-1387.
Bengalorkar et al.; "Fospropofol: Clinical Pharmacology"; Journal of Anaesthesiology Clinical Pharmacoloy; vol. 27; 2011; p. 79-83.
Bialer et al.; "Progress report on new antiepileptic drugs: A summary of the Fifteenth Eilat Conference on New Antiepileptic Drugs and Devices (EILAT XV). I. Drugs in preclinical and early clinical development"; Epilepsia; vol. 61; 2020; p. 2340-2364.
Binnie et al.; "Acute effects of lamotrigine (BW430C) in persons with epilepsy"; Epilepsia; vol. 27; 1986; p. 248-254 (abstract only).
Binnie et al.; "Photosensitivity as a model for acute antiepileptic drug studies"; Electroencephalogr Clin Neurophysiol.; vol. 63; Jan. 1986; p. 35-41 (abstract only).
Binnie; "Preliminary evaluation of potential anti-epileptic drugs by single dose electrophysiological and pharmacological studies in patients"; J. Neural Transm.; vol. 72; 1988; p. 259-266 (abstract only).
Bonafede et al.; "Direct and Indirect Healthcare Resource Utilization and Costs Among Migraine Patients in the United States"; Headache; May 2018; p. 700-714.
Bond et al.; "The use of analogue scales in rating subjective feelings"; Br. J. Med. Psychol.; vol. 47; 1974; p. 211-218.

Borgdorff; "Arguments against the role of cortical spreading depression in migraine"; Neurological Research; vol. 40 No. 3; 2018; p. 173-181.
Brodie et al.; "Patterns of treatment response in newly diagnosed epilepsy"; Neurology; vol. 78; 2012; p. 1548-1554.
Brophy et al.; "Guidelines for the Evaluation and Management of Status Epilepticus"; Neurocrit Care; vol. 17; 2012; p. 3-23.
Burch et al.; "The Prevalence and Impact of Migraine and Severe Headache in the United States: Figures and Trends From Government Health Studies"; Headache; vol. 58; 2018; p. 496-505.
Cameron; "Opisthotonos again"; Anaesthesia; vol. 42; 1987; p. 1124.
"Summary Health Statistics: National Health Interview Survey"; https://ftp.cdc.gov/pub/Health_Statistics/NCHS/NHIS/SHS/2018_SHS_Table_A-5.pdf; U.S. Department of Health and Human Services; 2018; 9 pages.
Chernik et al.; "Validity and reliability of the Observer's Assessment of Alertness/Sedation Scale: study with Intravenous Midazolam"; Journal of Clinical Psychopharmacology; vol. 10 No. 4; 1990; p. 244-251.
"Clinical Brief—Examining the Economic Impact and Implications of Epilepsy"; The American Journal of Managed Care; Feb. 2020; 8 pages.
Cohen; "Clinical trial: a dose-response study of fospropofol disodium for moderate sedation during colonoscopy"; Alimentary Pharmacology & Therapeutics; vol. 27; 2008; p. 597-608.
Contreras et al.; "Bioavailability of Oral Propofol in Humans"; Int'l Society for Anaesthetic Pharmacology; 2011; p. 21-23 (abstracts).
Dalic et al.; "Managing drug-resistant epilepsy: challenges and solutions"; Neuropsychiatric Disease and Treatment; vol. 12; 2016; p. 2605-2616.
De Riu et al.; "Propofol Anticonvulsant Activity in Experimental Epileptic Status"; British Journal of Anaesthesia; vol. 69; 1992; p. 177-181.
Dinis-Oliveria; "Metabolic Profiles of Propofol and Fospropofol: Clinical and Forensic Interpretative Aspects"; BioMed Research Int'l; vol. 2018 Article 6852857; 2018; 16 pages.
Falco-Water; "Epilepsy—Definition, Classification, Pathophysiology, and Epidemiology"; Seminars in Neurology; vol. 40; 2020; p. 617-623.
Farzana et al.; "Parosmia and Dysgeusia after Intravenous Propofol-Based General Anesthesia: A Case Report"; Annals of Cardiac Anaesthesia; vol. 25; 2022; p. 112-115.
Feist et al.; "Prevalence and incidence of epilepsy"; Neurology; vol. 88; 2017; p. 296-303.
Fisher et al.; "Epileptic Seizures and Epilepsy: Definitions Proposed by the International League Against Epilepsy (ILAE) and the International Bureau for Epilepsy (IBE)"; Epilepsia; vol. 46 No. 4; 2005; p. 470-472.
Fisher et al.; "A practical clinical definition of epilepsy"; Epilepsia; vol. 55; 2014; p. 475-482.
Fodale et al.; "Propofol Infusion Syndrome An Overview of a Perplexing Disease"; Drug Safety; vol. 31; 2008; p. 293-303.
French et al.; "Efficacy and Tolerability of the New Antiepileptic Drugs, II: Treatment of Refractory Epilepsy: Report of the TTA and QSS Subcommittees of the American Academy of Neurology and the American Epilepsy Society"; Epilepsia; vol. 45; 2004; p. 410-423.
French et al.; "Inhaled alprazolam rapidly suppresses epileptic activity in photosensitive participants"; Epilepsia; vol. 60; 2019; p. 1602-1609.
French et al.; "Time to Start Calling Things by Their Own Names? The Case for Antiseizure Medicines"; Epilepsia Current; vol. 20; 2020; p. 69-72.
Gan et al.; "Determination of plasma concentrations of propofol associated with 50% reduction in postoperative nausea"; Anesthesiology; vol. 87; 1997; p. 779-784.
Garcia et al.; "General Anesthetic Actions on GABAA Receptors"; Current Neuropharmacology; vol. 8, 2010; p. 2-9.
"Global, regional, and national incidence, prevalence, and years lived with disability for 310 diseases and injuries, 1990-2015: a systematic analysis for the Global Burden of Disease Study 2015";

(56) References Cited

OTHER PUBLICATIONS

GBD 2015 Disease and Injury Incidence and Prevalence Collaborators; Lancet; vol. 388; Oct. 2016; p. 1545-1602.

"Global, regional, and national incidence, prevalence, and years lived with disability for 328 diseases and injuries for 195 countries, 1990-2016: a systematic analysis for the Global Burden of Disease Study 2016"; GBD 2016 Disease and Injury Incidence and Prevalence Collaborators; Lancet; vol. 390; Sep. 2017; p. 1211-1259.

"Global, regional, and national burden of epilepsy, 1990-2016: a systematic analysis for the Global Burden of Disease Study 2016"; GBD 2016 Epilepsy Collaborators; Lancet; vol. 18; Apr. 2019; p. 357-375.

"Global, regional, and national incidence, prevalence, and years lived with disability for 354 diseases and injuries for 195 countries and territories, 1990-2017: a systematic analysis for the Global Burden of Disease Study 2017"; GBD 2017 Disease and Injury Incidence and Prevalence Collaborators; Lancet; vol. 392; Nov. 2018; p. 1789-1858.

Hasan; "Evaluation of the Anticonvulsant Effects of Propofol in Pentylenetetrazole kindled Rats"; The FASEB Journal; vol. 31; 2017; p. 813.6 (abstract only).

Hasan et al.; "Comparison between the effects of propofol and midazolam on pentylenetetrazole kindled convulsions in rats"; The FASEB Journal; vol. 33; 2019; p. 665.4 (abstract only).

"Headache Classification Committee of the International Headache Society (IHS)"; The International Classification of Headache Disorders, 3rd edition; Cephalalgia; vol. 38; 2018; 211 pages.

Hiraoka et al.; "Changes in drug plasma concentrations of an extensively bound and highly extracted drug, propofol, in response to altered plasma binding"; Clinical Pharmacology & Therapeutics; vol. 75; 2004; p. 324-330.

Hiraoka et al.; "Kidneys contribute to the extrahepatic clearance of propofol in humans, but not lungs and brain"; British Journal of Clinical Pharmacology; vol. 60; 2005; p. 176-182.

Hoymork et al.; "Why do women wake up faster than men from propofol anaesthesia?"; British Journal of Anaesthesia; vol. 95; 2005; p. 627-633.

Johannessen et al.; "Therapeutic drug monitoring of antiepileptic drugs: current status and future prospects"; Expert Opinion on Drug Metabolism & Toxicology; vol. 16; 2020; p. 227-238.

Kasteleijn-Nolst et al.; "Photosensitive epilepsy: a model to study the effects of antiepileptic drugs. Evaluation of the piracetam analogue, levetiracetam"; Epilepsy Research; vol. 25; 1996; p. 225-230.

Kasteleijn-Nolst et al.; "Evaluation of brivaracetam, a novel SV2A ligand, in the photosensitivity model"; Neurology; vol. 69; 2007; p. 1027-1034.

Katsarava et al.; "Defining the Differences Between Episodic Migraine and Chronic Migraine"; Curr Pain Headache Rep; vol. 16; 2012; p. 86-92.

Kumar et al.; "Intraoperative refractory status epilepticus caused by propofol—a case report-"; Korean Journal of Anesthesiology; vol. 74; 2021; p. 70-72.

Lee et al.; "Diagnosis and Treatment of Status Epilepticus"; Journal of Epilepsy Research; vol. 10; 2020; p. 45-54.

Lingamaneni et al.; "Anesthetic Properties of 4-Iodopropofol"; Anesthesiology; vol. 94; Jun. 2001; p. 1050-1057.

Lipton et al.; "Migraine prevalence, disease burden, and the need for preventive therapy"; Neurology; vol. 68; 2007; p. 343-349.

Lipton et al.; "Predicting Inadequate Response to Acute Migraine Medication: Results From the American Migraine Prevalence and Prevention (AMPP) Study"; Headache; vol. 56; 2016; p. 1635-1648.

Lowson et al.; "Anticonvulsant Properties of Propofol and Thiopentone: Comparison Using Two Tests in Laboratory Mice"; British Journal of Anaesthesia; vol. 64; 1990; p. 59-63.

Lu et al.; "Propofol-induced refractory status epilepticus at remission age in benign epilepsy with centrotemporal spikes—A case report and literature review"; Medicine; vol. 98; 2019; 5 pages.

Mahmoud et al.; "Migraine and the risk of cardiovascular and cerebrovascular events: a metaanalysis of 16 cohort studies including 1 152 407 subjects"; BMJ Open; 2018; 10 pages.

Marmura et al.; "The Acute Treatment of Migraine in Adults: The American Headache Society Evidence Assessment of Migraine Pharmacotherapies"; Headache; vol. 55; 2015; p. 3-20.

Mathew et al.; "Intravenous Valproate Sodium (Depacon) Aborts Migraine Rapidly: A Preliminary Report"; Headache; vol. 40; 2000; p. 720-723.

Meyer et al.; "Propofol: Pro- or Anticonvulsant Drug?"; Int'l Anesthesia Research Society; vol. 108; Jun. 2009; p. 1993-1994.

Munakata et al.; "Economic Burden of Transformed Migraine: Results From the American Migraine Prevalence and Prevention (AMPP) Study"; Headache; vol. 49; 2009; p. 498-508.

Ngugi et al.; "Estimation of the burden of active and life-time epilepsy: A meta-analytic approach"; Epilepsia; vol. 51(5); 2010; p. 883-890.

Nicolodi et al.; "Exploration of NMDA Receptors in Migraine: Therapeutic and Theoretic Implications"; Int'l J. Clin. Pharm. Res; vol. 15; 1995; p. 181-189.

Nishikawa et al.; "Inhibitory Influence of GABA on Central Serotonergic Transmission. Involvement of the Habenulo-Raph6 Pathways in the GABAergic Inhibition of Ascending Cerebral Serotonergic Neurons"; Brain Research; vol. 331; 1985; p. 81-90.

Oei-Lim et al.; "Pharmacokinetics of propofol during conscious sedation using target-controlled infusion in anxious patients undergoing dental treatment"; British Journal of Anaesthesia; vol. 80; 1998; p. 324-331.

Ohmori et al.; "The Anticonvulsant Action of Propofol on Epileptiform Activity in Rat Hippocampal Slices"; Anesth Analg; vol. 99; 2004; p. 1095-1101.

Pack et al.; "Epilepsy Overview and Revised Classification of Seizures and Epilepsies"; Continuum Journal; vol. 25; Apr. 2019; p. 306-321.

Penovich; "Acute Repetitive Seizures (ARS) or Cluster Seizures"; https://www.epilepsyfoundationmn.org/2020/01/14/acute-repetitive-seizures-ars-or-cluster-seizures/; Jan. 2021; 4 pages.

Perucca et al.; "30 years of second-generation antiseizure medications: impact and future perspectives"; Lancet Neurology; vol. 19; 2020; 12 pages.

Puledda et al.; "Non-Pharmacological Approaches for Migraine"; Neurotheraputics; vol. 15; 2018; p. 336-345.

Puri G.D; "Target controlled infusion total intravenous anaesthesia and Indian patients: Do we need our own data?"; Indian Journal of Anaesthesia; vol. 62; 2018; p. 245-248.

Rampil; "A primer for EEG signal processing in anesthesia"; Anesthesiology; vol. 89; 1998; p. 980-1002.

Raoof et al.; "In vivo assessment of intestinal, hepatic, and pulmonary first pass metabolism of propofol in the rat"; Pharmaceutical Research; vol. 13; 1996; p. 891-895.

Rogawski, MD; "Common Pathophysiologic Mechanisms in Migraine and Epilepsy"; Arch Neurol; vol. 65 No. 6; Jun. 2008; p. 709-714.

Rohmann et al.; "Migraine, headache, and mortality in women: a cohort study"; The Journal of Headache and Pain; vol. 21:27; 2020; 8 pages.

Rui et al.; "National Hospital Ambulatory Medical Care Survey: 2017 Emergency Department Summary Tables"; CDC National Center for Health Statistics; https://www.cdc.gov/nchs/data/nhamcs/web_tables/2017_ed_web_tables-508.pdf; 2017; accessed Apr. 2020; 37 pages.

Sahinovic et al.; "Clinical Pharmacokinetics and Pharmacodynamics of Propofol"; Clin Pharmacokinet; vol. 57; 2018; p. 1539-1558.

Samra et al.; "Effects of propofol sedation on seizures and intracranially recorded epileptiform activity in patients with partial epilepsy"; Anesthesiology; vol. 82; 1995; p. 843-851.

Schwedt et al.; "Acute treatment of migraine in adults"; Wolters Kluwer; 2021; 36 pages.

Silberstein; "Practice parameter: evidence-based guidelines for migraine headache (an evidence-based review): report of the Quality Standards Subcommittee of the American Academy of Neurology"; Neurology; vol. 55; 2000; p. 754-762.

(56) References Cited

OTHER PUBLICATIONS

Silvestri et al.; "Fospropofol Disodium for Sedation in Elderly Patients Undergoing Flexible Bronchoscopy"; J Bronchology Interv Pulmonol.; vol. 18(1); Jan. 2011; p. 15-22.
Simon et al.; "Disposition and pharmacology of propofol glucuronide administered intravenously to animals"; Xenobiotica; vol. 22 No. 11; 1992; p. 1267-1273.
J. R. Sneyd; "Excitatory events associated with propofol anaesthesia: a review"; Journal of the Royal Society of Medicine; vol. 85; May 1992; p. 288-291.
Straube et al.; "Primary headaches during lifespan"; The Journal of Headache and Pain; vol. 20; 2019; 14 pages.
Strzelczyk et al.; "Expanding the Treatment Landscape for Lennox-Gastaut Syndrome: Current and Future Strategies"; CNS Drugs; vol. 35; 2021; p. 61-83.
"Summary Health Statistics: National Health Interview Survey, 2018"; U.S. Dept. of Health and Human Services; 2018; 9 pages.
Trapani et al.; "Propofol in Anesthesia. Mechanism of Action, Structure-Activity Relationships, and Drug Delivery"; Current Medicinal Chemistry; vol. 7; 2000; p. 249-271.
VanHaerents et al.; "Epilepsy Emergencies: Status Epilepticus, Acute Repetitive Seizures, and Autoimmune Encephalitis"; Continuum: Lifelong Learning in Neurology; vol. 25; 2019; p. 454-476.
Vasileiou et al.; "Propofol: A review of its non-anaesthetic effects"; European Journal of Pharmacology; vol. 605; 2009; 8 pages.
Vasquez et al.; "Pediatric refractory and super-refractory status epilepticus"; Seizure; vol. 68; 2019; p. 62-71.
Veselis et al.; "Low-dose Propofol-induced Amnesia Is Not due to a Failure of Encoding"; Anesthesiology; vol. 109; Aug. 2008; p. 213-224.
Wood et al.; "Propofol Infusion for the Treatment of Status Epilepticus"; The Lancet; Feb. 1988; p. 480-481.
"Epilepsy—A public health imperative"; World Health Organization; 2019; 171 pages.
H.F. Yanny; "Propofol infusions for status epilepticus"; Anaesthesia; vol. 43; 1988; p. 514.
Zack et al.; "National and State Estimates of the Nos. of Adults and Children with Active Epilepsy—United States, 2015"; Morbidity and Mortality Weekly Report; vol. 66 No. 31; Aug. 2017; p. 821-825.
Zhang et al.; "Systematic review and meta-analysis of propofol versus barbiturates for controlling refractory status epilepticus"; BMC Neurology; vol. 19; 2019; 11 pages.
Brodie; "Road to refractory epilepsy: The Glasgow story"; Epilepsia; vol. 54 Supplemental 2; 2013; p. 5-8.
Kasteleijin-Nolst Trenite; "Photosensitivity in epilepsy. Electrophysiological and clinical correlates"; Acta Neurol Scan Suppl.; vol. 125; 1989; p. 3-147.
Kasteleijin-Nolst Trenite et al.; "Preliminary assessment of the efficacy of Org 6370 in photosensitive epileptic patients: paradoxical enhancement of photosensitivity and provocation of myoclonic seizures"; Epilpsia; vol. 33(1); 1992; p. 135-141.
Kasteleijin-Nolst Trenite et al.; "Evaluation of carisbamate, a novel antiepileptic drug, in photosensitive patients: An exploratory, placebo-controlled study"; Epilepsy Research; vol. 74; 2007; p. 193-200.
Nishikawa et al.; "Inhibitory Influence of GABA on Central Serotonergic Transmission. Raphé Nuclei as the Neuroanatomical Site of the GABAergic Inhibition of Cerebral Serotonergic Neurons"; Brain Research; vol. 331; 1985; p. 91-103.
"Initial Investigational New Drug Application—(Fospropofol Disodium) For Oral Administration"; Investigator's Brochure; Version 1.0; Jul. 2020; 69 pages.
"US 21 CFR Part 58. Good Laboratory Practice for Nonclinical Laboratory Studies"; Available at https://www.ecfr.gov/cgi-bin/text-idx?SID=3be49f31878defa85f39ed3b84fcbe1&mc=true&node=se21.1.58_11&rgn=div8; 16 pages.
"Diprivan® (propofol) injectable emulsion, USP"; https://www.accessdata.fda.gov/drugsatfda_docs/label/2017/019627s066lbl.pdf; Fresenius-Kabi; Apr. 2017; 54 pages.
Sheehan et al.; "Comparative Validation of the S-STS, the ISSTPlus, and the C-SSRS for Assessing the Suicidal Thinking and Behavior FDA 2012 Suicidality Categories"; Innov Clin Neurosci.; vol. 11; 2014; p. 32-46.
Sheehan et al.; "Status Update on the Sheehan-Suicidality Tracking Scale (S-STS) 2014"; Innov Clin Neurosci.; vol. 11; 2014; p. 93-140.
"Bioanalytical Method Validation Guidance for Industry"; U.S. Dept. of Health and Human Services; May 2018; Biopharmaceutics; 41 pages.
"E6(R2) Good Clinical Practice: Integrated Addendum to ICH E6(R1) Guidance for Industry"; U.S. Dept. of Health and Human Services; Mar. 2018; 69 pages.
"Lusedra™ (fospropofol disodium) Injection, for intravenous use"; FDA printed label. Revised Oct. 2009. Available at https://www.accessdata.fda.gov/drugsatfda_docs/label/2010/022244s006lbl.pdf; 3 pages.
Aeschbacher et al.; "Propofol in rabbits. 2. Long-term anesthesia."; Laboratory Animal Science; vol. 43(4); Aug. 1993; p. 328-335 (abstract only).
Glen et al.; "Interaction Studies and other investigations of the pharmacology of propofol ('Diprivan')"; Postgrad Med J.; vol. 61 Suppl. 3; 1985; p. 7-14 (abstract only).
Muir et al.; "Respiratory depression and apnea induced by propofol in dogs"; Am J Vet Res.; vol. 59(2); Feb. 1998; p. 157-161 (abstract only).
"IHS Classification ICHD-3"; https://ichd-3.org/evolution-of-ihs-classification-1-3/; International Headache Society; © 2021; accessed Feb. 9, 2023; 3 pages.
U.S. Appl. No. 17/066,957, filed Oct. 9, 2020, Rogawski et al.
U.S. Appl. No. 17/387,059, filed Jul. 28, 2021, Krill et al.
U.S. Appl. No. 17/465,966, filed Sep. 3, 2021, Krill et al.
U.S. Appl. No. 17/466,016, filed Sep. 3, 2021, Krill et al.
U.S. Appl. No. 17/562,605, filed Dec. 27, 2021, Krill et al.
Feng et al., "Novel propofol derivatives and implications for anesthesia practice", J. Anaesthesiol Clin Pharmacol., Jan.-Mar. 2017; vol. 33(1), p. 9-15.
Dhir; "Propofol in the treatment of refractory migraine headaches"; Expert Review of Neurotherapeutics; vol. 16 No. 9; 2016; p. 1007-1011.
Harris et al.; "Monitored anesthesia care (MAC) sedation: clinical utility of fospropofol"; Therapeutics and Clinical Risk Management; vol. 5; 2009; p. 949-959.
Ovesen et al.; "Intraluminal pH in the Stomach, Duodenum, and Proximal Jejunum in Normal Subjects and Patients With Exocrine Pancreatic Insufficiency"; Gastroenterology; vol. 90; 1986; p. 958-962.
Wozniak et al.; "Gastrointestinal delivery of propofol from fospropofol: its bioavailability and activity in rodents and human volunteers"; Journal of Translational Medicine; vol. 13; 2015; 13 pages.
Wilson et al.; "The abuse potential of propofol"; Clinical Toxicology; vol. 48; 2010; p. 165-170.
Ward et al.; "Use of intravenous propofol in the treatment of migraine headache"; EMA; 2013; p. 619.
Soleimanpour et al.; "Improvement of refractory migraine headache by propofol: case series"; Int'l Journal of Emergency Medicine; vol. 5; 2012; 4 pages.
Soleimanpour et al.; "Effectiveness of intravenous Dexamethasone versus Propofol for pain relief in the migraine headache: A prospective double blind randomized clinical trial"; BMC Neurology; vol. 12; 2012; 7 pages.
Simmonds et al.; "The Effect of Single-Dose Propofol Injection on Pain and Quality of Life in Chronic Daily Headache: A Randomized, Double-Blind, Controlled Trial"; Int'l Anesthesia Research Society; vol. 109 No. 6; Dec. 2009; p. 1972-1980.
Sheridan et al.; "Low-Dose Propofol for the Abortive Treatment of Pediatric Migraine in the Emergency Department"; Pediatric Emergency Care; vol. 28 No. 12; Dec. 2012; p. 1293-1296.
Sheridan e al .; "Low-Dose Propofol for Pediatric Migraine: a Prospective, Randomized Controlled Trial"; The Journal of Emergency Medicine; vol. 54 No. 5; 2018; p. 600-606.
Schneider et al.; "Propofol dependency after treatment of tension headache"; Addiction Biology; vol. 6; 2001; p. 263-265.

(56) References Cited

OTHER PUBLICATIONS

Sato et al.; "Low-dose intravenous propofol as a possible therapeutic option for acute confusional migraine"; American Journal of Emergency Medicine; vol. 35; 2017; 2 pages.

Reinsel et al.; "The P300 event-related potential during propofol sedation: a possible marker for amnesia?"; British Journal of Anesthesia; vol. 74; 1995; 674-680.

Razavi et al.; "Propofol and Alfentanil in Treatment of a Patient with Episodic Cluster Headache"; Anesth Pain Medicine; vol. 4(2); May 2014; 3 pages.

Mosier et al.; "Sedative Dosing of Propofol For Treatment of Migraine Headache In The Emergency Department: A Case Series"; Western Journal of Emergency Medicine; vol. 14 No. 6; Nov. 2013; p. 646-649.

Moshtaghion et al.; "The Efficacy of Propofol vs. Subcutaneous Sumatriptan for Treatment of Acute Migraine Headaches in the Emergency Department: A Double-Blinded Clinical Trial"; World Institute of Pain; 2014; 5 pages.

Mohseni et al.; "Propofol Alleviates Intractable Migraine Headache: A Case Report"; Anesthesiology and Pain Medicine; vol. 2(2); 2012; p. 94-96.

Mendes et al.; "Intravenous Propofol in the Treatment of Refractory Headache"; Headache; vol. 42; 2002; p. 638-641.

Long et al.; "Benign Headache Management in the Emergency Department"; The Journal of Emergency Medicine; vol. 54 No. 4; 2018; p. 458-468.

Krusz et al.; "Intravenous Propofol: Unique Effectiveness in Treating Intractable Migraine"; Headache; vol. 40; Mar. 2000; p. 224-230.

Ferrari et al.; "Oral triptans (serotonin 5-HT1B/1D agonists) in acute migraine treatment: a meta-analysis of 53 trials"; The Lancet; vol. 358; Nov. 2001; p. 1668-1675.

Drummond-Lewis et al.; "Propofol: A New Treatment Strategy for Refractory Migraine Headache"; Pain Medicine; vol. 3 No. 4; 2002; p. 366-369.

Dhir et al.; "Propofol hemisuccinate suppresses cortical spreading depression"; Neuroscience Letters; vol. 514; 2012; p. 67-70.

Dhir et al.; "Seizure Protection by Intrapulmonary Delivery of Propofol Hemisuccinate"; The Journal of Pharmacology and Experimental Therapeutics; vol. 336 No. 1; 2011; p. 215-222.

Bloomstone; "Propofol: A Novel Treatment for Breaking Migraine Headache"; Anestesiology; vol. 106; 2007; p. 405-406.

Baker; "The Anticonvulsant Effects of Propofol and a Propofol Analog, 2,6-Diisopropyl-4-(1-Hydroxy-2,2,2-Trifluoroethyl)Phenol, in a 6 Hz Partial Seizure Model"; Int'l Anesthesia Research Society; vol. 112 No. 2; Feb. 2011; p. 340-344.

Kurt et al.; "Anxiolytic-Like Profile of Propofol, a General Anesthetic, in the Plus-Maze Test in Mice"; Polish Journal of Pharmacology; vol. 55; 2003; p. 973-977.

Zacny et al.; "Propofol at Conscious Sedation Doses Produces Mild Analgesia to Cold Pressor-Induced Pain in Healthy Volunteers"; Journal of Clinical Anesthesia; vol. 8; 1996; p. 469-474.

Nishiyama et al.; "Intrathecal propofol has analgesic effects on inflammation-induced pain in rats"; Canadian Journal of Anesthesia; vol. 51(9); 2004; p. 899-904.

Bennett et al.; "Postoperative Infections Traced to Contamination of an Intravenous Anesthetic, Propofol"; The New England Journal of Medicine; vol. 333; 1995; p. 147-154.

Pytliak et al.; "Serotonin Receptors—From Molecular Biology to Clinical Applications"; Physiological Research; 2011; 19 pages.

Fechner et al.; "Pharmacokinetics and Clinical Pharmacodynamics of the New Propofol Prodrug GPI 15715 in Volunteers"; Anesthesiology; vol. 99 No. 2; Aug. 2003; p. 303-313.

Mahajan et al.; "Fospropofol"; Journal of Pharmacology and Pharmacotherapeutics; vol. 3 No. 3; Jul.-Sep. 2012; p. 293-296.

Borgeat et al.; "Subhypnotic Doses of Propofol Relieve Pruritus Associated with Liver Disease"; Gastroenterology; vol. 104; Jan. 1993; p. 244-247.

Kam et al.; "Pruritus—itching for a cause and relief?"; Anaesthesia; vol. 51; 1996; p. 1133-1138.

Pain et al.; "Effect of Nonsedative Doses of Propofol on an Innate Anxiogenic Situation in Rats"; Anesthesiology; vol. 90; 1999; p. 196-196.

\* cited by examiner

FOSPROPOFOL SALTS, METHODS AND COMPOSITIONS

CROSS-REFERENCE TO RELATED APPLICATION

This application is a divisional of U.S. patent application Ser. No. 17/168,365, filed Feb. 5, 2021, which claims the benefit of U.S. Provisional Patent Application No. 62/970,324, filed on Feb. 5, 2020, the entirety of which are incorporated by reference herein.

TECHNICAL FIELD

The present disclosure pertains to fosprofol salts, and the use of fospropofol salts, or mixtures thereof, to treat migraine.

BACKGROUND

Propofol (2,6-diisopropylphenol) is an intravenous short-acting anesthetic agent that has gained acceptance for inducing and maintaining anesthesia and for procedural sedation. Propofol is a highly lipophilic drug which must be formulated as a suspension with a lipid carrier in aqueous medium. Consequently, propofol derivatives were developed which possessed increased water solubility to simplify formulation. One of these was Fospropofol ((2,6-diisopropylphenoxy)methyl dihydrogen phosphate). Fospropofol is a water-soluble, phosphono-O-methyl prodrug of propofol that was approved in the United States as an alternative to propofol for monitored anesthesia care during procedures.

Fospropofol is rapidly metabolized by endothelial alkaline phosphatases to release propofol, phosphate, and formaldehyde. The small amounts of formaldehyde is rapidly converted to formate and safely eliminated, similar to the other available phosphate methyl prodrugs such as fosphenytoin.

Migraine is a primary headache disorder characterized by recurrent headaches that may be moderate or severe. Typically, the headaches affect one half of the head, are pulsating in nature, and last from two to 72 hours. Many people experience migraines lasting for at least four hours or even lasting for days.

Migraines are called primary headaches because the pain is not caused by another disorder or disease such as a brain tumor or head injury. Symptoms of migraines may include nausea, vomiting, and sensitivity to light, sound, or smell. The pain is generally made worse by physical activity. Some cause pain on just the right side or left side of the head, others result in pain all over. Migraine sufferers may have moderate or severe pain and usually can't participate in normal activities because of the pain. Often when a migraine strikes, people try to find a quiet, dark room.

Many people have an aura with a migraine, typically a short period of visual disturbance that signals that the headache will soon occur. Sufferers have reported seeing flashes or bright spots. Occasionally, an aura can occur with little or no headache following it.

The range of time someone is affected by an attack is often longer than the migraine itself, as there is a pre-monitory, or build-up phase, and a post-drome phase that can last one to two days. Different people have different triggers and different symptoms.

Migraines are believed to be due to a mixture of environmental and genetic factors. Genomics of migraines have been examined and certain gene mutations have been associated with severe migraines, but the etiology is presumably polygenic. Changing hormone levels may also play a role, as migraines affect slightly more boys than girls before puberty and two to three times more women than men after puberty. Catamenial migraine is not uncommon in women associated with the menses.

Migraines are believed to involve the nerves and blood vessels of the brain. However, older ideas that migraines were principally vascular in nature are now considered to be incorrect. Although an exact cause is unknown, brain scans show that migraines may be due to "hyperactivity" in parts of the brain. This activity can spread across the cortex during the course of the migraine, which is known as spreading cortical depression.

Migraines are one of the most common causes of disability. There are about 100 million people with recurrent headaches in the U.S. and about 37 million of these people have migraines. The World Health Organization suggests that 18 percent of women and 7 percent of men in the U.S. suffer from migraines. Globally, approximately 15% of people are affected by migraines. Migraines most often start at puberty and get worse during middle age. In some women, migraines become less common following menopause. Migraine headaches are a common cause of disability in the United States, affecting approximately 27 million American adults, or 17.1% of women and 5.6% of men.

There is often a distinction between a migraine with an aura and a migraine without an aura. The most current terminology defines a classic migraine as a migraine with an aura and non-classic or common migraine as a migraine without aura. Also, there is often a distinction between chronic migraine and episodic migraine. Chronic migraine, which affects 3.2 million Americans (2%), is characterized by the presence of migraine symptoms for at least 15 days per month, lasting at least 4 hours, and for longer than 3 months in duration. Episodic migraine, in contrast, causes symptoms for fewer than 15 days per month.

Current treatments for migraine are divided into acute, abortive agents (analgesics, triptans, ergots, etc.), and medications that will prevent migraine onset. Initial recommended treatment is with simple pain medication such as ibuprofen and paracetamol (acetaminophen) for the headache, medication for the nausea, and the avoidance of triggers. Specific medications such as triptans or ergotamines may be used in those for whom simple pain medications are not effective. Caffeine may also be used for treatment.

The oral triptan preparations (Imitrex, Maxalt, Zomig, Axert, Relpax) are thought to be generally effective in only 60 to 70% of patients. Indeed, a large percentage of migraine sufferers become resistant or refractory to current migraine treatments. Also, in a significant number of patients (perhaps 30%) in which they are effective, they produce cardiological side effects which are unpleasant, lead to poor compliance, and which can be quite problematic.

Various preparations of NSAIDS such as diclofenac and ketorolac are used to treat the symptomatology of migraines, but their effect is limited and they do not abrogate the onset of the migraine as do the Triptans and the CGRP agents (see below). Opiates are generally ineffective and are contraindicated. The antidepressant and mood stabilizer Amitriptyline is quite effective in low dose in a small subset of patients, as are anticonvulsants and mood stabilizers such as Topiramate, Valproate, and Gabapentin.

The recent approval (2018) of agents which act on the calcitonin gene-related peptide (CGRP) has been beneficial in migraine. These are all antibodies with high affinity binding to the CGRP receptor. They include Aimovig® (erenumab), a IgG2 humanized monoclonal antibody; Emgaliyt® Galcanezumab, an IgG4 Kappa-chain dimer monoclonal antibody; and Ajovy® (fremanezumab), an IgG2 Δa/kappa humanized monoclonal antibody. However, although these agents work in many patients in which the triptans are ineffective or not tolerated, there are still a significant subset of patients in which they are ineffective. Furthermore, being recombinant biologicals, they are rather expensive, and need to be administered monthly by injection in order to continue to prevent migraines in those patients in which they do work.

CGRP targeted small molecules such as Ubrogepant (MK-1602) and Rimegepant (BMS-927711) remain in late-phase clinical trials. However, they will presumably target the same subset of patients who will respond the CGRP antibodies described supra.

Thus, there is a need for additional methods of treating migraine, particularly refractory migraine.

SUMMARY

The present disclosure provides pharmaceutically acceptable salts of fospropofol, wherein said salt is a potassium, diethylamine, t-butylamine, ethylene diamine, benzathine, piperazine, ethanolamine, diethanolamine, ammonium, tromethamine, benethamine, histidine, calcium, magnesium, or zinc salt.

The present disclosure also provides pharmaceutical compositions comprising a fospropofol salt of the disclosure and a pharmaceutically acceptable excipient.

The present disclosure also provides methods of treating migraine in a patient in need thereof, comprising administering to the patient an effective amount of a fospropofol salt of the disclosure.

The present disclosure provides methods and compositions that meet the need for additional migraine treatments, including treatments for refractory migraine.

The disclosure is directed to methods of treating migraine in a patient in need thereof, comprising administering to the patient an effective amount of fospropofol, a pharmaceutically acceptable salt of fospropofol, or mixtures thereof, in one or more doses.

The disclosure is also directed to methods of treating migraine in a patient in need thereof, comprising administering to the patient a composition comprising an effective amount of fospropofol, a pharmaceutically acceptable salt of fospropofol, or mixtures thereof, in one or more doses.

The disclosure is also directed to pharmaceutical compositions comprising fospropofol, a pharmaceutically acceptable salt of fospropofol, or mixtures thereof, and a pharmaceutically acceptable excipient.

DETAILED DESCRIPTION OF THE INVENTION

Definitions

Figure 1:
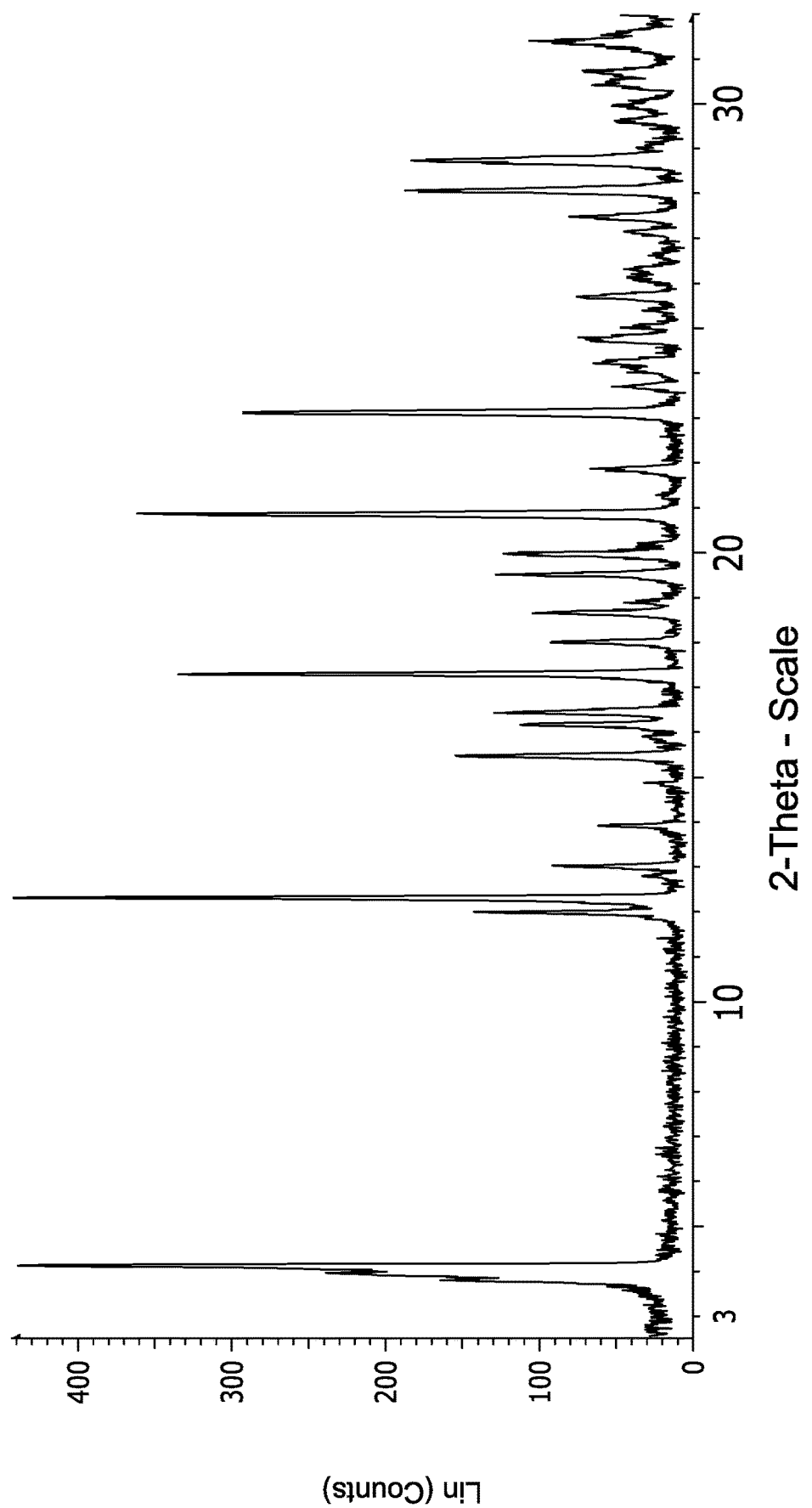
FIG. 1 shows an X-ray powder diffractogram (XRPD) of a potassium salt of fospropofol.

A crystal form may be referred to herein as being characterized by graphical data "as shown in" a Figure. Such data include, for example, powder X-ray diffractograms (XRPD), Differential Scanning calorimetry (DSC) thermograms, thermogravimetric analysis (TGA) profiles, and dynamic vapor sorption profiles (DVS). As is well-known in the art, the graphical data potentially provides additional technical information to further define the respective solid state form which can not necessarily be described by reference to numerical values or peak positions alone. Thus, the term "substantially as shown in" when referring to graphical data in a Figure herein means a pattern that is not necessarily identical to those depicted herein, but that falls within the limits of experimental error or deviations, when considered by one of ordinary skill in the art. The skilled person would readily be able to compare the graphical data in the Figures herein with graphical data generated for an unknown crystal form and confirm whether the two sets of graphical data are characterizing the same crystal form or two different crystal forms.

The terms "polymorph" or "crystalline form" refer to distinct crystal arrangements of the same chemical composition. The term "form" includes polymorphs, crystalline forms, and non-crystalline (amorphous) solids.

A solid, crystalline form may be referred to herein as "polymorphically pure" or as "substantially free of any other form." As used herein in this context, the expression "substantially free of any other forms" will be understood to mean that the solid form contains about 20% or less, about 10% or less, about 5% or less, about 2% or less, about 1% or less, or 0% of any other forms of the subject compound as measured, for example, by XRPD. Thus, a solid form of a fospropofol salt described herein as substantially free of any other solid forms would be understood to contain greater than about 80% (w/w), greater than about 90% (w/w), greater than about 95% (w/w), greater than about 98% (w/w), greater than about 99% (w/w), or about 100% of the subject solid form of the fospropofol salt. Accordingly, in some embodiments of the disclosure, the described solid forms of fospropofol salts may contain from about 1% to about 20% (w/w), from about 5% to about 20% (w/w), or from about 5% to about 10% (w/w) of one or more other solid forms of fospropofol salts.

As used herein, unless stated otherwise, XRPD peaks reported herein are measured using CuKα radiation, λ=1.5419 Å.

The modifier "about" should be considered as disclosing the range defined by the absolute values of the two endpoints. For example, the expression "from about 2 to about 4" also discloses the range "from 2 to 4." When used to modify a single number, the term "about" refers to plus or minus 10% of the indicated number and includes the indicated number. For example, "about 10%" indicates a range of 9% to 11%, and "about 1" means from 0.9-1.1.

The term "migraine," as used herein, refers to a chronic neurovascular disorder characterized by recurrent attacks of often severe headache ("migraine attacks"), typically accompanied by nausea and sensitivity to light and/or sound. Migraine is a clinical diagnosis, criteria for which would be known and understood by those practicing in the treatment of migraine, and would include, for example, the criteria proposed by the International Headache Society (IHS). See http://ihs-classification.org/en/.

The term "effective amount", as used herein, refers to an amount sufficient to reduce or eliminate the patient's migraine pain. The effective amount may be the amount given in a single dose, or may be the cumulative amount given in multiple doses.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, diluent, or release modifier to facilitate administration of an agent and that is compatible therewith.

"Refractory migraine," as used herein, refers to migraine that fails to respond to pharmacologic treatment. Failure to respond in this regard includes, for example, failure of a pharmacological treatment to eliminate migraine pain, as well as failure of a pharmacological treatment to reduce severe or moderate migraine pain to mild migraine pain.

The terms "administering" or "administration", as used herein, refer to delivering fospropofol into or onto the patient's body in a manner that results in the presence of propofol in the patient's systemic circulation. Any such method of administering may be used in performing the methods of the present disclosure. In some embodiments of the disclosed methods, the administering is oral, peroral, subcutaneous, intramuscular, intravenous, transmucosal, sublingual, buccal, transdermal, intraintestinal, rectal, or intrapulmonary.

As used herein, the term "modified release dosage form" refers to a dosage form that releases the encompassed fospropofol over an extended period of time.

DESCRIPTION

The present disclosure relates to pharmaceutically acceptable salts of fospropofol, processes for preparation thereof, pharmaceutical compositions comprising those salt forms, and methods of treatment using those salt forms.

The name "fospropofol" is another name for (2,6-diisopropylphenoxy)methyl dihydrogen phosphate, which has the structure

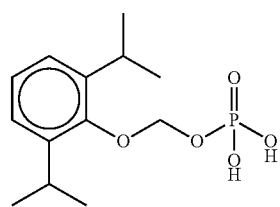

The preparation of fospropol has been described in the art.

The fospropofol salts according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

In some aspects, the present disclosure pertains to pharmaceutically acceptable salts of fospropofol. In some embodiments, the pharmaceutically acceptable salts of fospropofol are the potassium, diethylamine, t-butyl amine, ethylene diamine, benzathine, piperazine, ethanolamine, diethanolamine, ammonium, tromethamine, benethamine, histidine, calcium, magnesium, or zinc salts.

In some embodiments, the pharmaceutically acceptable salt of fospropofol is the potassium salt.

In some embodiments, the fospropofol potassium salt has an XRPD substantially as shown in FIG. 1. The XRPD of the potassium salt of fospropofol shown in FIG. 1 comprises reflection angles (degrees 2-theta±0.2 degrees 2-theta), and relative intensities as shown in Table 1:

TABLE 1

XRPD Data for Potassium salt of Fospropofol

| Angle (degrees 2-theta ± 0.2 degrees 2-theta) | Relative Intensity |
|---|---|
| 4.1 | 99.1 |
| 12.0 | 31.9 |
| 12.3 | 100.0 |
| 13.0 | 20.5 |
| 13.9 | 13.7 |
| 14.9 | 6.9 |
| 15.5 | 34.6 |
| 15.9 | 7.6 |
| 16.2 | 25.5 |
| 16.4 | 29.8 |
| 17.3 | 62.3 |
| 18.0 | 21.1 |
| 18.7 | 21.4 |
| 18.9 | 10.3 |
| 19.5 | 28.8 |
| 20.0 | 27.7 |
| 20.9 | 48.4 |
| 21.8 | 11.0 |
| 23.1 | 66.4 |
| 23.7 | 8.5 |
| 24.0 | 9.4 |
| 24.2 | 12.6 |
| 24.8 | 13.0 |
| 25.0 | 10.5 |
| 25.7 | 15.5 |
| 26.1 | 9.1 |
| 26.3 | 9.4 |
| 27.1 | 8.8 |
| 27.5 | 15.1 |
| 28.1 | 39.6 |
| 28.7 | 37.1 |
| 29.1 | 6.7 |
| 29.6 | 8.3 |
| 30.0 | 12.2 |
| 30.4 | 14.8 |
| 30.7 | 16.0 |
| 31.4 | 24.4 |

In some embodiments of the present disclosure, the potassium salt of fospropofol is characterized by an XRPD pattern comprising a peak at one of the angles listed in Table 1. In some aspects, the potassium salt of fospropofol is characterized by an XRPD pattern comprising more than one peak at one of the angles listed in Table 1 above. In other aspects, the potassium salt of fospropofol is characterized by an XRPD pattern comprising two peaks selected from the angles listed in Table 1 above. In other aspects, the potassium salt of fospropofol is characterized by an XRPD pattern comprising three peaks selected from the angles listed in Table 1 above. In other aspects, the potassium salt of fospropofol is characterized by an XRPD pattern comprising four peaks selected from the angles listed in Table 1 above. In other aspects, the potassium salt of fospropofol is characterized by an XRPD pattern comprising five peaks selected from the angles listed in Table 1 above. In other aspects, the potassium salt of fospropofol is characterized by an XRPD pattern comprising six peaks selected from the angles listed in Table 1 above. In other aspects, the potassium salt of fospropofol is characterized by an XRPD pattern comprising seven peaks selected from the angles listed in Table 1 above. In other aspects, the potassium salt of fospropofol is characterized by an XRPD pattern comprising eight peaks selected from the angles listed in Table 1 above. In other aspects, the potassium salt of fospropofol is characterized by an XRPD pattern comprising nine peaks selected from the angles listed in Table 1 above. In other aspects, the potassium salt of fospropofol is characterized by an XRPD pattern comprising ten peaks selected from the angles listed in Table 1 above. In other aspects, the potassium salt of fospropofol is characterized by an XRPD pattern comprising more than ten peaks selected from the angles listed in Table 1 above.

In some embodiments, the potassium salt of fospropofol is characterized by an XRPD pattern comprising a peak at 12.3, 17.3, and 20.9 degrees±0.2 degrees 2-theta. In other embodiments, the potassium salt of fospropofol is characterized by an XRPD pattern comprising peaks at 12.3, 17.3, 20.9, and 23.1 degrees±0.2 degrees 2-theta. In other embodiments, the potassium salt of fospropofol is characterized by an XRPD pattern comprising peaks at 12.3, 17.3, 20.9, 23.1, 28.1, and 28.7 degrees±0.2 degree 2-theta. In yet other embodiments, the potassium salt of fospropofol is characterized by an XRPD pattern comprising peaks at 12.3, 15.5, 16.2, 16.4, 17.3, 18.0, 18.7, 19.5, 20.0, 20.9, 23.1, 28.1, and 28.7 degrees±0.2 degree 2-theta.

In some embodiments of the present disclosure, the potassium salt of fospropofol is characterized by an XRPD pattern comprising peaks at three or more of 12.3, 15.5, 16.2, 16.4, 17.3, 18.0, 18.7, 19.5, 20.0, 20.9, 23.1, 28.1, and 28.7 degrees±0.2 degrees 2-theta. In some embodiments of the present disclosure, the potassium salt of fospropofol is characterized by an XRPD pattern comprising peaks at four or more of 12.3, 15.5, 16.2, 16.4, 17.3, 18.0, 18.7, 19.5, 20.0, 20.9, 23.1, 28.1, and 28.7 degrees±0.2 degrees 2-theta. In some embodiments of the present disclosure, the potassium salt of fospropofol is characterized by an XRPD pattern comprising peaks at five or more of 12.3, 15.5, 16.2, 16.4, 17.3, 18.0, 18.7, 19.5, 20.0, 20.9, 23.1, 28.1, and 28.7 degrees±0.2 degrees 2-theta. In some embodiments of the present disclosure, the potassium salt of fospropofol is characterized by an XRPD pattern comprising peaks at six or more of 12.3, 15.5, 16.2, 16.4, 17.3, 18.0, 18.7, 19.5, 20.0, 20.9, 23.1, 28.1, and 28.7 degrees±0.2 degrees 2-theta. In some embodiments of the present disclosure, the potassium salt of fospropofol is characterized by an XRPD pattern comprising peaks at seven or more of 12.3, 15.5, 16.2, 16.4, 17.3, 18.0, 18.7, 19.5, 20.0, 20.9, 23.1, 28.1, and 28.7 degrees±0.2 degrees 2-theta.

Figure 2:
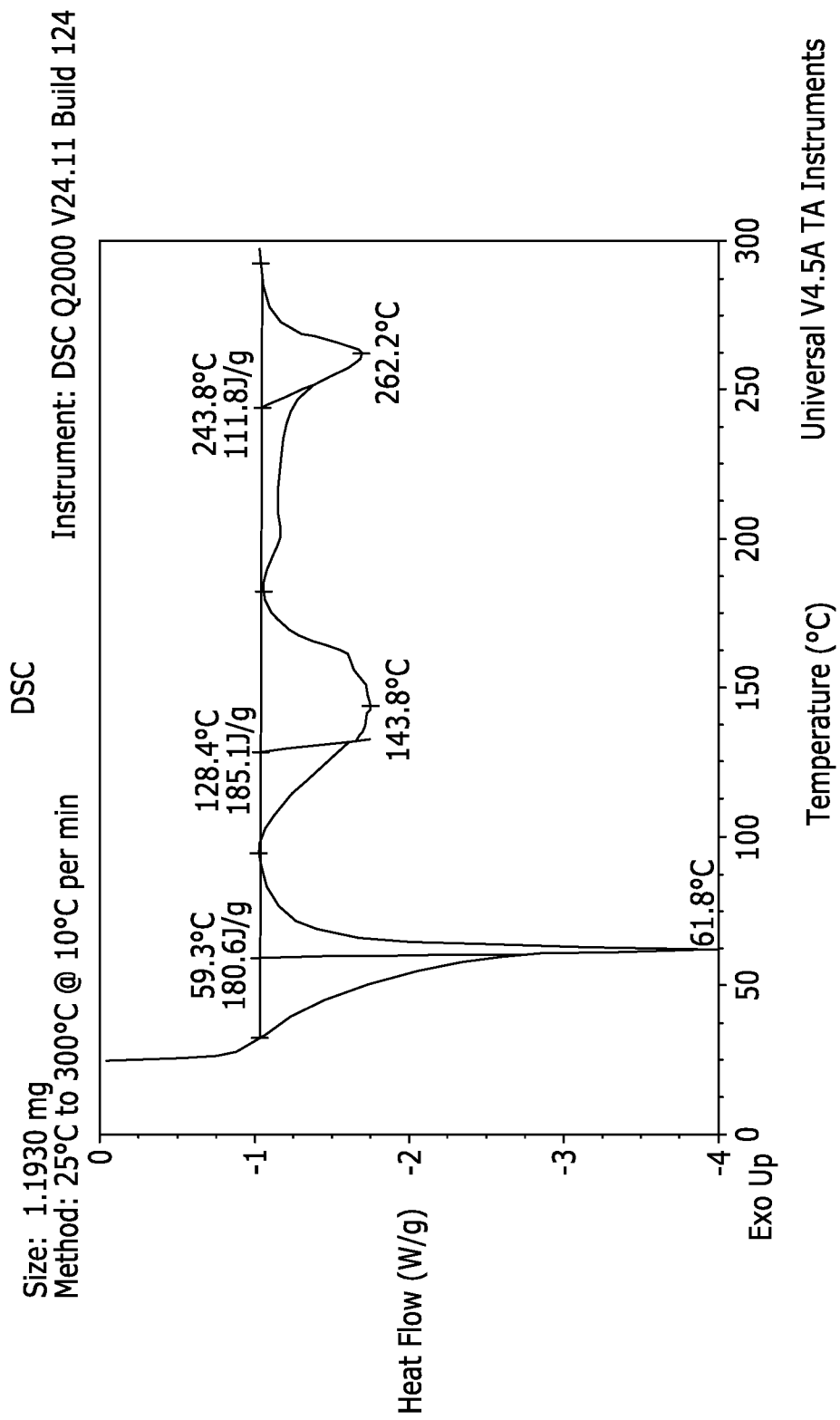
FIG. 2 shows a differential scanning calorimetry (DSC) profile of a potassium salt of fospropofol.

The potassium salt of fospropofol can be characterized by a DSC thermogram substantially as shown in FIG. 2. As FIG. 2 shows, the potassium salt of fospropofol produced endothermic peaks at 61.8° C., 143.8° C., and 262.2° C.

when heated at a rate of 10° C./min. In some embodiments of the present disclosure, the potassium salt of fospropofol is characterized by a DSC thermogram comprising an endothermic peak at about 62° C. In some embodiments of the present disclosure, the potassium salt of fospropofol is characterized by a DSC thermogram comprising an endothermic peak at about 144° C. In some embodiments of the present disclosure, the potassium salt of fospropofol is characterized by a DSC thermogram comprising an endothermic peak at about 262° C.

In some embodiments of the present disclosure, the potassium salt of fospropofol is characterized by an XRPD pattern comprising peaks at 12.3, 17.3, and 20.9 degrees±0.2 degrees 2-theta, and a DSC thermogram comprising an endothermic peak at about 62° C., 144° C., or 262° C. when heated at a rate of 10° C./min.

In some embodiments, the pharmaceutically acceptable salt of fospropofol is the diethylamine salt.

Figure 3:
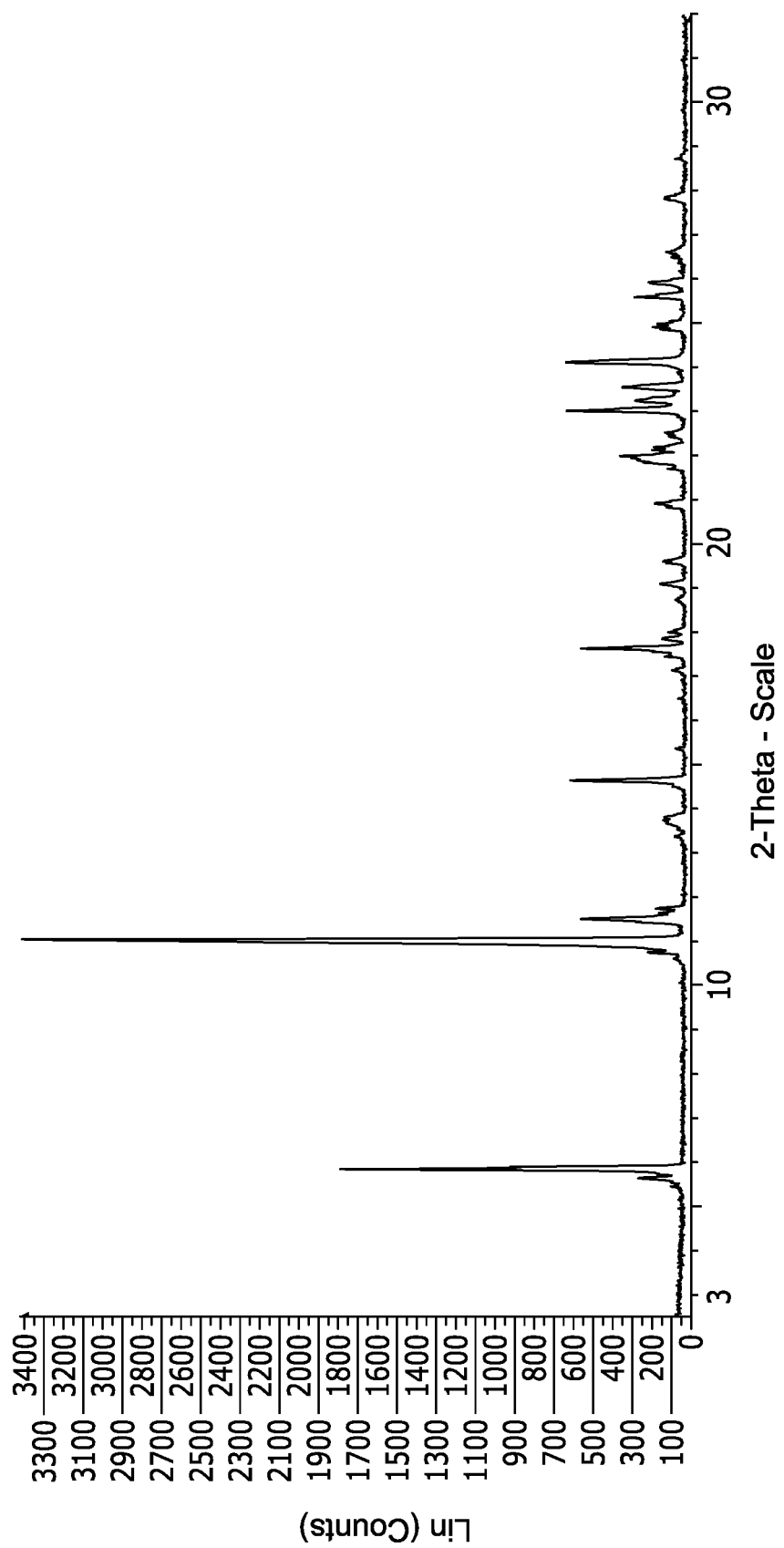
FIG. 3 shows an X-ray powder diffractogram (XRPD) of a diethylamine salt of fospropofol (Form II).

In other embodiments, the diethylamine salt of fospropofol (Form II) has an XRPD substantially as shown in FIG. 3. The XRPD of the diethylamine salt of fospropofol shown in FIG. 3 comprises reflection angles (degrees 2-theta±0.2 degrees 2-theta), and relative intensities as shown in Table 2 Å:

TABLE 2A

XRPD Data for Form II Diethylamine salt of Fospropofol

| Angle (degrees 2-theta ± 0.2 degrees 2-theta) | Relative Intensity |
|---|---|
| 5.6 | 7.7 |
| 5.8 | 52.5 |
| 11.0 | 100.0 |
| 11.5 | 16.6 |
| 11.7 | 5.1 |
| 13.7 | 3.9 |
| 14.6 | 18.3 |
| 17.6 | 16.9 |
| 17.8 | 4.3 |
| 18.0 | 3.4 |
| 18.7 | 2.2 |
| 19.1 | 4.5 |
| 19.6 | 4.3 |
| 20.9 | 5.3 |
| 22.0 | 10.7 |
| 22.2 | 5.6 |
| 22.5 | 3.4 |
| 23.0 | 18.6 |
| 23.2 | 8.4 |
| 23.5 | 10.4 |
| 24.1 | 18.9 |
| 24.9 | 5.7 |
| 25.6 | 8.5 |
| 25.9 | 6.2 |

In some embodiments of the present disclosure, the diethylamine salt of fospropofol is characterized by an XRPD pattern comprising a peak at one of the angles listed in Table 2 Å. In other aspects, the diethylamine salt of fospropofol is characterized by an XRPD pattern comprising more than one peak at one of the angles listed in Table 2A above. In other aspects, the diethylamine salt of fospropofol is characterized by an XRPD pattern comprising two peaks selected from the angles listed in Table 2A above. In other aspects, the diethylamine salt of fospropofol is characterized by an XRPD pattern comprising three peaks selected from the angles listed in Table 2A above. In other aspects, the diethylamine salt of fospropofol is characterized by an XRPD pattern comprising four peaks selected from the angles listed in Table 2A above. In other aspects, the diethylamine salt of fospropofol is characterized by an XRPD pattern comprising five peaks selected from the angles listed in Table 2A above. In other aspects, the diethylamine salt of fospropofol is characterized by an XRPD pattern comprising six peaks selected from the angles listed in Table 2A above. In other aspects, the diethylamine salt of fospropofol is characterized by an XRPD pattern comprising seven peaks selected from the angles listed in Table 2A above. In other aspects, the diethylamine salt of fospropofol is characterized by an XRPD pattern comprising eight peaks selected from the angles listed in Table 2A above. In other aspects, the diethylamine salt of fospropofol is characterized by an XRPD pattern comprising nine peaks selected from the angles listed in Table 2A above. In other aspects, the diethylamine salt of fospropofol is characterized by an XRPD pattern comprising ten peaks selected from the angles listed in Table 2A above. In other aspects, the diethylamine salt of fospropofol is characterized by an XRPD pattern comprising more than ten peaks selected from the angles listed in Table 2A above.

In some embodiments, the diethylamine salt of fospropofol is characterized by an XRPD pattern comprising a peaks at 5.8 and 11.0 degrees±0.2 degrees 2-theta. In other embodiments, the diethylamine salt of fospropofol is characterized by an XRPD pattern comprising peaks at 5.8, 11.0, and 11.5 degrees±0.2 degrees 2-theta. In other embodiments, the diethylamine salt of fospropofol is characterized by an XRPD pattern comprising peaks at 5.8, 11.0, 11.5, 14.6, and 17.6 degrees±0.2 degree 2-theta. In yet other embodiments, the diethylamine salt of fospropofol is characterized by an XRPD pattern comprising peaks at 5.8, 11.0, 11.5, 14.6, 17.6, 22.0, 23.0, and 24.1 degrees±0.2 degree 2-theta.

In some embodiments of the present disclosure, the diethylamine salt of fospropofol is characterized by an XRPD pattern comprising peaks at two or more of 5.8, 11.0, 11.5, 14.6, 17.6, 22.0, 23.0, and 24.1 degrees±0.2 degrees 2-theta. In some embodiments of the present disclosure, the diethylamine salt of fospropofol is characterized by an XRPD pattern comprising peaks at three or more of 5.8, 11.0, 11.5, 14.6, 17.6, 22.0, 23.0, and 24.1 degrees±0.2 degrees 2-theta. In some embodiments of the present disclosure, the diethylamine salt of fospropofol is characterized by an XRPD pattern comprising peaks at four or more of 5.8, 11.0, 11.5, 14.6, 17.6, 22.0, 23.0, and 24.1 degrees±0.2 degrees 2-theta. In some embodiments of the present disclosure, the diethylamine salt of fospropofol is characterized by an XRPD pattern comprising peaks at five or more of 5.8, 11.0, 11.5, 14.6, 17.6, 22.0, 23.0, and 24.1 degrees±0.2 degrees 2-theta.

Figure 4:
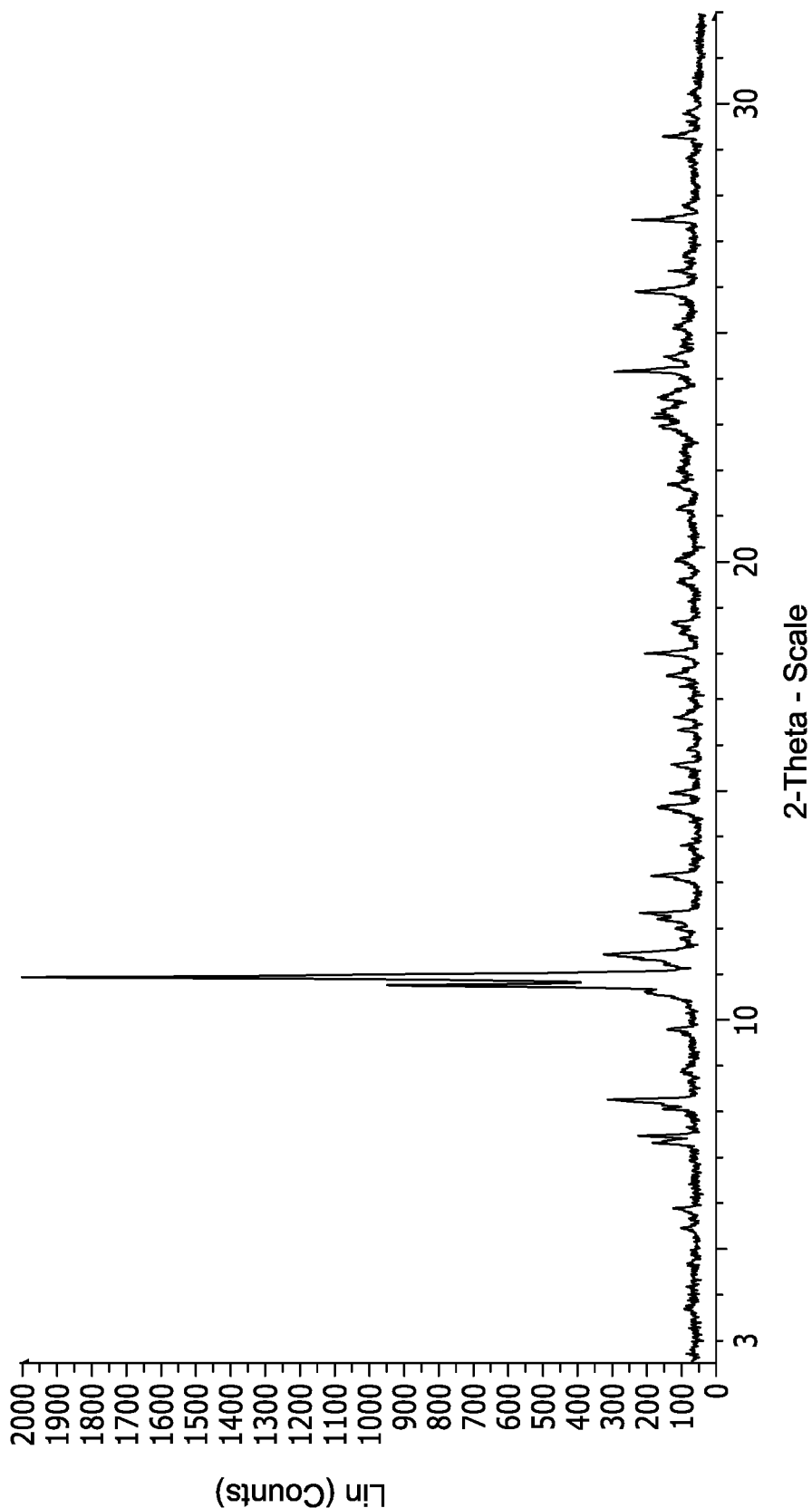
FIG. 4 shows an X-ray powder diffractogram (XRPD) of a diethylamine salt of fospropofol (Form I).

In some embodiments, the diethylamine salt of fospropofol (Form I) has an XRPD substantially as shown in FIG. 4. The XRPD of the diethylamine salt of fospropofol shown in FIG. 4 comprises reflection angles (degrees 2-theta±0.2 degrees 2-theta), and relative intensities as shown in Table 2:

TABLE 2

XRPD Data for Form I Diethylamine salt of Fospropofol

| Angle (degrees 2-theta ± 0.2 degrees 2-theta) | Relative Intensity |
|---|---|
| 5.9 | 6.2 |
| 7.3 | 9.2 |
| 7.4 | 11.4 |
| 8.2 | 15.7 |
| 9.8 | 7.1 |
| 10.6 | 10.0 |

TABLE 2-continued

XRPD Data for Form I Diethylamine salt of Fospropofol

| Angle (degrees 2-theta ± 0.2 degrees 2-theta) | Relative Intensity |
|---|---|
| 10.7 | 47.1 |
| 10.9 | 100.0 |
| 11.4 | 16.3 |
| 12.2 | 8.5 |
| 12.3 | 10.9 |
| 13.1 | 9.1 |
| 14.6 | 8.2 |
| 14.9 | 6.5 |
| 15.6 | 6.5 |
| 16.3 | 5.2 |
| 16.6 | 6.2 |
| 17.5 | 6.8 |
| 18.0 | 9.9 |
| 18.6 | 5.7 |
| 19.6 | 5.4 |
| 20.1 | 5.4 |
| 21.7 | 6.8 |
| 23.0 | 8.5 |
| 23.2 | 9.2 |
| 23.6 | 8.3 |
| 24.2 | 14.5 |
| 25.9 | 11.6 |
| 27.5 | 12.0 |

In some embodiments of the present disclosure, the diethylamine salt of fospropofol is characterized by an XRPD pattern comprising a peak at one of the angles listed in Table 2. In other aspects, the diethylamine salt of fospropofol is characterized by an XRPD pattern comprising more than one peak at one of the angles listed in Table 2 above. In other aspects, the diethylamine salt of fospropofol is characterized by an XRPD pattern comprising two peaks selected from the angles listed in Table 2 above. In other aspects, the diethylamine salt of fospropofol is characterized by an XRPD pattern comprising three peaks selected from the angles listed in Table 2 above. In other aspects, the diethylamine salt of fospropofol is characterized by an XRPD pattern comprising four peaks selected from the angles listed in Table 2 above. In other aspects, the diethylamine salt of fospropofol is characterized by an XRPD pattern comprising five peaks selected from the angles listed in Table 2 above. In other aspects, the diethylamine salt of fospropofol is characterized by an XRPD pattern comprising six peaks selected from the angles listed in Table 2 above. In other aspects, the diethylamine salt of fospropofol is characterized by an XRPD pattern comprising seven peaks selected from the angles listed in Table 2 above. In other aspects, the diethylamine salt of fospropofol is characterized by an XRPD pattern comprising eight peaks selected from the angles listed in Table 2 above. In other aspects, the diethylamine salt of fospropofol is characterized by an XRPD pattern comprising nine peaks selected from the angles listed in Table 2 above. In other aspects, the diethylamine salt of fospropofol is characterized by an XRPD pattern comprising ten peaks selected from the angles listed in Table 2 above. In other aspects, the diethylamine salt of fospropofol is characterized by an XRPD pattern comprising more than ten peaks selected from the angles listed in Table 2 above.

In some embodiments, the diethylamine salt of fospropofol is characterized by an XRPD pattern comprising a peak at 10.9 and 11.4 degrees±0.2 degrees 2-theta. In other embodiments, the diethylamine salt of fospropofol is characterized by an XRPD pattern comprising peaks at 10.9, 11.4, and 14.6 degrees±0.2 degrees 2-theta. In other embodiments, the diethylamine salt of fospropofol is characterized by an XRPD pattern comprising peaks at 10.9, 11.4, 14.6, and 24.2 degrees±0.2 degree 2-theta. In yet other embodiments, the diethylamine salt of fospropofol is characterized by an XRPD pattern comprising peaks at 10.9, 11.4, 14.6, 24.2, 25.9, and 27.5 degrees±0.2 degree 2-theta.

In some embodiments of the present disclosure, the diethylamine salt of fospropofol is characterized by an XRPD pattern comprising peaks at two or more of 10.9, 11.4, 14.6, 24.2, 25.9, and 27.5 degrees±0.2 degrees 2-theta. In some embodiments of the present disclosure, the diethylamine salt of fospropofol is characterized by an XRPD pattern comprising peaks at three or more of 10.9, 11.4, 14.6, 24.2, 25.9, and 27.5 degrees±0.2 degrees 2-theta. In some embodiments of the present disclosure, the diethylamine salt of fospropofol is characterized by an XRPD pattern comprising peaks at four or more of 10.9, 11.4, 14.6, 24.2, 25.9, and 27.5 degrees±0.2 degrees 2-theta. In some embodiments of the present disclosure, the diethylamine salt of fospropofol is characterized by an XRPD pattern comprising peaks at five or more of 10.9, 11.4, 14.6, 24.2, 25.9, and 27.5 degrees±0.2 degrees 2-theta.

Figure 5:
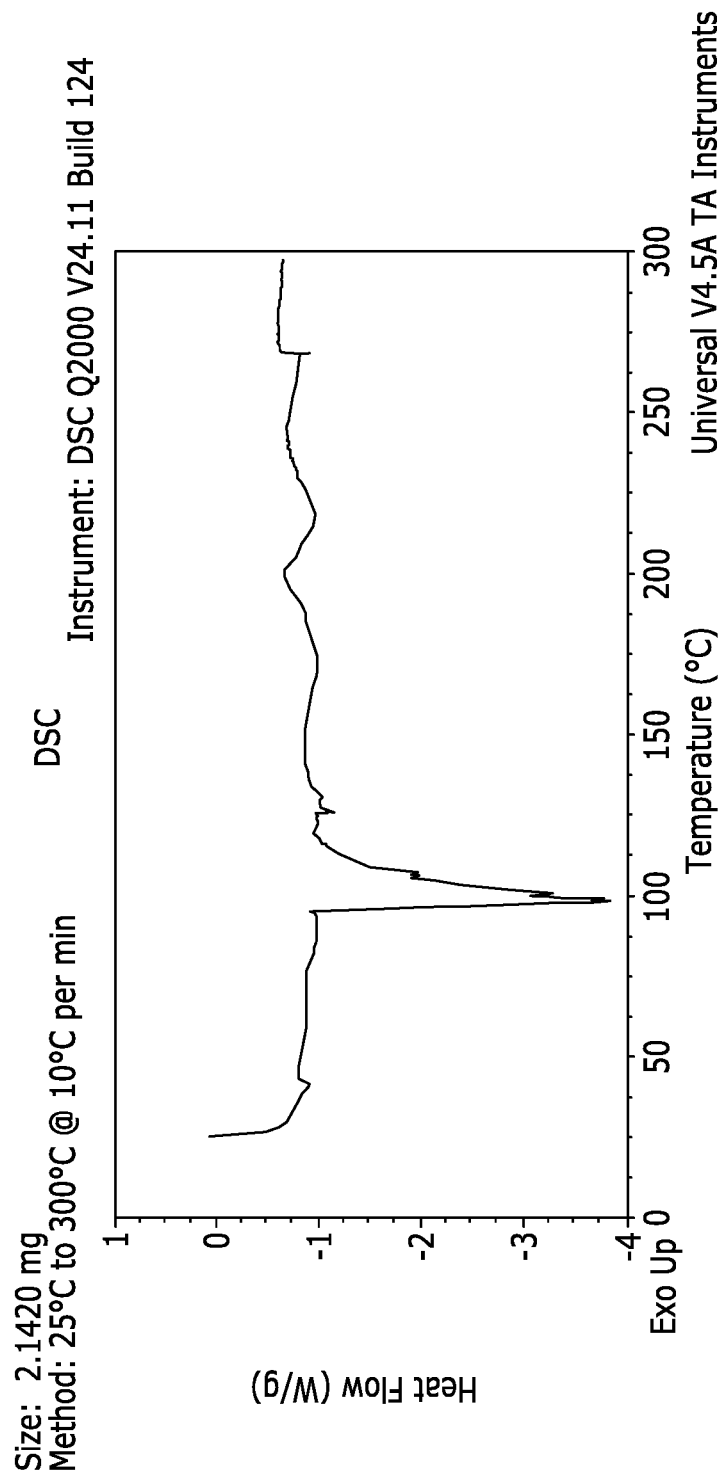
FIG. 5 shows a differential scanning calorimetry (DSC) profile of the diethylamine salt of fospropofol (Form I).

The Form I diethylamine salt of fospropofol can be characterized by a DSC thermogram substantially as shown in FIG. 5. As FIG. 5 shows, the diethylamine salt of fospropofol produced endothermic peaks at about 98° C. when heated at a rate of 10° C./min. In some embodiments of the present disclosure, the diethylamine salt of fospropofol is characterized by a DSC thermogram comprising an endothermic peak at about 98° C.

In some embodiments of the present disclosure, the diethylamine salt of fospropofol is characterized by an XRPD pattern comprising peaks at one or more of 10.9, 11.4, 14.6, 24.2, 25.9, and 27.5 degrees±0.2 degrees 2-theta, and a DSC thermogram comprising an endothermic peak at about 98° C. when heated at a rate of 10° C./min.

Figure 6:
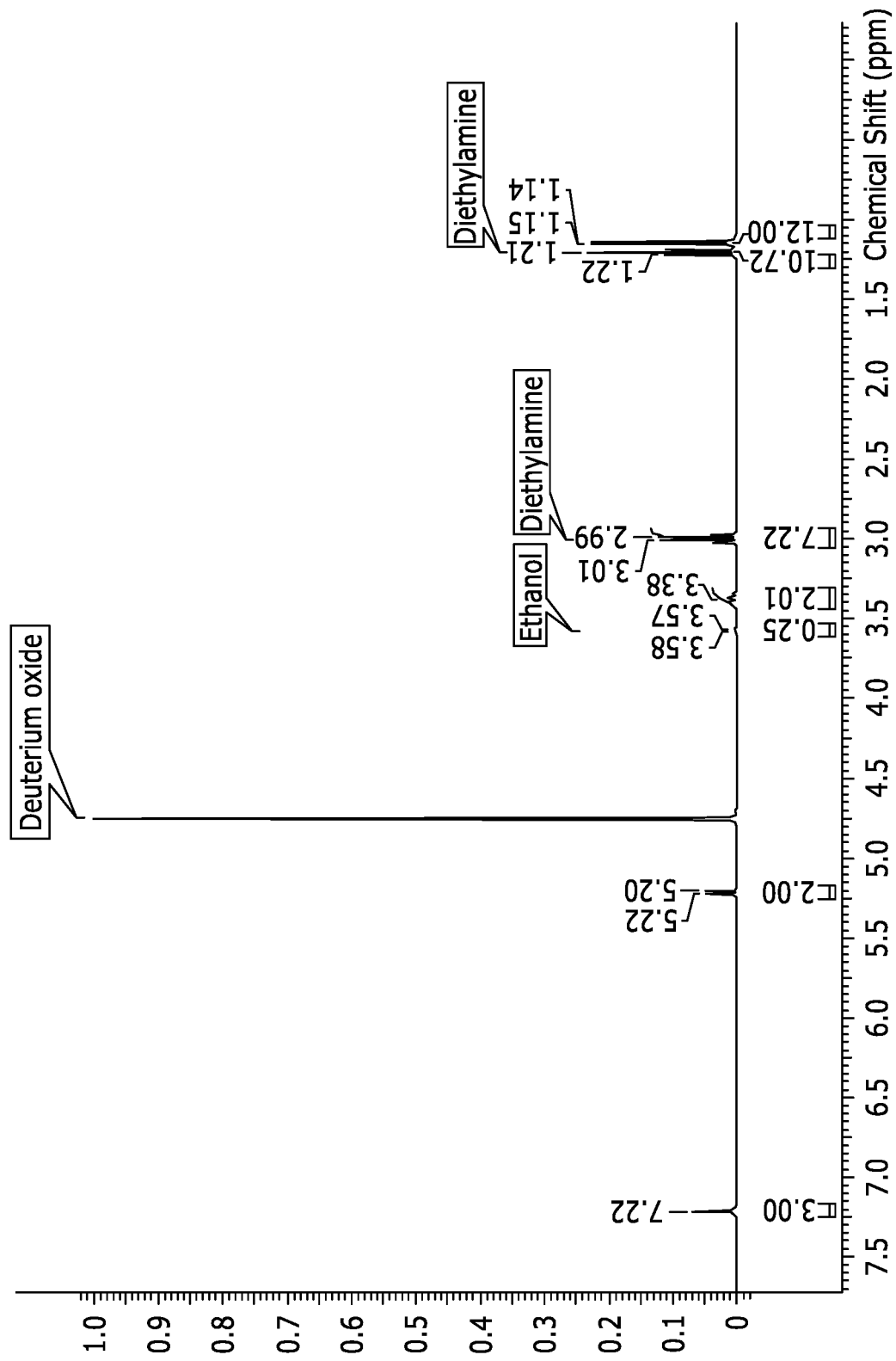
FIG. 6 shows a nuclear magnetic resonance (NMR) spectrum of a diethylamine salt of fospropofol (Form I).

The Form I diethylamine salt of fospropofol can be characterized by an NMR spectrum substantially as shown in FIG. 6.

In some embodiments, the pharmaceutically acceptable salt of fospropofol is the t-butylamine salt.

Figure 7:
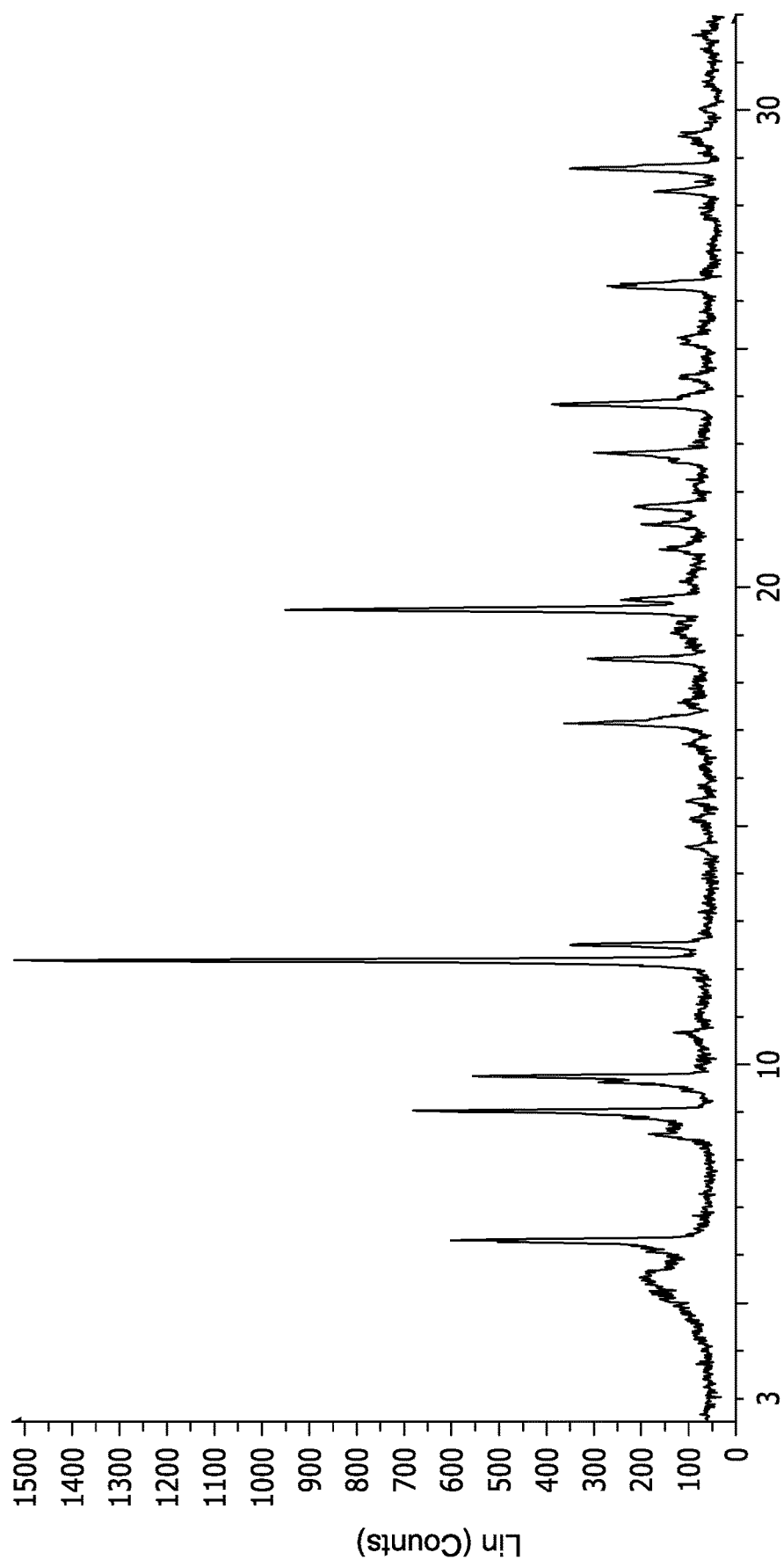
FIG. 7 shows an X-ray powder diffractogram (XRPD) of a t-butylamine salt of fospropofol.

In some embodiments, the t-butylamine salt of fospropofol has an XRPD substantially as shown in FIG. 7. The XRPD of the t-butylamine salt of fospropofol shown in FIG. 7 comprises reflection angles (degrees 2-theta±0.2 degrees 2-theta), and relative intensities as shown in Table 3:

TABLE 3

XRPD Data for t-butylamine salt of Fospropofol

| Angle (degrees 2-theta ± 0.2 degrees 2-theta) | Relative Intensity |
|---|---|
| 6.3 | 39.4 |
| 8.5 | 12.2 |
| 9.0 | 44.6 |
| 9.6 | 19.1 |
| 9.7 | 36.3 |
| 10.7 | 8.5 |
| 12.2 | 100.0 |
| 12.5 | 23.0 |
| 17.1 | 23.8 |
| 18.5 | 20.7 |
| 19.5 | 62.3 |
| 19.7 | 15.9 |
| 20.8 | 10.5 |
| 21.3 | 13.1 |
| 21.7 | 14.0 |
| 22.8 | 19.6 |
| 23.9 | 25.5 |

TABLE 3-continued

XRPD Data for t-butylamine salt of Fospropofol

| Angle (degrees 2-theta ± 0.2 degrees 2-theta) | Relative Intensity |
|---|---|
| 24.4 | 7.4 |
| 25.2 | 7.7 |
| 26.4 | 17.7 |
| 28.3 | 11.4 |
| 28.8 | 22.8 |
| 29.5 | 7.6 |

In some embodiments of the present disclosure, the t-butylamine salt of fospropofol is characterized by an XRPD pattern comprising a peak at one of the angles listed in Table 3. In other aspects, the t-butylamine salt of fospropofol is characterized by an XRPD pattern comprising more than one peak at one of the angles listed in Table 3 above. In other aspects, the t-butylamine salt of fospropofol is characterized by an XRPD pattern comprising two peaks selected from the angles listed in Table 3 above. In other aspects, the t-butylamine salt of fospropofol is characterized by an XRPD pattern comprising three peaks selected from the angles listed in Table 3 above. In other aspects, the t-butylamine salt of fospropofol is characterized by an XRPD pattern comprising four peaks selected from the angles listed in Table 3 above. In other aspects, the t-butylamine salt of fospropofol is characterized by an XRPD pattern comprising five peaks selected from the angles listed in Table 3 above. In other aspects, the t-butylamine salt of fospropofol is characterized by an XRPD pattern comprising six peaks selected from the angles listed in Table 3 above. In other aspects, the t-butylamine salt of fospropofol is characterized by an XRPD pattern comprising seven peaks selected from the angles listed in Table 3 above. In other aspects, the t-butylamine salt of fospropofol is characterized by an XRPD pattern comprising eight peaks selected from the angles listed in Table 3 above. In other aspects, the t-butylamine salt of fospropofol is characterized by an XRPD pattern comprising nine peaks selected from the angles listed in Table 3 above. In other aspects, the t-butylamine salt of fospropofol is characterized by an XRPD pattern comprising ten peaks selected from the angles listed in Table 3 above. In other aspects, the t-butylamine salt of fospropofol is characterized by an XRPD pattern comprising more than ten peaks selected from the angles listed in Table 3 above.

In some embodiments, the t-butylamine salt of fospropofol is characterized by an XRPD pattern comprising a peak at 12.2 degrees±0.2 degrees 2-theta. In other embodiments, the t-butylamine salt of fospropofol is characterized by an XRPD pattern comprising peaks at 9.0, 9.6, and 12.2 degrees±0.2 degrees 2-theta. In other embodiments, the t-butylamine salt of fospropofol is characterized by an XRPD pattern comprising peaks at 9.0, 9.6, 12.2, 17.1, and 19.5 degrees±0.2 degree 2-theta. In yet other embodiments, the t-butylamine salt of fospropofol is characterized by an XRPD pattern comprising peaks at 9.0, 9.6, 12.2, 17.1, 19.5, 21.3, 21.7, 23.9, 26.4, 28.3, and 28.8 degrees±0.2 degree 2-theta.

In some embodiments of the present disclosure, the t-butylamine salt of fospropofol is characterized by an XRPD pattern comprising peaks at three or more of 9.0, 9.6, 12.2, 17.1, 19.5, 21.3, 21.7, 23.9, 26.4, 28.3, and 28.8 degrees±0.2 degrees 2-theta. In some embodiments of the present disclosure, the t-butylamine salt of fospropofol is characterized by an XRPD pattern comprising peaks at four or more of 9.0, 9.6, 12.2, 17.1, 19.5, 21.3, 21.7, 23.9, 26.4, 28.3, and 28.8 degrees±0.2 degrees 2-theta. In some embodiments of the present disclosure, the t-butylamine salt of fospropofol is characterized by an XRPD pattern comprising peaks at five or more of 9.0, 9.6, 12.2, 17.1, 19.5, 21.3, 21.7, 23.9, 26.4, 28.3, and 28.8 degrees±0.2 degrees 2-theta. In some embodiments of the present disclosure, the t-butylamine salt of fospropofol is characterized by an XRPD pattern comprising peaks at six or more of 9.0, 9.6, 12.2, 17.1, 19.5, 21.3, 21.7, 23.9, 26.4, 28.3, and 28.8 degrees±0.2 degrees 2-theta. In some embodiments of the present disclosure, the t-butylamine salt of fospropofol is characterized by an XRPD pattern comprising peaks at seven or more of 9.0, 9.6, 12.2, 17.1, 19.5, 21.3, 21.7, 23.9, 26.4, 28.3, and 28.8 degrees±0.2 degrees 2-theta.

Figure 8:
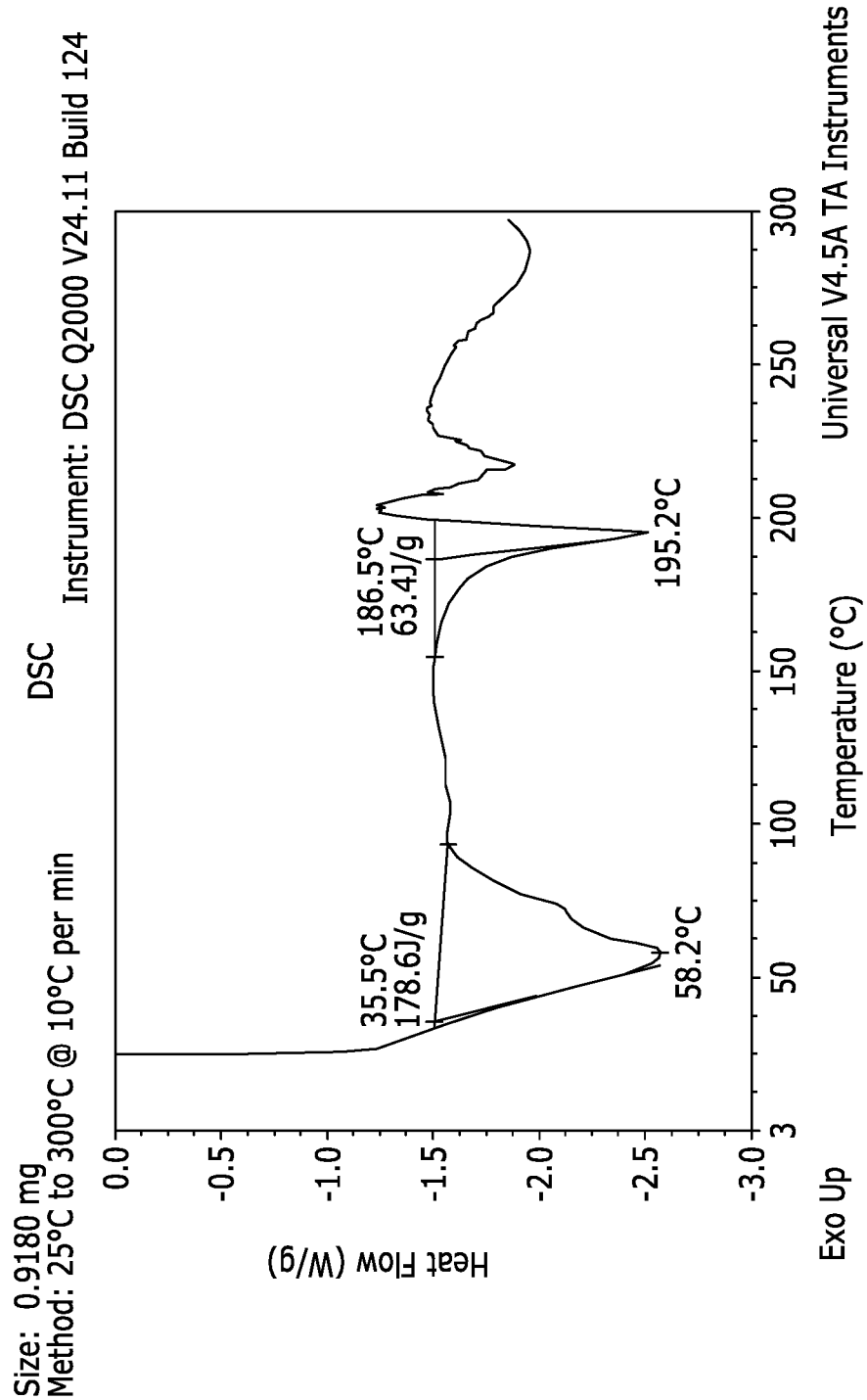
FIG. 8 shows a differential scanning calorimetry (DSC) profile of a t-butylamine salt of fospropofol.

The t-butylamine salt of fospropofol can be characterized by a DSC thermogram substantially as shown in FIG. 8. As FIG. 8 shows, the t-butylamine salt of fospropofol produced endothermic peaks at about 58.2° C. and 195.2° C. when heated at a rate of 10° C./min. In some embodiments of the present disclosure, the t-butylamine salt of fospropofol is characterized by a DSC thermogram comprising an endothermic peak at about 58° C., or at about 195° C.

In some embodiments of the present disclosure, the t-butylamine salt of fospropofol is characterized by an XRPD pattern comprising peaks at one or more of 9.0, 9.6, 12.2, 17.1, 19.5, 21.3, 21.7, 23.9, 26.4, 28.3, and 28.8 degrees±0.2 degrees 2-theta, and a DSC thermogram comprising an endothermic peak at about 58° C., or at about 195° C. when heated at a rate of 10° C./min.

Figure 9:
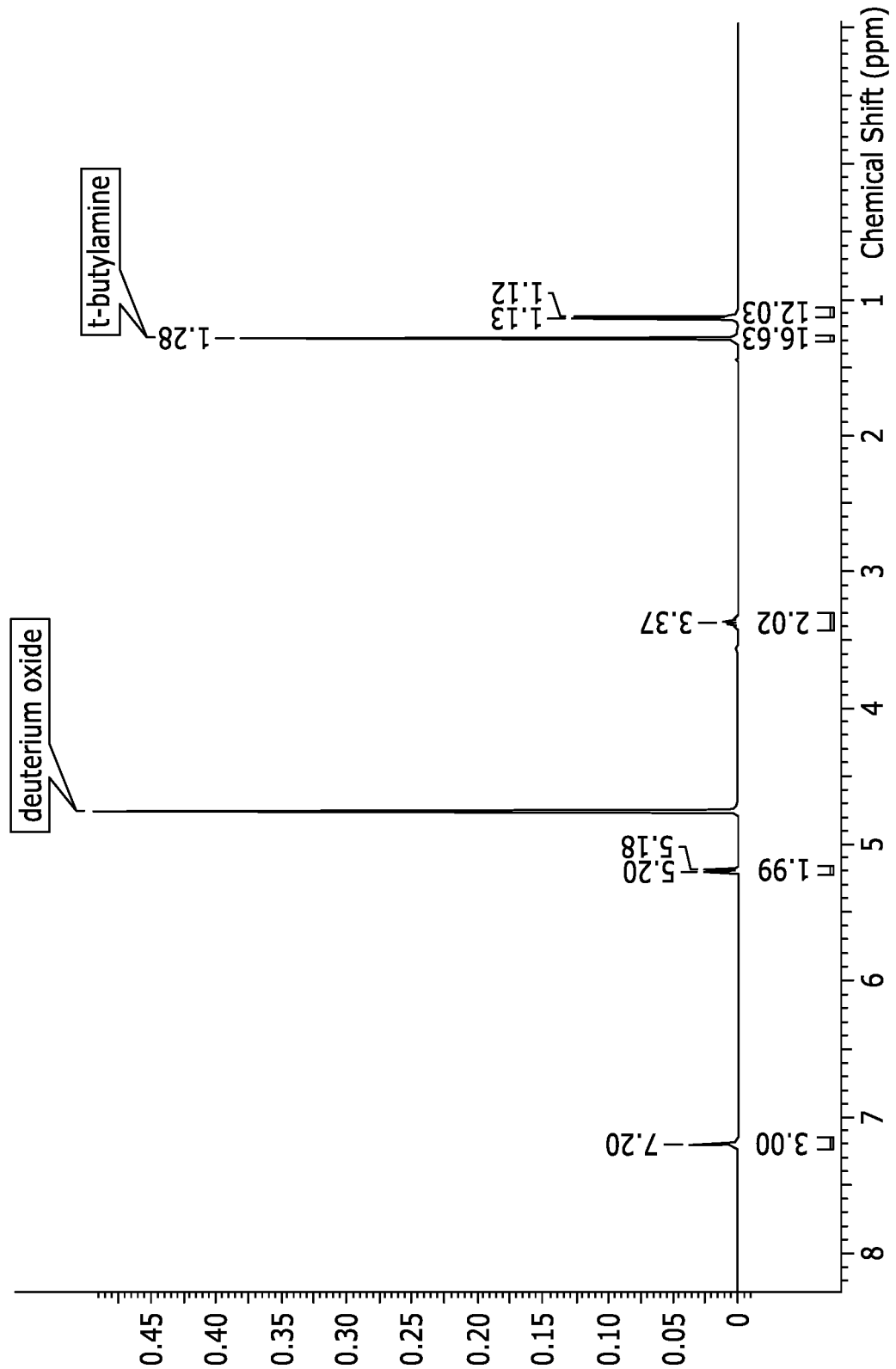
FIG. 9 shows a nuclear magnetic resonance (NMR) spectrum of a t-butylamine salt of fospropofol.

The t-butylamine salt of fospropofol can be characterized by an NMR spectrum substantially as shown in FIG. 9.

In some embodiments, the pharmaceutically acceptable salt of fospropofol is the ethylene diamine salt.

Figure 10:
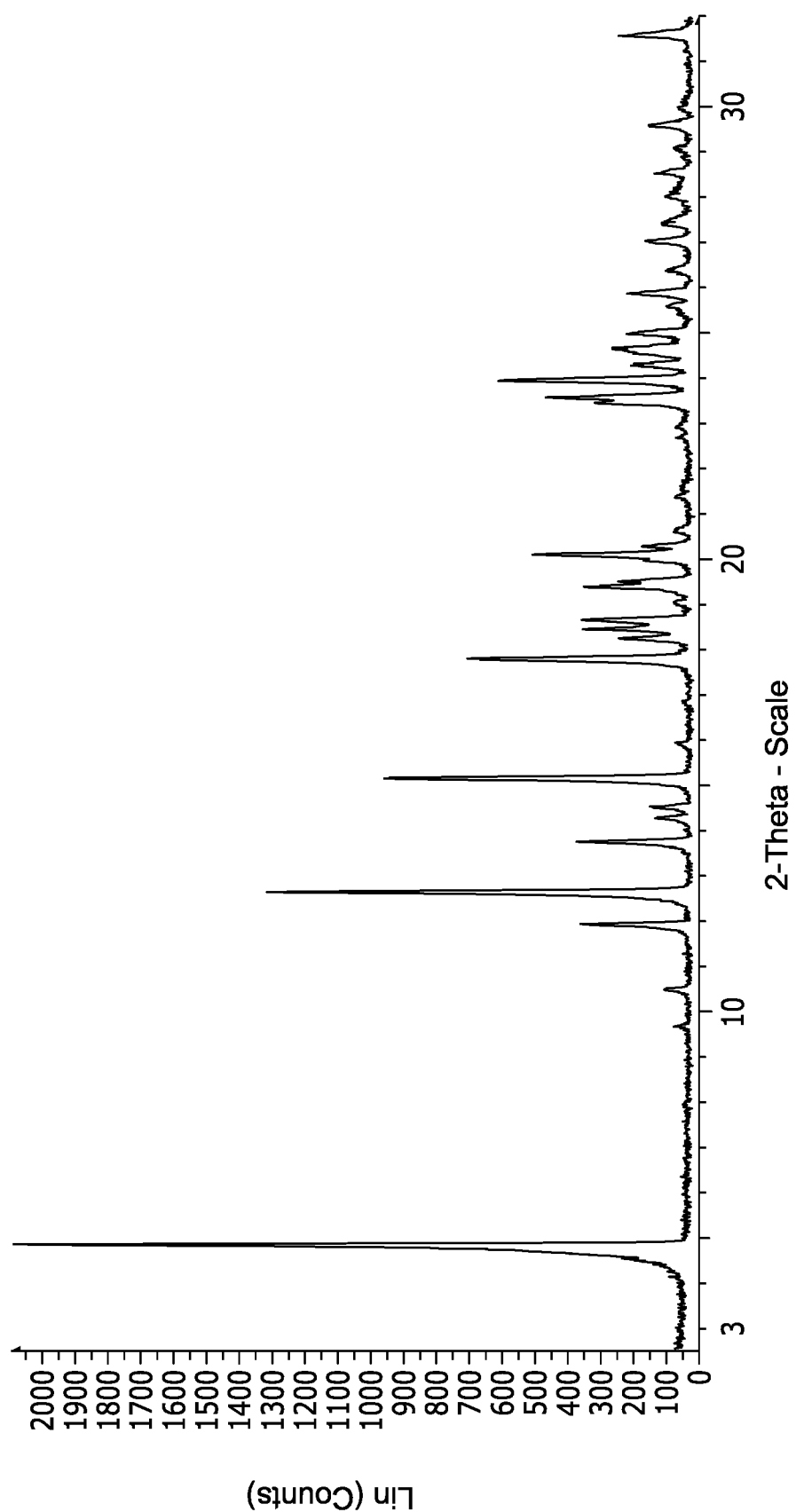
FIG. 10 shows an X-ray powder diffractogram (XRPD) of an ethylene diamine salt of fospropofol.

In some embodiments, the ethylene diamine salt of fospropofol has an XRPD substantially as shown in FIG. 10. The XRPD of the ethylene diamine salt of fospropofol shown in FIG. 10 comprises reflection angles (degrees 2-theta±0.2 degrees 2-theta), and relative intensities as shown in Table 4:

TABLE 4

XRPD Data for ethylene diamine salt of Fospropofol

| Angle (degrees 2-theta ± 0.2 degrees 2-theta) | Relative Intensity |
|---|---|
| 4.8 | 100.0 |
| 10.5 | 5.4 |
| 11.9 | 17.4 |
| 12.6 | 63.1 |
| 13.7 | 18.2 |
| 14.3 | 6.6 |
| 14.5 | 7.4 |
| 15.1 | 45.8 |
| 17.8 | 34.0 |
| 18.2 | 11.9 |
| 18.4 | 17.1 |
| 18.6 | 17.3 |
| 19.4 | 16.8 |
| 19.5 | 12.0 |
| 20.1 | 24.4 |
| 20.3 | 8.3 |
| 23.4 | 15.1 |
| 23.6 | 22.5 |
| 23.9 | 29.5 |
| 24.3 | 10.2 |
| 24.7 | 12.8 |
| 25.0 | 10.6 |

TABLE 4-continued

XRPD Data for ethylene diamine salt of Fospropofol

| Angle (degrees 2-theta ± 0.2 degrees 2-theta) | Relative Intensity |
| --- | --- |
| 25.6 | 4.9 |
| 25.9 | 10.6 |
| 26.4 | 4.9 |
| 27.0 | 8.0 |
| 27.4 | 5.6 |
| 28.0 | 5.2 |
| 28.5 | 6.5 |
| 29.6 | 7.4 |
| 31.6 | 11.6 |

In some embodiments of the present disclosure, the ethylene diamine salt of fospropofol is characterized by an XRPD pattern comprising a peak at one of the angles listed in Table 4. In other aspects, the ethylene diamine salt of fospropofol is characterized by an XRPD pattern comprising more than one peak at one of the angles listed in Table 4 above. In other aspects, the ethylene diamine salt of fospropofol is characterized by an XRPD pattern comprising two peaks selected from the angles listed in Table 4 above. In other aspects, the ethylene diamine salt of fospropofol is characterized by an XRPD pattern comprising three peaks selected from the angles listed in Table 4 above. In other aspects, the ethylene diamine salt of fospropofol is characterized by an XRPD pattern comprising four peaks selected from the angles listed in Table 4 above. In other aspects, the ethylene diamine salt of fospropofol is characterized by an XRPD pattern comprising five peaks selected from the angles listed in Table 4 above. In other aspects, the ethylene diamine salt of fospropofol is characterized by an XRPD pattern comprising six peaks selected from the angles listed in Table 4 above. In other aspects, the ethylene diamine salt of fospropofol is characterized by an XRPD pattern comprising seven peaks selected from the angles listed in Table 4 above. In other aspects, the ethylene diamine salt of fospropofol is characterized by an XRPD pattern comprising eight peaks selected from the angles listed in Table 4 above. In other aspects, the ethylene diamine salt of fospropofol is characterized by an XRPD pattern comprising nine peaks selected from the angles listed in Table 4 above. In other aspects, the ethylene diamine salt of fospropofol is characterized by an XRPD pattern comprising ten peaks selected from the angles listed in Table 4 above. In other aspects, the ethylene diamine salt of fospropofol is characterized by an XRPD pattern comprising more than ten peaks selected from the angles listed in Table 4 above.

In some embodiments, the ethylene diamine salt of fospropofol is characterized by an XRPD pattern comprising a peak at 12.6 degrees±0.2 degrees 2-theta. In other embodiments, the ethylene diamine salt of fospropofol is characterized by an XRPD pattern comprising peaks at 11.9, 12.6, and 13.7 degrees±0.2 degrees 2-theta. In other embodiments, the ethylene diamine salt of fospropofol is characterized by an XRPD pattern comprising peaks at 11.9, 12.6, 13.7, 15.1, 17.8, and 20.1 degrees±0.2 degree 2-theta. In yet other embodiments, the ethylene diamine salt of fospropofol is characterized by an XRPD pattern comprising peaks at 11.9, 12.6, 13.7, 15.1, 17.8, 20.1, 23.6, and 23.9 degrees±0.2 degree 2-theta.

In some embodiments of the present disclosure, the ethylene diamine salt of fospropofol is characterized by an XRPD pattern comprising peaks at three or more of 11.9, 12.6, 13.7, 15.1, 17.8, 20.1, 23.6, and 23.9 degrees±0.2 degrees 2-theta. In some embodiments of the present disclosure, the ethylene diamine salt of fospropofol is characterized by an XRPD pattern comprising peaks at four or more of 11.9, 12.6, 13.7, 15.1, 17.8, 20.1, 23.6, and 23.9 degrees±0.2 degrees 2-theta. In some embodiments of the present disclosure, the ethylene diamine salt of fospropofol is characterized by an XRPD pattern comprising peaks at five or more of 11.9, 12.6, 13.7, 15.1, 17.8, 20.1, 23.6, and 23.9 degrees±0.2 degrees 2-theta. In some embodiments of the present disclosure, the ethylene diamine salt of fospropofol is characterized by an XRPD pattern comprising peaks at six or more of 11.9, 12.6, 13.7, 15.1, 17.8, 20.1, 23.6, and 23.9 degrees±0.2 degrees 2-theta. In some embodiments of the present disclosure, the ethylene diamine salt of fospropofol is characterized by an XRPD pattern comprising peaks at seven or more of 11.9, 12.6, 13.7, 15.1, 17.8, 20.1, 23.6, and 23.9 degrees±0.2 degrees 2-theta.

Figure 11:
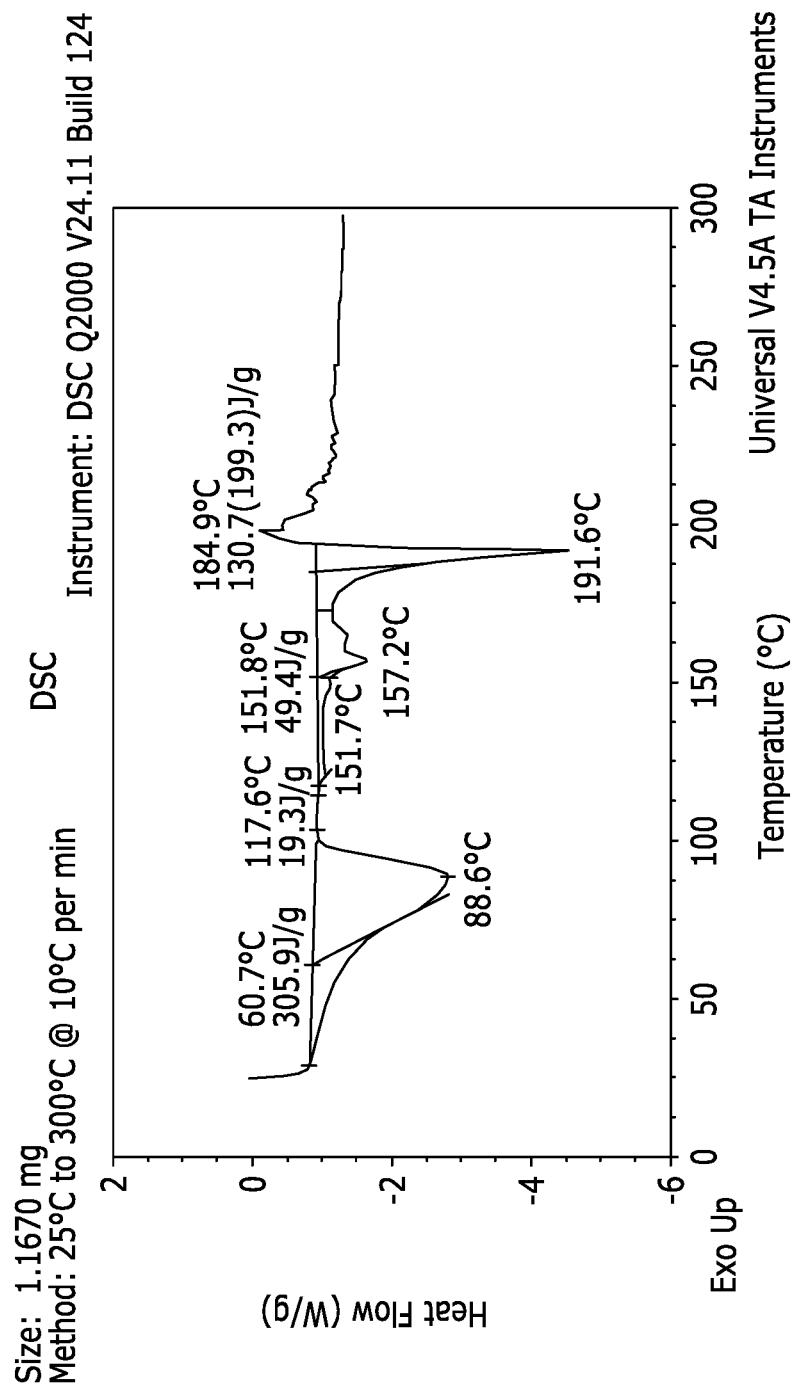
FIG. 11 shows a differential scanning calorimetry (DSC) profile of an ethylene diamine salt of fospropofol.

The ethylene diamine salt of fospropofol can be characterized by a DSC thermogram substantially as shown in FIG. 11. As FIG. 11 shows, the ethylene diamine salt of fospropofol produced endothermic peaks at about 88.6° C. and 191.6° C. when heated at a rate of 10° C./min. In some embodiments of the present disclosure, the ethylene diamine salt of fospropofol is characterized by a DSC thermogram comprising an endothermic peak at about 89° C., or at about 192° C.

In some embodiments of the present disclosure, the ethylene diamine salt of fospropofol is characterized by an XRPD pattern comprising peaks at one or more of 11.9, 12.6, 13.7, 15.1, 17.8, 20.1, 23.6, and 23.9 degrees±0.2 degrees 2-theta, and a DSC thermogram comprising an endothermic peak at about 89° C., or at about 192° C., when heated at a rate of 10° C./min.

Figure 12:
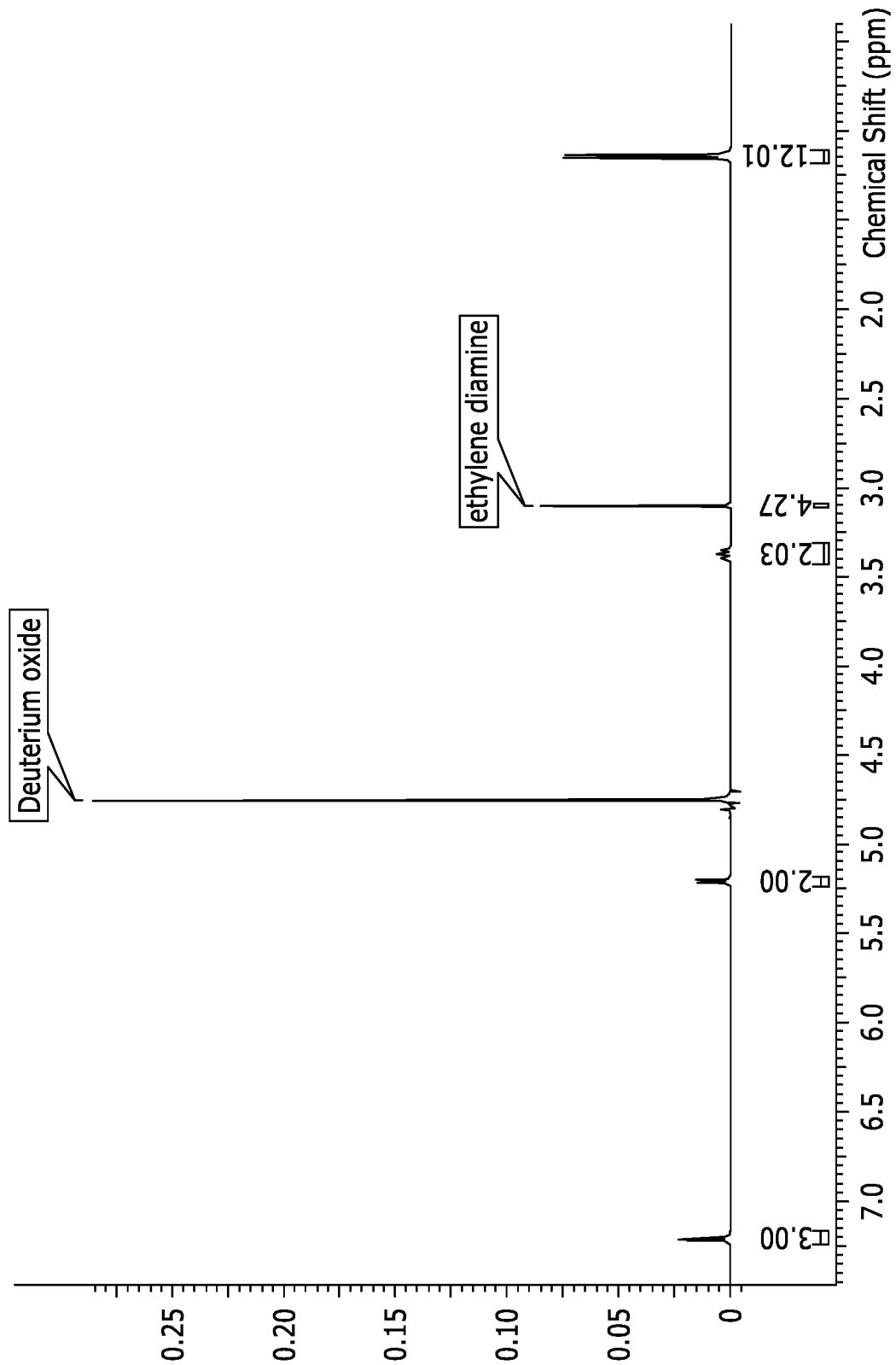
FIG. 12 shows a nuclear magnetic resonance (NMR) spectrum of an ethylene diamine salt of fospropofol.

The ethylene diamine salt of fospropofol can be characterized by an NMR spectrum substantially as shown in FIG. 12.

In some embodiments, the pharmaceutically acceptable salt of fospropofol is the benzathine (i.e., $N^1,N^2$-dibenzylethane-1,2-diamine) salt.

Figure 13:
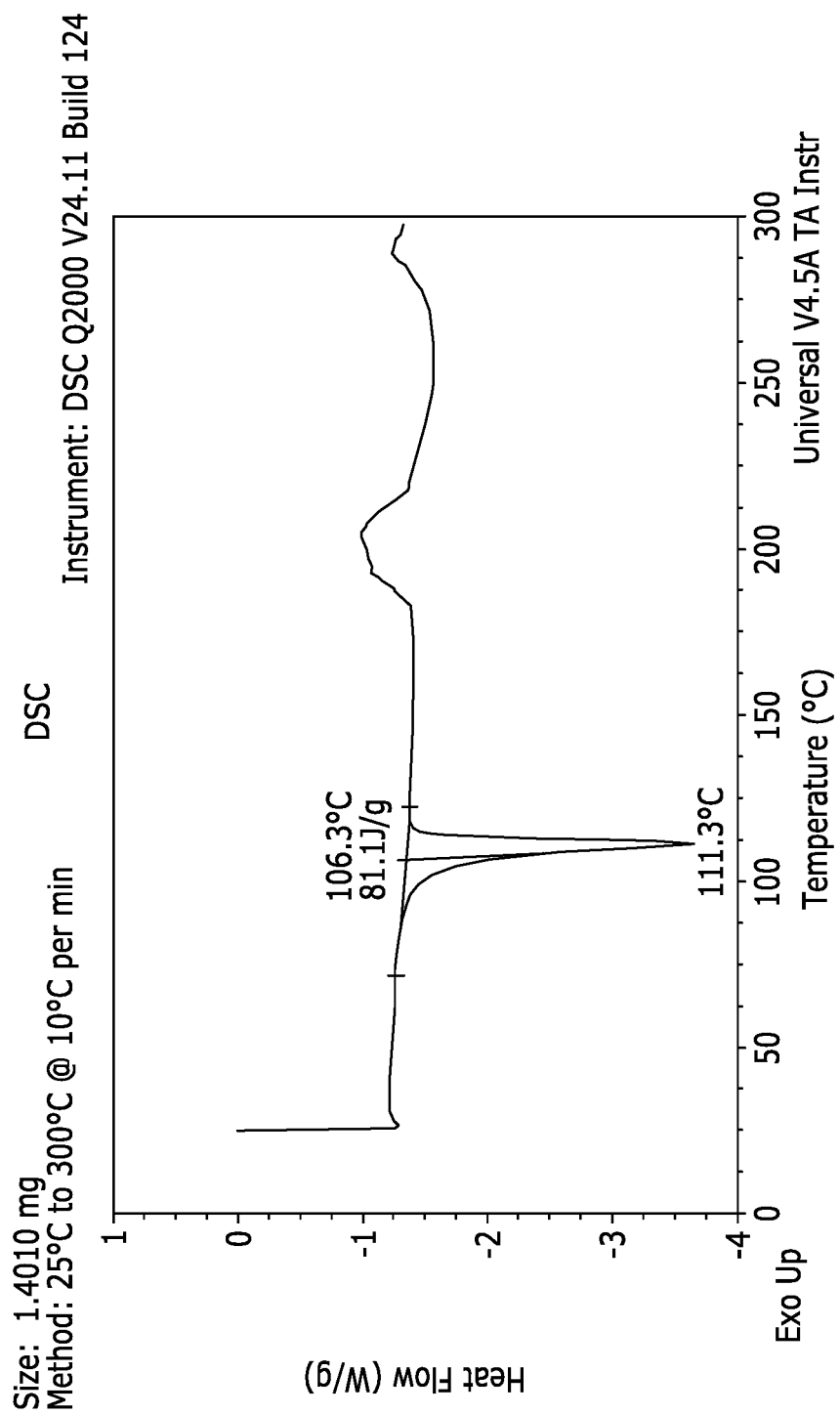
FIG. 13 shows a differential scanning calorimetry (DSC) profile of the benzathine salt of fospropofol.

The benzathine salt of fospropofol can be characterized by a DSC thermogram substantially as shown in FIG. 13. As FIG. 13 shows, the benzathine salt of fospropofol produced endothermic peak at about 111.3° C. when heated at a rate of 10° C./min. In some embodiments of the present disclosure, the benzathine salt of fospropofol is characterized by a DSC thermogram comprising an endothermic peak at about 111° C.

Figure 14:
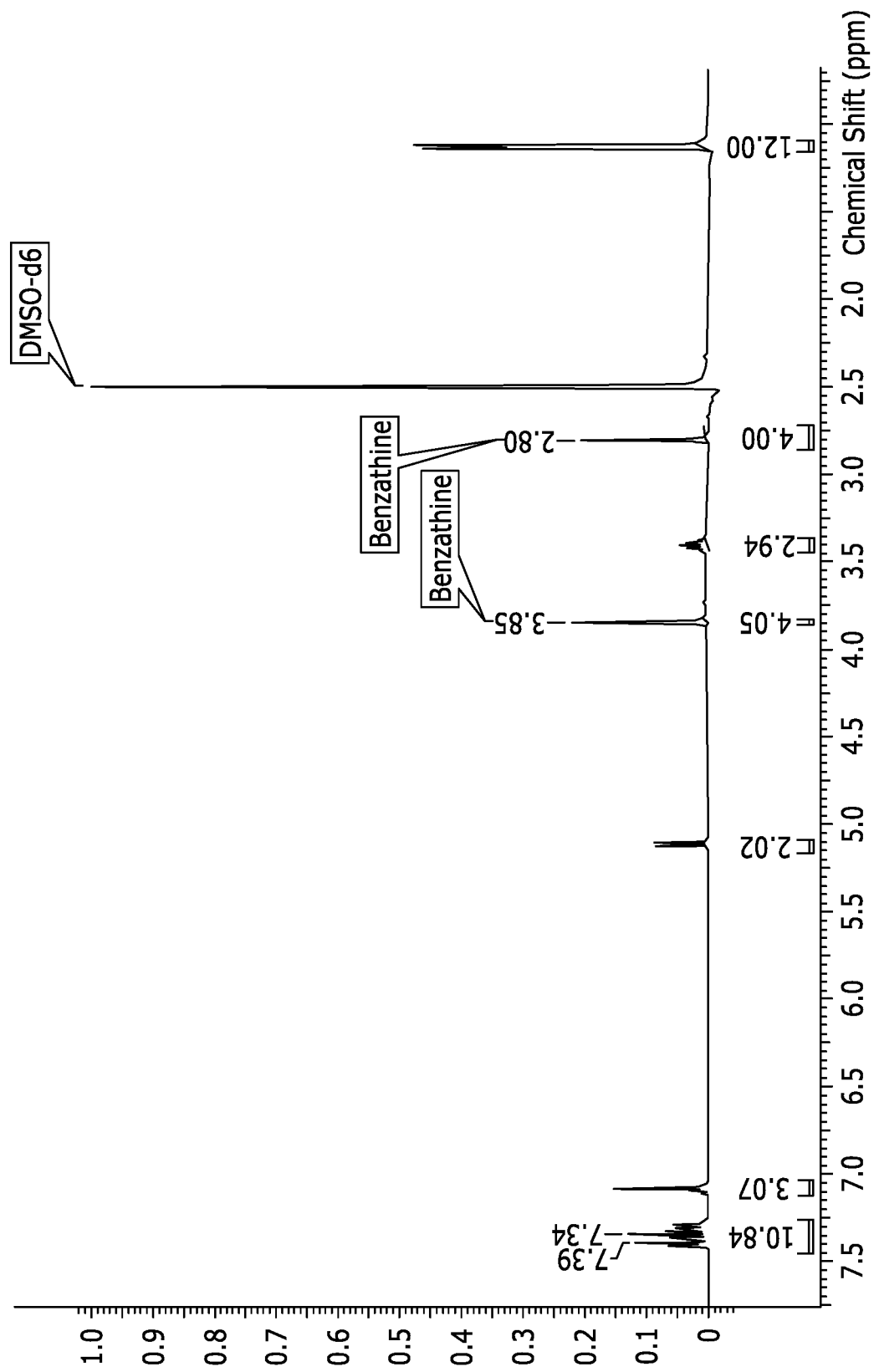
FIG. 14 shows a nuclear magnetic resonance (NMR) spectrum of the benzathine salt of fospropofol.

The benzathine salt of fospropofol can be characterized by an NMR spectrum substantially as shown in FIG. 14.

In some embodiments, the pharmaceutically acceptable salt of fospropofol is the piperazine salt.

Figure 15:
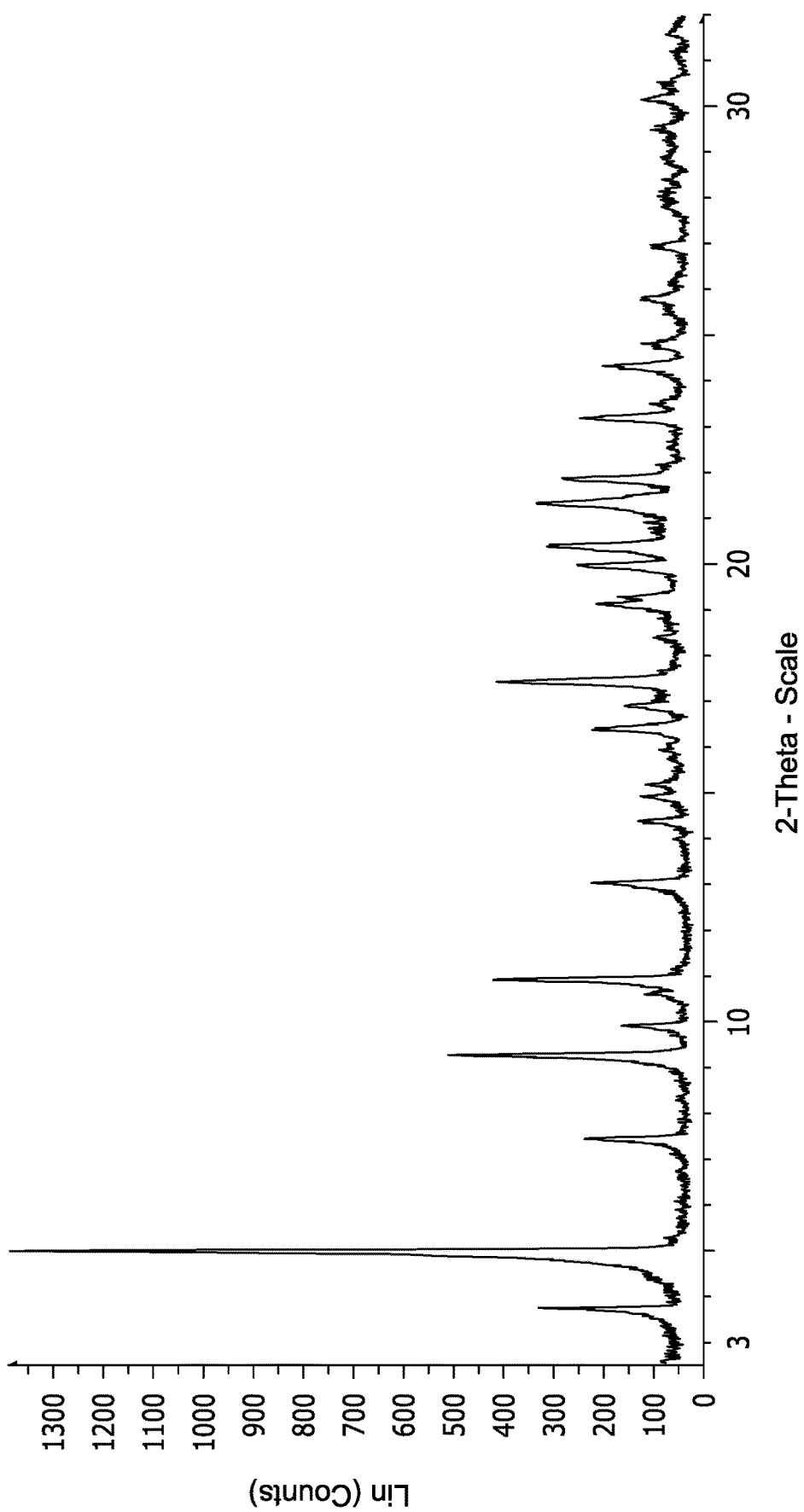
FIG. 15 shows an X-ray powder diffractogram (XRPD) of a piperazine salt of fospropofol.

In some embodiments, the piperazine salt of fospropofol has an XRPD substantially as shown in FIG. 15. The XRPD of the piperazine salt of fospropofol shown in FIG. 15 comprises reflection angles (degrees 2-theta±0.2 degrees 2-theta), and relative intensities as shown in Table 6:

TABLE 6

XRPD Data for piperazine salt of Fospropofol

| Angle (degrees 2-theta ± 0.2 degrees 2-theta) | Relative Intensity |
| --- | --- |
| 3.7 | 23.9 |
| 4.9 | 100.0 |
| 7.4 | 17.3 |
| 9.2 | 36.8 |

TABLE 6-continued

XRPD Data for piperazine salt of Fospropofol

| Angle (degrees 2-theta ± 0.2 degrees 2-theta) | Relative Intensity |
|---|---|
| 9.9 | 12.2 |
| 10.6 | 8.5 |
| 10.9 | 30.4 |
| 13.0 | 16.3 |
| 14.4 | 9.6 |
| 14.9 | 9.2 |
| 15.2 | 8.3 |
| 16.3 | 16.2 |
| 16.9 | 11.6 |
| 17.4 | 30.0 |
| 19.1 | 15.4 |
| 19.3 | 12.2 |
| 20.0 | 18.2 |
| 20.4 | 22.5 |
| 21.3 | 24.3 |
| 21.9 | 20.3 |
| 23.2 | 18.0 |
| 24.3 | 14.3 |
| 24.8 | 9.1 |
| 25.8 | 8.8 |
| 26.9 | 7.6 |

In some embodiments of the present disclosure, the piperazine salt of fospropofol is characterized by an XRPD pattern comprising a peak at one of the angles listed in Table 6. In other aspects, the piperazine salt of fospropofol is characterized by an XRPD pattern comprising more than one peak at one of the angles listed in Table 6 above. In other aspects, the piperazine salt of fospropofol is characterized by an XRPD pattern comprising two peaks selected from the angles listed in Table 6 above. In other aspects, the piperazine salt of fospropofol is characterized by an XRPD pattern comprising three peaks selected from the angles listed in Table 6 above. In other aspects, the piperazine salt of fospropofol is characterized by an XRPD pattern comprising four peaks selected from the angles listed in Table 6 above. In other aspects, the piperazine salt of fospropofol is characterized by an XRPD pattern comprising five peaks selected from the angles listed in Table 6 above. In other aspects, the piperazine salt of fospropofol is characterized by an XRPD pattern comprising six peaks selected from the angles listed in Table 6 above. In other aspects, the piperazine salt of fospropofol is characterized by an XRPD pattern comprising seven peaks selected from the angles listed in Table 6 above. In other aspects, the piperazine salt of fospropofol is characterized by an XRPD pattern comprising eight peaks selected from the angles listed in Table 6 above. In other aspects, the piperazine salt of fospropofol is characterized by an XRPD pattern comprising nine peaks selected from the angles listed in Table 6 above. In other aspects, the piperazine salt of fospropofol is characterized by an XRPD pattern comprising ten peaks selected from the angles listed in Table 6 above. In other aspects, the piperazine salt of fospropofol is characterized by an XRPD pattern comprising more than ten peaks selected from the angles listed in Table 6 above.

In some embodiments, the piperazine salt of fospropofol is characterized by an XRPD pattern comprising a peak at 4.9, 9.2, and 10.9 degrees±0.2 degrees 2-theta. In other embodiments, the piperazine salt of fospropofol is characterized by an XRPD pattern comprising peaks at 4.9, 9.2, 10.9, 13.0, 16.3, and 17.4 degrees±0.2 degrees 2-theta. In other embodiments, the piperazine salt of fospropofol is characterized by an XRPD pattern comprising peaks at 20.0, 20.4, 21.3, 21.9, 23.2, and 24.3 degrees±0.2 degree 2-theta. In yet other embodiments, the piperazine salt of fospropofol is characterized by an XRPD pattern comprising peaks at 4.9, 9.2, 10.9, 13.0, 16.3, 17.4, 20.0, 20.4, 21.3, 21.9, 23.2, and 24.3 degrees±0.2 degree 2-theta.

In some embodiments of the present disclosure, the piperazine salt of fospropofol is characterized by an XRPD pattern comprising peaks at three or more of 4.9, 9.2, 10.9, 13.0, 16.3, 17.4, 20.0, 20.4, 21.3, 21.9, 23.2, and 24.3 degrees±0.2 degrees 2-theta. In some embodiments of the present disclosure, the piperazine salt of fospropofol is characterized by an XRPD pattern comprising peaks at four or more of 4.9, 9.2, 10.9, 13.0, 16.3, 17.4, 20.0, 20.4, 21.3, 21.9, 23.2, and 24.3 degrees±0.2 degrees 2-theta. In some embodiments of the present disclosure, the piperazine salt of fospropofol is characterized by an XRPD pattern comprising peaks at five or more of 4.9, 9.2, 10.9, 13.0, 16.3, 17.4, 20.0, 20.4, 21.3, 21.9, 23.2, and 24.3 degrees±0.2 degrees 2-theta. In some embodiments of the present disclosure, the piperazine salt of fospropofol is characterized by an XRPD pattern comprising peaks at six or more of 4.9, 9.2, 10.9, 13.0, 16.3, 17.4, 20.0, 20.4, 21.3, 21.9, 23.2, and 24.3 degrees±0.2 degrees 2-theta. In some embodiments of the present disclosure, the piperazine salt of fospropofol is characterized by an XRPD pattern comprising peaks at seven or more of 4.9, 9.2, 10.9, 13.0, 16.3, 17.4, 20.0, 20.4, 21.3, 21.9, 23.2, and 24.3 degrees±0.2 degrees 2-theta.

Figure 16:
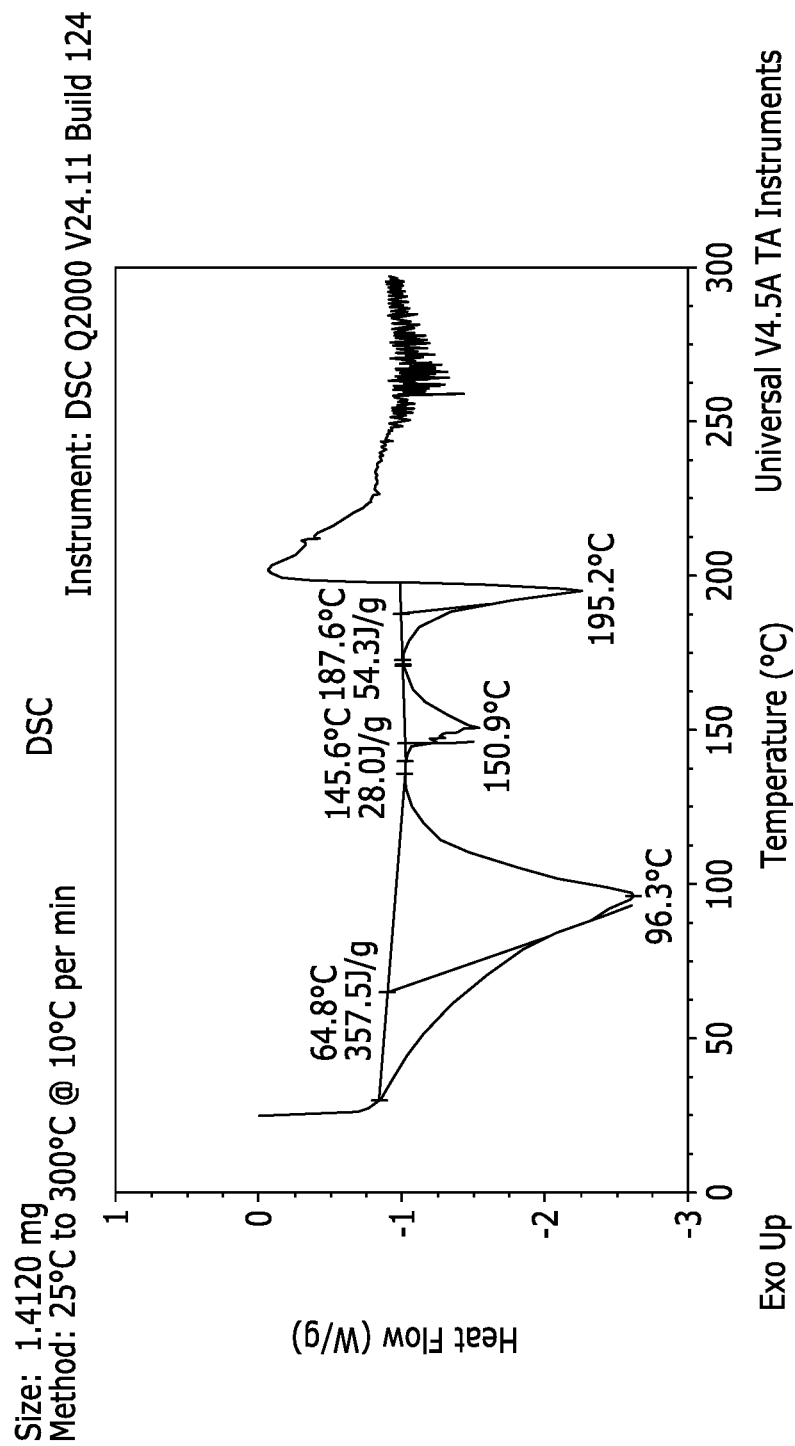
FIG. 16 shows a differential scanning calorimetry (DSC) profile of a piperazine salt of fospropofol.

The piperazine salt of fospropofol can be characterized by a DSC thermogram substantially as shown in FIG. 16. As FIG. 16 shows, the piperazine salt of fospropofol produced endothermic peak at 96.3° C., 150.9° C., and 195.2° C. when heated at a rate of 10° C./min. In some embodiments of the present disclosure, the piperazine salt of fospropofol is characterized by a DSC thermogram comprising an endothermic peak at about 96° C., 151° C., or 195° C. when heated at a rate of 10° C./min.

In some embodiments of the present disclosure, the piperazine salt of fospropofol is characterized by an XRPD pattern comprising peaks at one or more of 4.9, 9.2, 10.9, 13.0, 16.3, 17.4, 20.0, 20.4, 21.3, 21.9, 23.2, and 24.3 degrees±0.2 degrees 2-theta, and a DSC thermogram comprising an endothermic peak at about 96° C., 151° C., or 195° C. when heated at a rate of 10° C./min.

Figure 17:
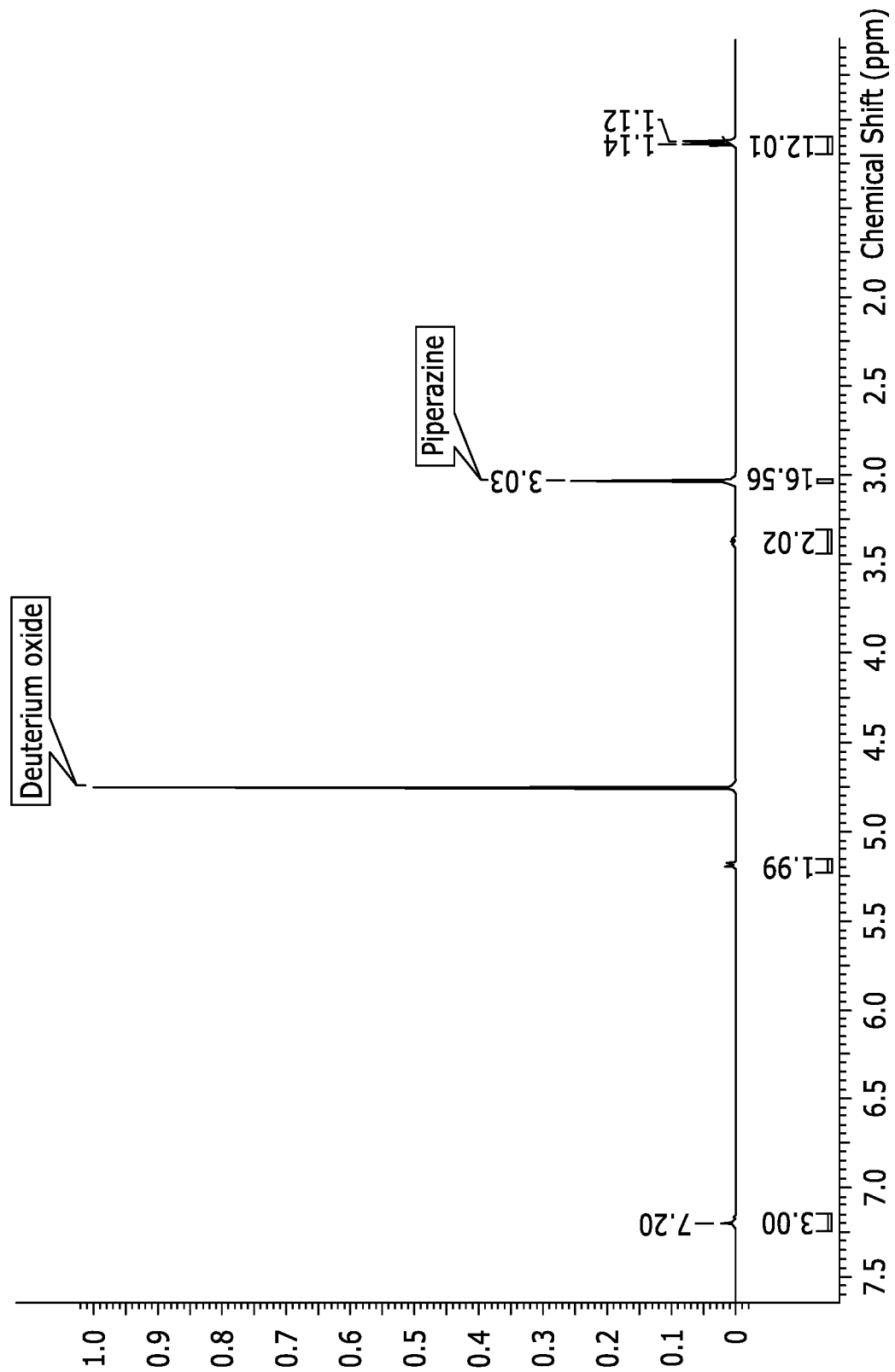
FIG. 17 shows a nuclear magnetic resonance (NMR) spectrum of a piperazine salt of fospropofol.

The piperazine salt of fospropofol can be characterized by an NMR spectrum substantially as shown in FIG. 17.

In some embodiments, the pharmaceutically acceptable salt of fospropofol is the ethanolamine salt.

Figure 18:
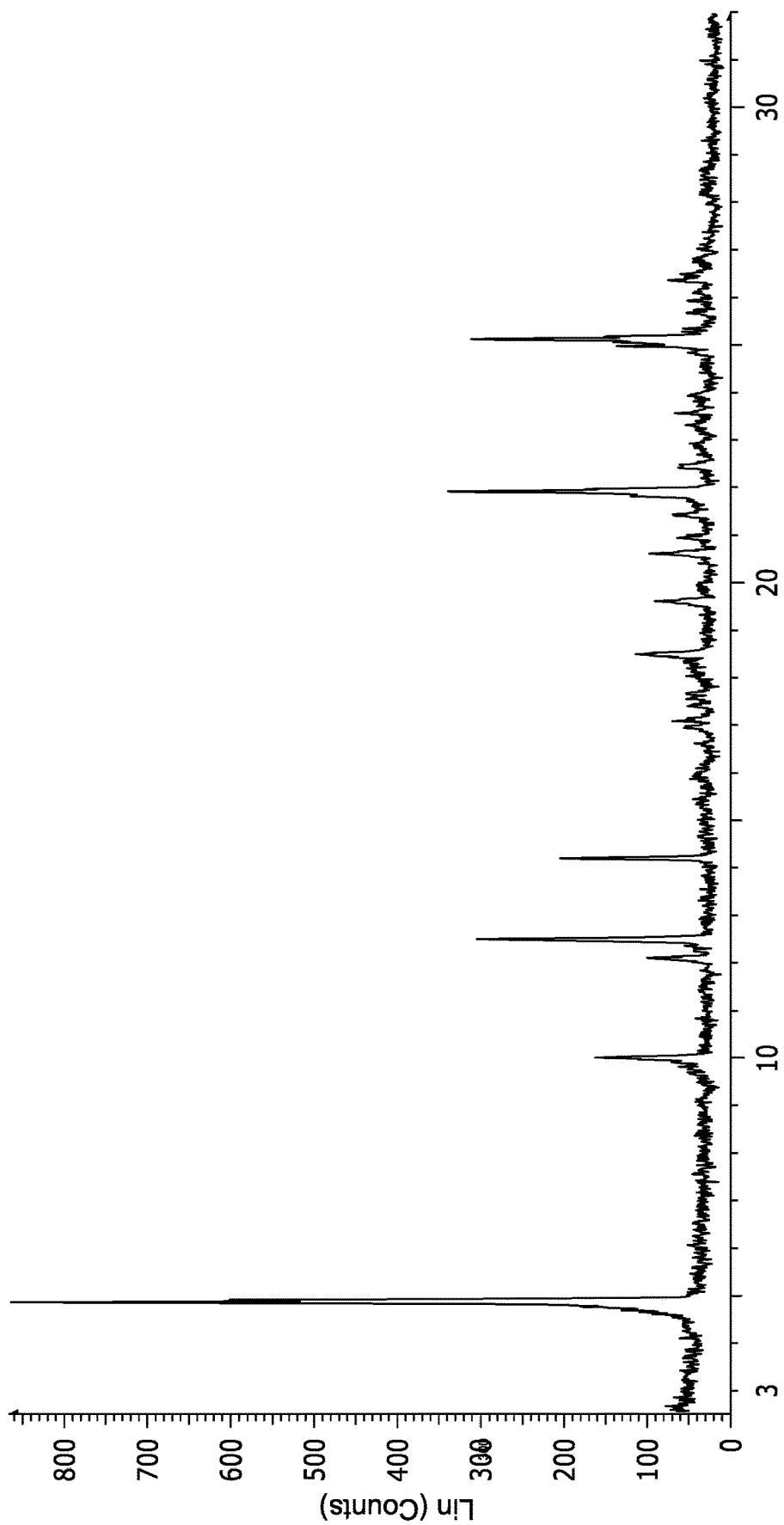
FIG. 18 shows an X-ray powder diffractogram (XRPD) of an ethanolamine salt of fospropofol (Form II).

In some embodiments, the ethanolamine salt of fospropofol (Form II) has an XRPD substantially as shown in FIG. 18. The XRPD of the Form II ethanolamine salt of fospropofol shown in FIG. 18 comprises reflection angles (degrees 2-theta±0.2 degrees 2-theta), and relative intensities as shown in Table 7A:

TABLE 7A

XRPD Data for Form II ethanolamine salt of Fospropofol

| Angle (degrees 2-theta ± 0.2 degrees 2-theta) | Relative Intensity |
|---|---|
| 4.8 | 100.0 |
| 10.0 | 19.0 |
| 12.1 | 11.9 |
| 12.5 | 35.5 |
| 14.2 | 24.1 |
| 18.5 | 13.1 |
| 19.6 | 10.6 |

TABLE 7A-continued

XRPD Data for Form II ethanolamine salt of Fospropofol

| Angle (degrees 2-theta ± 0.2 degrees 2-theta) | Relative Intensity |
|---|---|
| 20.6 | 11.6 |
| 21.9 | 39.5 |
| 25.1 | 35.6 |

In some embodiments of the present disclosure, the ethanolamine salt of fospropofol is characterized by an XRPD pattern comprising a peak at one of the angles listed in Table 7A. In other aspects, the ethanolamine salt of fospropofol is characterized by an XRPD pattern comprising more than one peak at one of the angles listed in Table 7A above. In other aspects, the ethanolamine salt of fospropofol is characterized by an XRPD pattern comprising two peaks selected from the angles listed in Table 7A above. In other aspects, the ethanolamine salt of fospropofol is characterized by an XRPD pattern comprising three peaks selected from the angles listed in Table 7A above. In other aspects, the ethanolamine salt of fospropofol is characterized by an XRPD pattern comprising four peaks selected from the angles listed in Table 7A above. In other aspects, the ethanolamine salt of fospropofol is characterized by an XRPD pattern comprising five peaks selected from the angles listed in Table 7A above. In other aspects, the ethanolamine salt of fospropofol is characterized by an XRPD pattern comprising six peaks selected from the angles listed in Table 7A above. In other aspects, the ethanolamine salt of fospropofol is characterized by an XRPD pattern comprising seven peaks selected from the angles listed in Table 7A above. In other aspects, the ethanolamine salt of fospropofol is characterized by an XRPD pattern comprising eight peaks selected from the angles listed in Table 7A above. In other aspects, the ethanolamine salt of fospropofol is characterized by an XRPD pattern comprising nine peaks selected from the angles listed in Table 7A above. In other aspects, the ethanolamine salt of fospropofol is characterized by an XRPD pattern comprising ten peaks selected from the angles listed in Table 7A above. In other aspects, the ethanolamine salt of fospropofol is characterized by an XRPD pattern comprising more than ten peaks selected from the angles listed in Table 7A above.

In some embodiments, the ethanolamine salt of fospropofol is characterized by an XRPD pattern comprising a peaks at 12.5, and 14.2 degrees degrees±0.2 degrees 2-theta. In other embodiments, the ethanolamine salt of fospropofol is characterized by an XRPD pattern comprising peaks at 12.5, 14.2, and 21.9 degrees±0.2 degrees 2-theta. In other embodiments, the ethanolamine salt of fospropofol is characterized by an XRPD pattern comprising peaks at 12.5, 14.2, 21.9, and 25.1 degrees±0.2 degree 2-theta. In yet other embodiments, the ethanolamine salt of fospropofol is characterized by an XRPD pattern comprising peaks at 4.8, 12.5, 14.2, 21.9, and 25.1 degrees±0.2 degree 2-theta.

In some embodiments of the present disclosure, the ethanolamine salt of fospropofol is characterized by an XRPD pattern comprising peaks at two or more of 4.8, 12.5, 14.2, 21.9, and 25.1 degrees degrees±0.2 degrees 2-theta. In some embodiments of the present disclosure, the ethanolamine salt of fospropofol is characterized by an XRPD pattern comprising peaks at three or more of 4.8, 12.5, 14.2, 21.9, and 25.1 degrees±0.2 degrees 2-theta. In some embodiments of the present disclosure, the ethanolamine salt of fospropofol is characterized by an XRPD pattern comprising peaks at four or more of 4.8, 12.5, 14.2, 21.9, and 25.1 degrees±0.2 degrees 2-theta.

Figure 19:
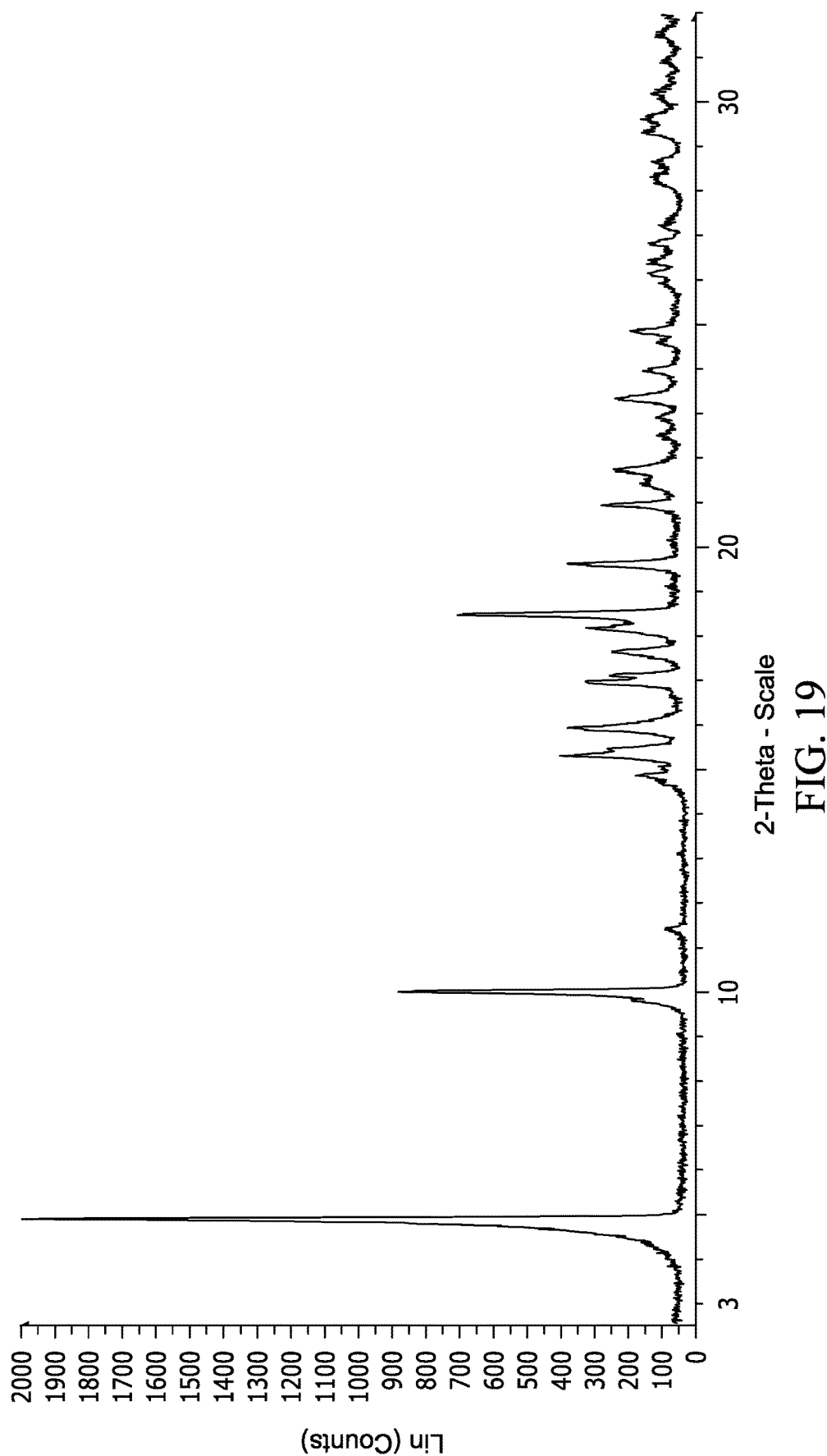
FIG. 19 shows an X-ray powder diffractogram (XRPD) of an ethanolamine salt of fospropofol (Form I).

In other embodiments, the ethanolamine salt of fospropofol (Form I) has an XRPD substantially as shown in FIG. 19. The XRPD of the Form I ethanolamine salt of fospropofol shown in FIG. 19 comprises reflection angles (degrees 2-theta±0.2 degrees 2-theta), and relative intensities as shown in Table 7:

TABLE 7

XRPD Data for Form I ethanolamine salt of Fospropofol

| Angle (degrees 2-theta ± 0.2 degrees 2-theta) | Relative Intensity |
|---|---|
| 4.8 | 100.0 |
| 10.0 | 44.4 |
| 11.4 | 4.9 |
| 14.8 | 9.0 |
| 15.3 | 20.1 |
| 15.5 | 13.0 |
| 15.9 | 19.0 |
| 17.0 | 16.0 |
| 17.1 | 12.7 |
| 17.6 | 12.5 |
| 18.2 | 16.5 |
| 18.5 | 35.5 |
| 19.6 | 19.3 |
| 20.9 | 14.2 |
| 21.4 | 8.0 |
| 21.7 | 12.2 |
| 22.5 | 6.0 |
| 22.9 | 6.2 |
| 23.3 | 12.3 |
| 24.0 | 7.7 |
| 24.6 | 5.7 |
| 24.9 | 9.6 |

In some embodiments of the present disclosure, the ethanolamine salt of fospropofol is characterized by an XRPD pattern comprising a peak at one of the angles listed in Table 7. In other aspects, the ethanolamine salt of fospropofol is characterized by an XRPD pattern comprising more than one peak at one of the angles listed in Table 7 above. In other aspects, the ethanolamine salt of fospropofol is characterized by an XRPD pattern comprising two peaks selected from the angles listed in Table 7 above. In other aspects, the ethanolamine salt of fospropofol is characterized by an XRPD pattern comprising three peaks selected from the angles listed in Table 7 above. In other aspects, the ethanolamine salt of fospropofol is characterized by an XRPD pattern comprising four peaks selected from the angles listed in Table 7 above. In other aspects, the ethanolamine salt of fospropofol is characterized by an XRPD pattern comprising five peaks selected from the angles listed in Table 7 above. In other aspects, the ethanolamine salt of fospropofol is characterized by an XRPD pattern comprising six peaks selected from the angles listed in Table 7 above. In other aspects, the ethanolamine salt of fospropofol is characterized by an XRPD pattern comprising seven peaks selected from the angles listed in Table 7 above. In other aspects, the ethanolamine salt of fospropofol is characterized by an XRPD pattern comprising eight peaks selected from the angles listed in Table 7 above. In other aspects, the ethanolamine salt of fospropofol is characterized by an XRPD pattern comprising nine peaks selected from the angles listed in Table 7 above. In other aspects, the ethanolamine salt of fospropofol is characterized by an XRPD pattern comprising ten peaks selected from the angles listed in Table 7 above. In other aspects, the ethanolamine salt of fospropofol is characterized by an XRPD pattern comprising more than ten peaks selected from the angles listed in Table 7 above.

In some embodiments, the ethanolamine salt of fospropofol is characterized by an XRPD pattern comprising a peak at 10.0 degrees±0.2 degrees 2-theta. In other embodiments, the ethanolamine salt of fospropofol is characterized by an XRPD pattern comprising peaks at 10.0, 18.5, 19.6, and 20.9 degrees±0.2 degrees 2-theta. In other embodiments, the ethanolamine salt of fospropofol is characterized by an XRPD pattern comprising peaks at 10.0, 17.0, 18.5, 19.6, and 20.9 degrees±0.2 degree 2-theta. In yet other embodiments, the ethanolamine salt of fospropofol is characterized by an XRPD pattern comprising peaks at 10.0, 15.3, 15.9, 17.0, 18.5, 19.6, and 20.9 degrees±0.2 degree 2-theta.

In some embodiments of the present disclosure, the ethanolamine salt of fospropofol is characterized by an XRPD pattern comprising peaks at two or more of 10.0, 15.3, 15.9, 17.0, 18.5, 19.6, and 20.9 degrees±0.2 degrees 2-theta. In some embodiments of the present disclosure, the ethanolamine salt of fospropofol is characterized by an XRPD pattern comprising peaks at three or more of 10.0, 15.3, 15.9, 17.0, 18.5, 19.6, and 20.9 degrees±0.2 degrees 2-theta. In some embodiments of the present disclosure, the ethanolamine salt of fospropofol is characterized by an XRPD pattern comprising peaks at four or more of 10.0, 15.3, 15.9, 17.0, 18.5, 19.6, and 20.9 degrees±0.2 degrees 2-theta. In some embodiments of the present disclosure, the ethanolamine salt of fospropofol is characterized by an XRPD pattern comprising peaks at five or more of 10.0, 15.3, 15.9, 17.0, 18.5, 19.6, and 20.9 degrees±0.2 degrees 2-theta.

Figure 20:
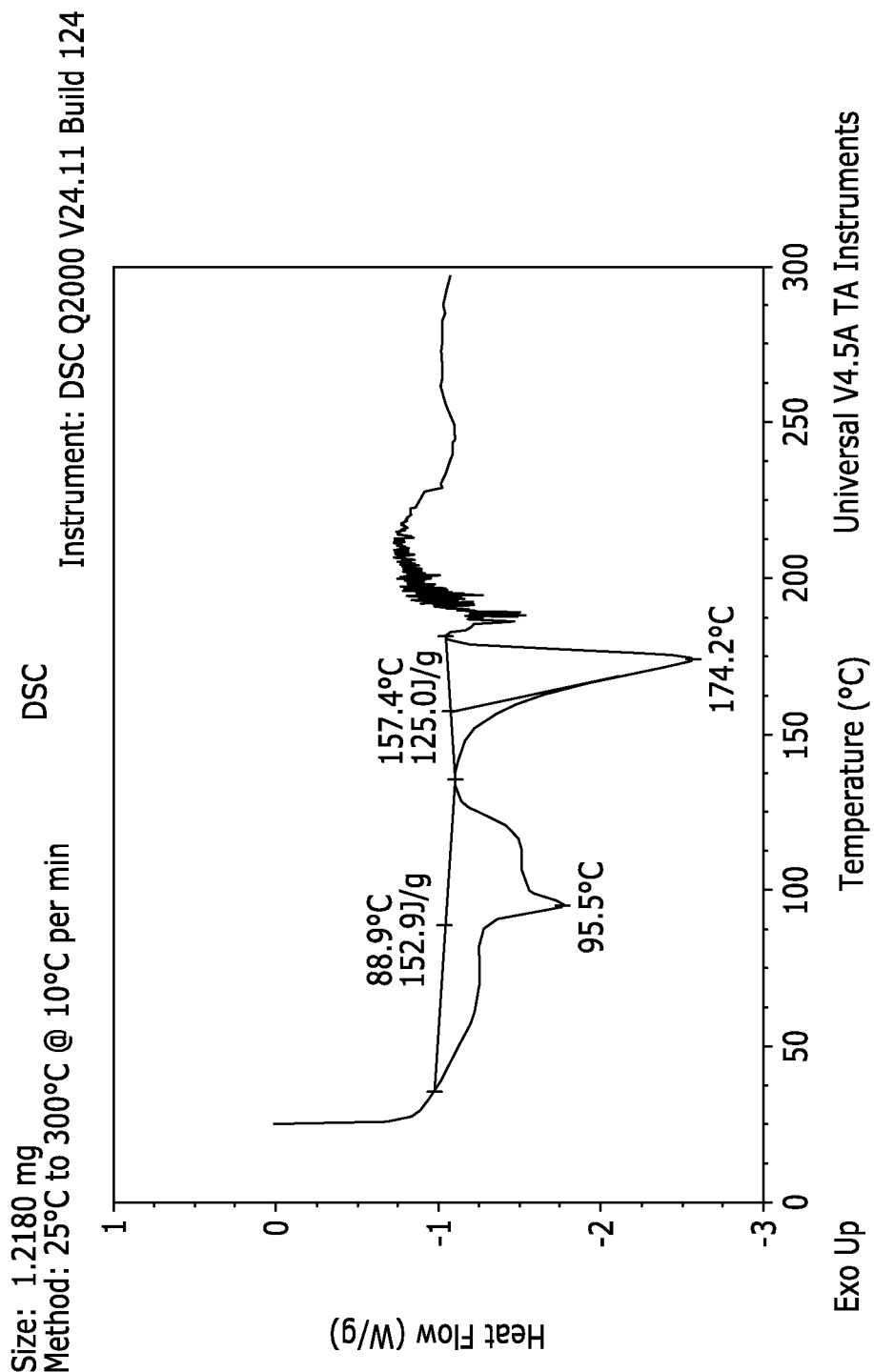
FIG. 20 shows a differential scanning calorimetry (DSC) profile of an ethanolamine salt of fospropofol (Form I).

The Form I ethanolamine salt of fospropofol can be characterized by a DSC thermogram substantially as shown in FIG. 20. As FIG. 20 shows, the ethanolamine salt of fospropofol produced endothermic peak at 95.5° C. and 174.2° C. when heated at a rate of 10° C./min. In some embodiments of the present disclosure, the ethanolamine salt of fospropofol is characterized by a DSC thermogram comprising an endothermic peak at about 96° C., or about 174° C. when heated at a rate of 10° C./min.

In some embodiments of the present disclosure, the Form I ethanolamine salt of fospropofol is characterized by an XRPD pattern comprising peaks at one or more of 10.0, 15.3, 15.9, 17.0, 18.5, 19.6, and 20.9 degrees±0.2 degrees 2-theta, and a DSC thermogram comprising an endothermic peak at about 96° C., or about 174° C. when heated at a rate of 10° C./min.

Figure 21:
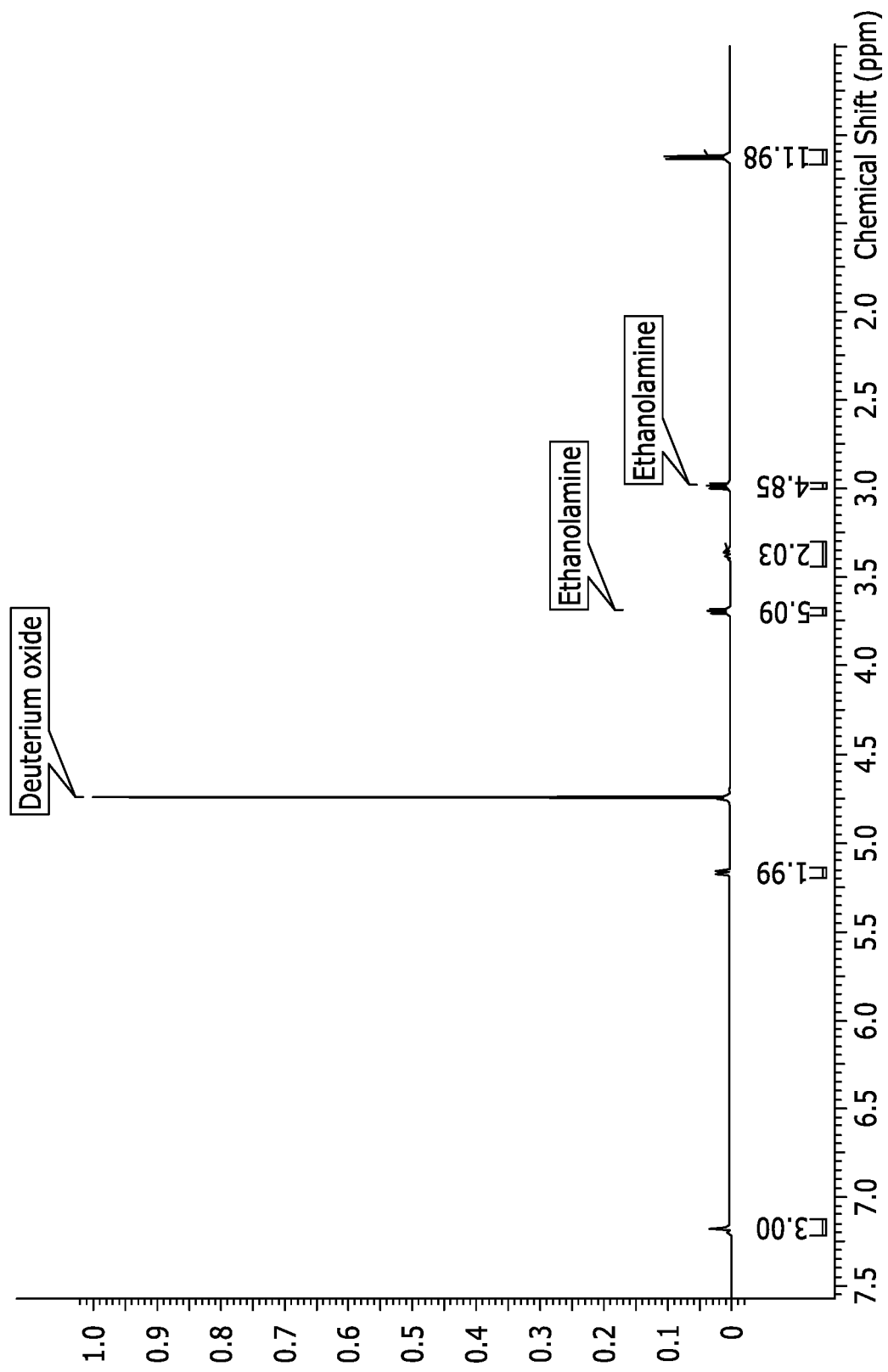
FIG. 21 shows a nuclear magnetic resonance (NMR) spectrum of an ethanolamine salt of fospropofol (Form I).

The Form I ethanolamine salt of fospropofol can be characterized by an NMR spectrum substantially as shown in FIG. 21.

In some embodiments, the pharmaceutically acceptable salt of fospropofol is the diethanolamine salt.

Figure 22:
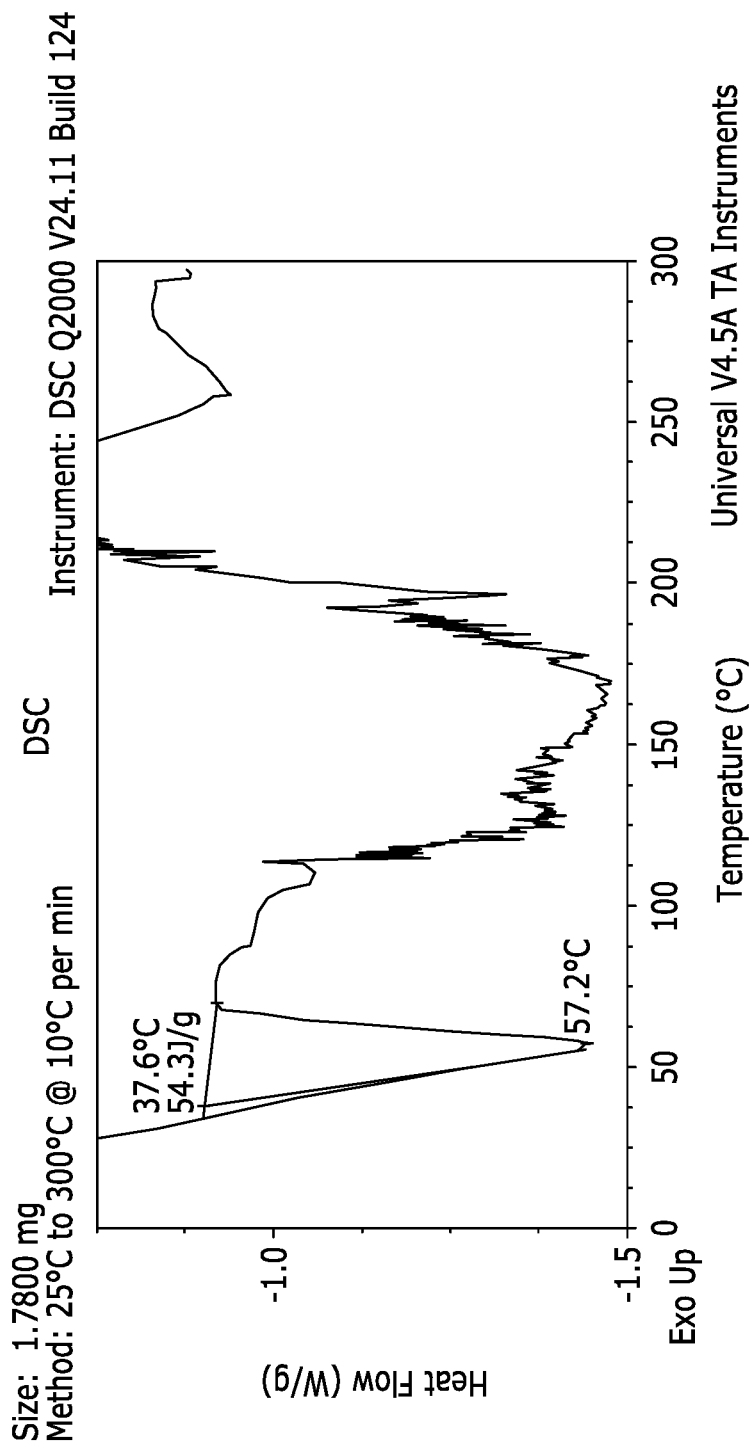
FIG. 22 shows differential scanning calorimetry (DSC) profile of a diethanolamine salt of fospropofol.

The diethanolamine salt of fospropofol can be characterized by a DSC thermogram substantially as shown in FIG. 22. As FIG. 20 shows, the diethanolamine salt of fospropofol produced endothermic peak at 57.2° C. when heated at a rate of 10° C./min. In some embodiments of the present disclosure, the diethanolamine salt of fospropofol is characterized by a DSC thermogram comprising an endothermic peak at about 57° C. when heated at a rate of 10° C./min.

Figure 23:
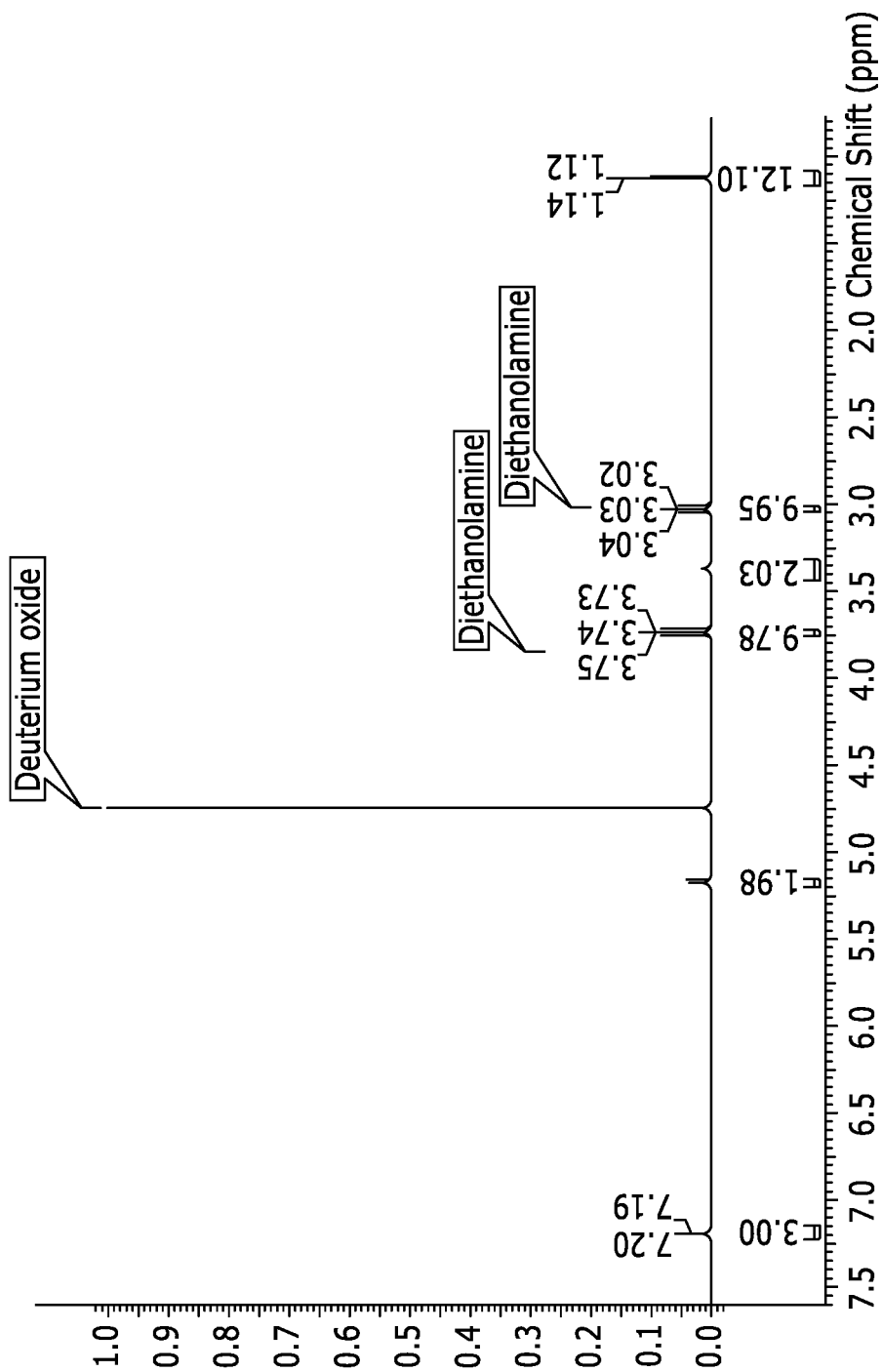
FIG. 23 shows a nuclear magnetic resonance (NMR) spectrum of a diethanolamine salt of fospropofol.

The diethanolamine salt of fospropofol can be characterized by an NMR spectrum substantially as shown in FIG. 23.

In some embodiments, the pharmaceutically acceptable salt of fospropofol is the ammonium salt.

Figure 24:
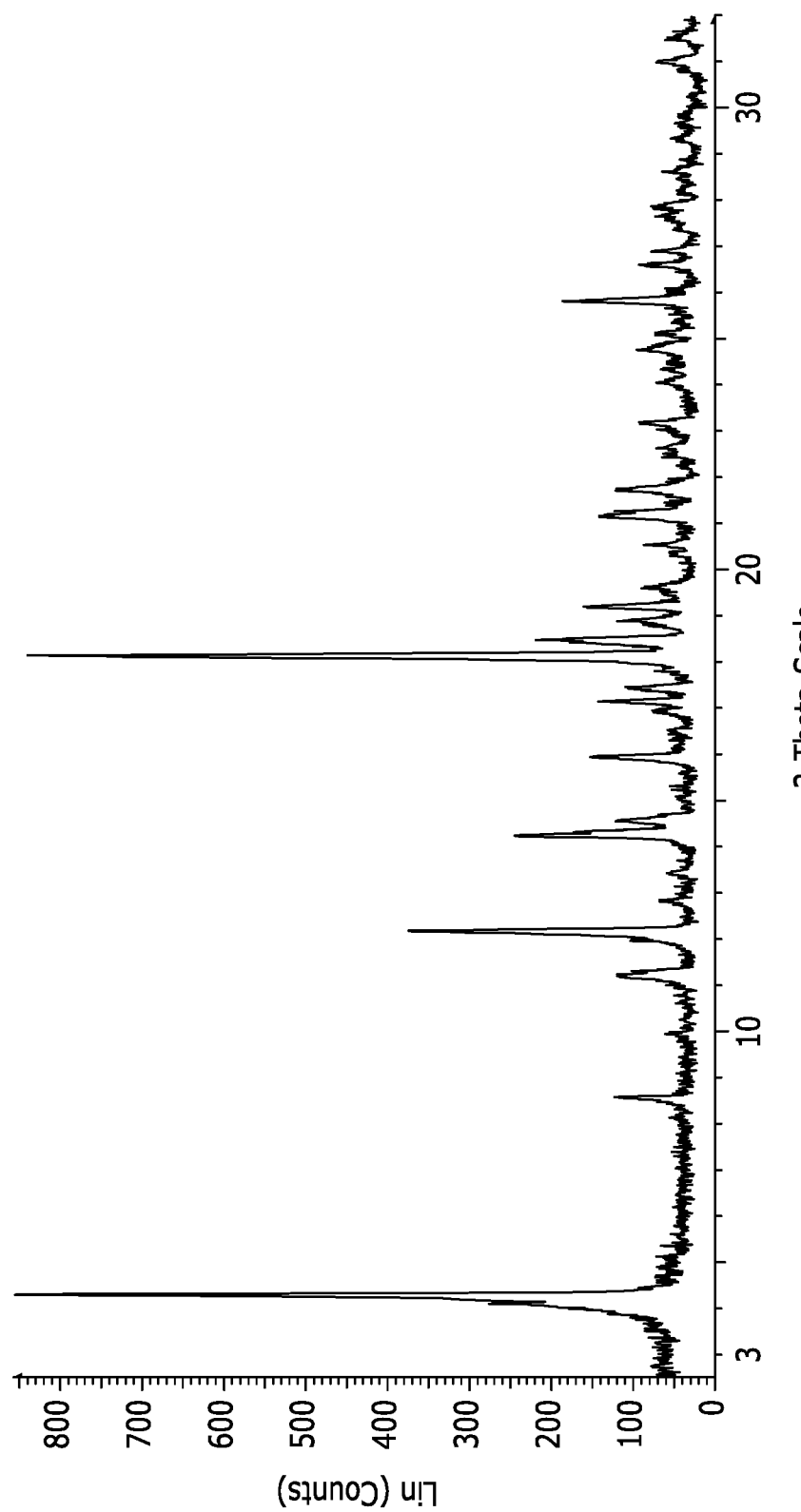
FIG. 24 shows an X-ray powder diffractogram (XRPD) of an ammonium salt of fospropofol.

In some embodiments, the ammonium salt of fospropofol has an XRPD substantially as shown in FIG. 24. The XRPD of the ammonium salt of fospropofol shown in FIG. 24 comprises reflection angles (degrees 2-theta±0.2 degrees 2-theta), and relative intensities as shown in Table 9:

TABLE 9

XRPD Data for ammonium salt of Fospropofol

| Angle (degrees 2-theta ± 0.2 degrees 2-theta) | Relative Intensity |
|---|---|
| 4.3 | 100.0 |
| 8.6 | 14.7 |
| 11.2 | 14.2 |
| 12.2 | 43.7 |
| 14.2 | 28.7 |
| 14.5 | 14.0 |
| 15.9 | 18.1 |
| 16.9 | 9.0 |
| 17.1 | 16.8 |
| 17.5 | 12.8 |
| 18.1 | 98.5 |
| 18.5 | 25.9 |
| 18.9 | 14.2 |
| 19.2 | 18.8 |
| 19.6 | 10.5 |
| 20.5 | 10.2 |
| 21.1 | 16.5 |
| 21.8 | 14.0 |
| 22.6 | 8.3 |
| 23.2 | 11.0 |
| 24.1 | 8.5 |
| 24.8 | 11.3 |
| 25.8 | 21.6 |
| 26.6 | 10.3 |
| 26.9 | 9.0 |

In some embodiments of the present disclosure, the ammonium salt of fospropofol is characterized by an XRPD pattern comprising a peak at one of the angles listed in Table 9. In other aspects, the ammonium salt of fospropofol is characterized by an XRPD pattern comprising more than one peak at one of the angles listed in Table 9 above. In other aspects, the ammonium salt of fospropofol is characterized by an XRPD pattern comprising two peaks selected from the angles listed in Table 9 above. In other aspects, the ammonium salt of fospropofol is characterized by an XRPD pattern comprising three peaks selected from the angles listed in Table 9 above. In other aspects, the ammonium salt of fospropofol is characterized by an XRPD pattern comprising four peaks selected from the angles listed in Table 9 above. In other aspects, the ammonium salt of fospropofol is characterized by an XRPD pattern comprising five peaks selected from the angles listed in Table 9 above. In other aspects, the ammonium salt of fospropofol is characterized by an XRPD pattern comprising six peaks selected from the angles listed in Table 9 above. In other aspects, the ammonium salt of fospropofol is characterized by an XRPD pattern comprising seven peaks selected from the angles listed in Table 9 above. In other aspects, the ammonium salt of fospropofol is characterized by an XRPD pattern comprising eight peaks selected from the angles listed in Table 9 above. In other aspects, the ammonium salt of fospropofol is characterized by an XRPD pattern comprising nine peaks selected from the angles listed in Table 9 above. In other aspects, the ammonium salt of fospropofol is characterized by an XRPD pattern comprising ten peaks selected from the angles listed in Table 9 above. In other aspects, the ammonium salt of fospropofol is characterized by an XRPD pattern comprising more than ten peaks selected from the angles listed in Table 9 above.

In some embodiments, the ammonium salt of fospropofol is characterized by an XRPD pattern comprising a peak at 18.1 degrees±0.2 degrees 2-theta. In other embodiments, the ammonium salt of fospropofol is characterized by an XRPD pattern comprising peaks at 18.1, 18.5, 19.2, 21.1, 21.8, and 25.8 degrees±0.2 degrees 2-theta. In other embodiments, the ammonium salt of fospropofol is characterized by an XRPD pattern comprising peaks at 12.2, 14.2, 15.9, 18.1, 18.5, and 19.2 degrees±0.2 degree 2-theta. In yet other embodiments, the ammonium salt of fospropofol is characterized by an XRPD pattern comprising peaks at 12.2, 14.2, 15.9, 18.1, 18.5, 19.2, 21.1, 21.8, and 25.8 degrees±0.2 degree 2-theta.

In some embodiments of the present disclosure, the ammonium salt of fospropofol is characterized by an XRPD pattern comprising peaks at three or more of 12.2, 14.2, 15.9, 18.1, 18.5, 19.2, 21.1, 21.8, and 25.8 degrees±0.2 degrees 2-theta. In some embodiments of the present disclosure, the ammonium salt of fospropofol is characterized by an XRPD pattern comprising peaks at four or more of 12.2, 14.2, 15.9, 18.1, 18.5, 19.2, 21.1, 21.8, and 25.8 degrees±0.2 degrees 2-theta. In some embodiments of the present disclosure, the ammonium salt of fospropofol is characterized by an XRPD pattern comprising peaks at five or more of 12.2, 14.2, 15.9, 18.1, 18.5, 19.2, 21.1, 21.8, and 25.8 degrees±0.2 degrees 2-theta. In some embodiments of the present disclosure, the ammonium salt of fospropofol is characterized by an XRPD pattern comprising peaks at six or more of 12.2, 14.2, 15.9, 18.1, 18.5, 19.2, 21.1, 21.8, and 25.8 degrees±0.2 degrees 2-theta. In some embodiments of the present disclosure, the ammonium salt of fospropofol is characterized by an XRPD pattern comprising peaks at seven or more of 12.2, 14.2, 15.9, 18.1, 18.5, 19.2, 21.1, 21.8, and 25.8 degrees±0.2 degrees 2-theta.

Figure 25:
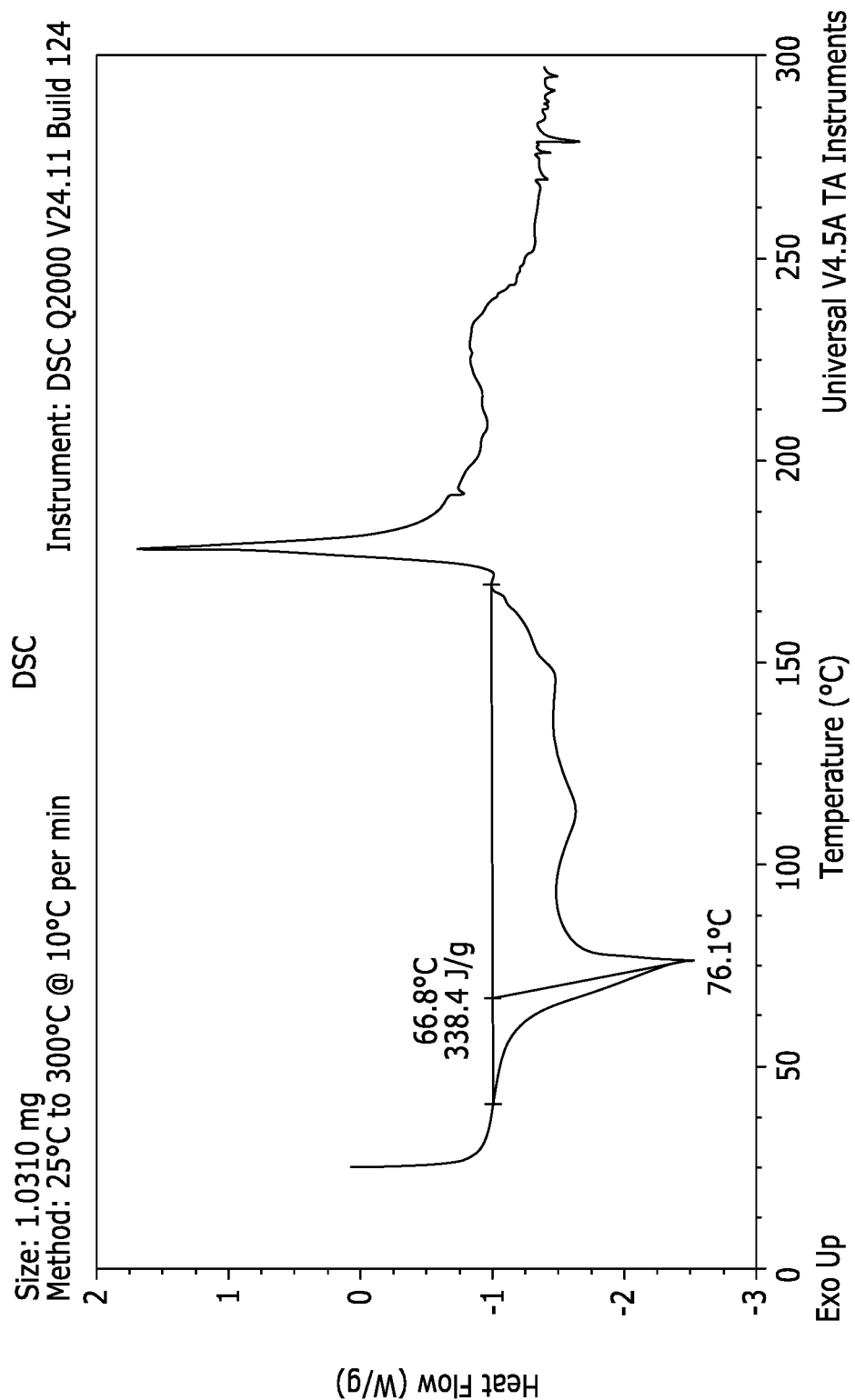
FIG. 25 shows a differential scanning calorimetry (DSC) profile of the ammonium salt of fospropofol.

The ammonium salt of fospropofol can be characterized by a DSC thermogram substantially as shown in FIG. 25. As FIG. 25 shows, the ammonium salt of fospropofol produced endothermic peak at 76.1° C. when heated at a rate of 10° C./min. In some embodiments of the present disclosure, the ammonium salt of fospropofol is characterized by a DSC thermogram comprising an endothermic peak at about 76° C. when heated at a rate of 10° C./min.

In some embodiments of the present disclosure, the ammonium salt of fospropofol is characterized by an XRPD pattern comprising peaks at 12.2, 14.2, 15.9, 18.1, 18.5, 19.2, 21.1, 21.8, and 25.8 degrees±0.2 degrees 2-theta, and a DSC thermogram comprising an endothermic peak at about 76° C. when heated at a rate of 10° C./min.

In some embodiments, the pharmaceutically acceptable salt of fospropofol is the tromethamine (i.e., 2-amino-2-(hydroxymethyl)propane-1,3-diol) salt.

Figure 26:
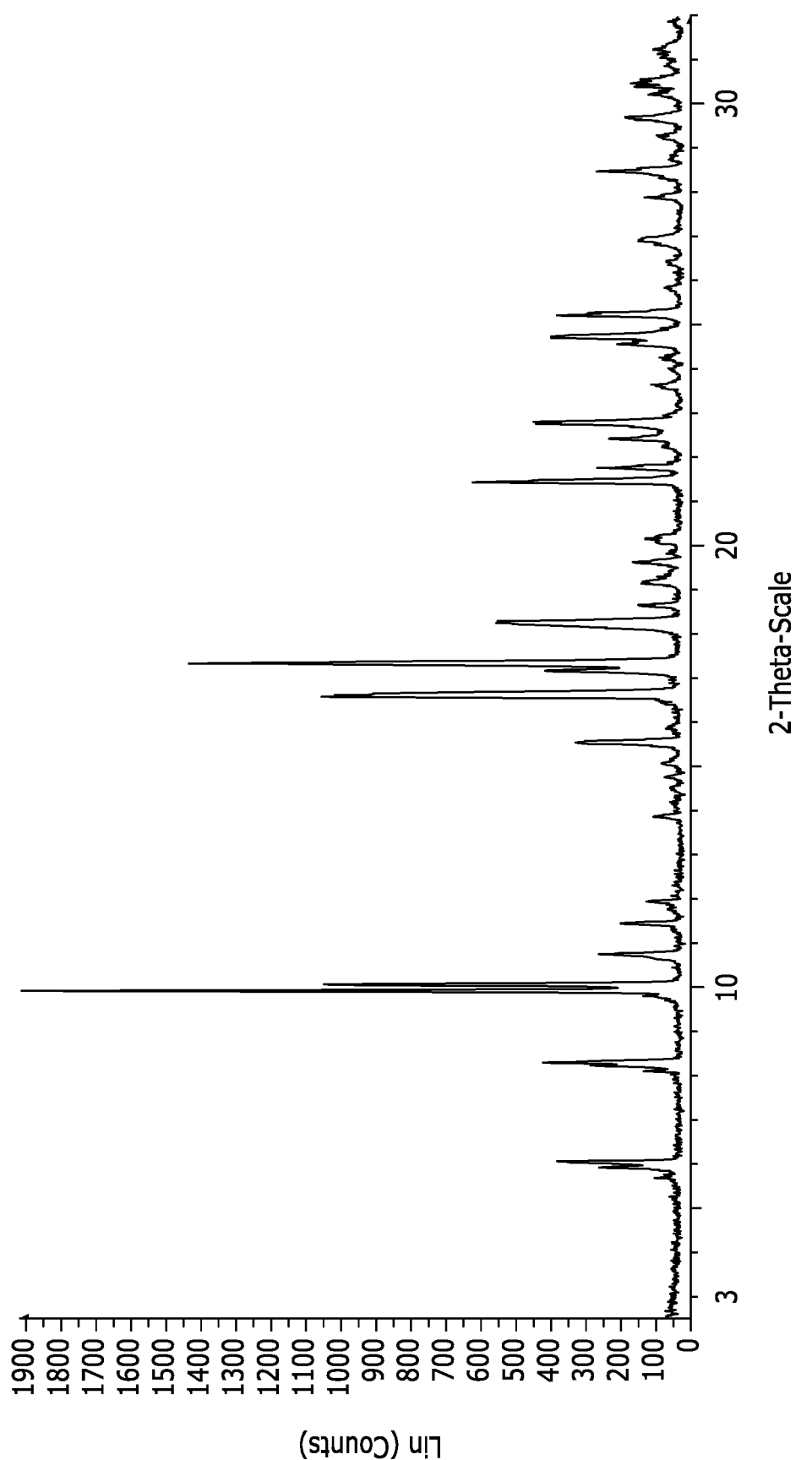
FIG. 26 shows an X-ray powder diffractogram (XRPD) of a tromethamine salt of fospropofol.

In some embodiments, the tromethamine salt of fospropofol has an XRPD substantially as shown in FIG. 26. The XRPD of the tromethamine salt of fospropofol shown in FIG. 26 comprises reflection angles (degrees 2-theta±0.2 degrees 2-theta), and relative intensities as shown in Table 10:

TABLE 10

| XRPD Data for tromethamine salt of Fospropofol | |
|---|---|
| Angle (degrees 2-theta ± 0.2 degrees 2-theta) | Relative Intensity |
| 5.9 | 13.4 |
| 6.0 | 19.9 |
| 8.3 | 22.3 |
| 9.9 | 100.0 |
| 10.0 | 55.0 |
| 10.7 | 13.9 |

TABLE 10-continued

| XRPD Data for tromethamine salt of Fospropofol | |
|---|---|
| Angle (degrees 2-theta ± 0.2 degrees 2-theta) | Relative Intensity |
| 11.4 | 10.5 |
| 11.9 | 6.3 |
| 13.8 | 5.7 |
| 15.5 | 17.0 |
| 16.6 | 55.5 |
| 17.2 | 21.6 |
| 17.3 | 75.0 |
| 18.3 | 28.7 |
| 18.6 | 7.9 |
| 19.2 | 7.1 |
| 19.6 | 9.0 |
| 20.1 | 7.0 |
| 21.4 | 32.9 |
| 21.8 | 14.2 |
| 22.4 | 12.2 |
| 22.7 | 23.0 |
| 23.7 | 6.2 |
| 24.6 | 10.8 |
| 24.7 | 20.9 |
| 25.2 | 19.9 |
| 26.9 | 7.4 |
| 27.9 | 6.5 |
| 28.5 | 14.2 |
| 29.3 | 5.1 |
| 29.7 | 10.2 |

In some embodiments of the present disclosure, the tromethamine salt of fospropofol is characterized by an XRPD pattern comprising a peak at one of the angles listed in Table 10. In other aspects, the tromethamine salt of fospropofol is characterized by an XRPD pattern comprising more than one peak at one of the angles listed in Table 10 above. In other aspects, the tromethamine salt of fospropofol is characterized by an XRPD pattern comprising two peaks selected from the angles listed in Table 10 above. In other aspects, the tromethamine salt of fospropofol is characterized by an XRPD pattern comprising three peaks selected from the angles listed in Table 10 above. In other aspects, the tromethamine salt of fospropofol is characterized by an XRPD pattern comprising four peaks selected from the angles listed in Table 10 above. In other aspects, the tromethamine salt of fospropofol is characterized by an XRPD pattern comprising five peaks selected from the angles listed in Table 10 above. In other aspects, the tromethamine salt of fospropofol is characterized by an XRPD pattern comprising six peaks selected from the angles listed in Table 10 above. In other aspects, the tromethamine salt of fospropofol is characterized by an XRPD pattern comprising seven peaks selected from the angles listed in Table 10 above. In other aspects, the tromethamine salt of fospropofol is characterized by an XRPD pattern comprising eight peaks selected from the angles listed in Table 10 above. In other aspects, the tromethamine salt of fospropofol is characterized by an XRPD pattern comprising nine peaks selected from the angles listed in Table 10 above. In other aspects, the tromethamine salt of fospropofol is characterized by an XRPD pattern comprising ten peaks selected from the angles listed in Table 10 above. In other aspects, the tromethamine salt of fospropofol is characterized by an XRPD pattern comprising more than ten peaks selected from the angles listed in Table 10 above.

In some embodiments, the tromethamine salt of fospropofol is characterized by an XRPD pattern comprising a peak at 10.0, 16.6, and 17.3 degrees±0.2 degrees 2-theta. In other embodiments, the tromethamine salt of fospropofol is characterized by an XRPD pattern comprising peaks at 10.0, 10.7, 16.6, 17.3, and 18.3 degrees±0.2 degrees 2-theta. In other embodiments, the tromethamine salt of fospropofol is characterized by an XRPD pattern comprising peaks at 10.0, 16.6, 17.3, 18.3, 24.7, and 25.2 degrees±0.2 degree 2-theta. In yet other embodiments, the tromethamine salt of fospropofol is characterized by an XRPD pattern comprising peaks at 6.0, 10.0, 10.7, 16.6, 17.3, 18.3, 24.7, and 25.2 degrees±0.2 degree 2-theta.

In some embodiments of the present disclosure, the tromethamine salt of fospropofol is characterized by an XRPD pattern comprising peaks at three or more of 6.0, 10.0, 10.7, 16.6, 17.3, 18.3, 24.7, and 25.2 degrees±0.2 degrees 2-theta. In some embodiments of the present disclosure, the tromethamine salt of fospropofol is characterized by an XRPD pattern comprising peaks at four or more of 6.0, 10.0, 10.7, 16.6, 17.3, 18.3, 24.7, and 25.2 degrees±0.2 degrees 2-theta. In some embodiments of the present disclosure, the tromethamine salt of fospropofol is characterized by an XRPD pattern comprising peaks at five or more of 6.0, 10.0, 10.7, 16.6, 17.3, 18.3, 24.7, and 25.2 degrees±0.2 degrees 2-theta. In some embodiments of the present disclosure, the tromethamine salt of fospropofol is characterized by an XRPD pattern comprising peaks at six or more of 6.0, 10.0, 10.7, 16.6, 17.3, 18.3, 24.7, and 25.2 degrees±0.2 degrees 2-theta. In some embodiments of the present disclosure, the tromethamine salt of fospropofol is characterized by an XRPD pattern comprising peaks at seven or more of 6.0, 10.0, 10.7, 16.6, 17.3, 18.3, 24.7, and 25.2 degrees±0.2 degrees 2-theta.

Figure 27:
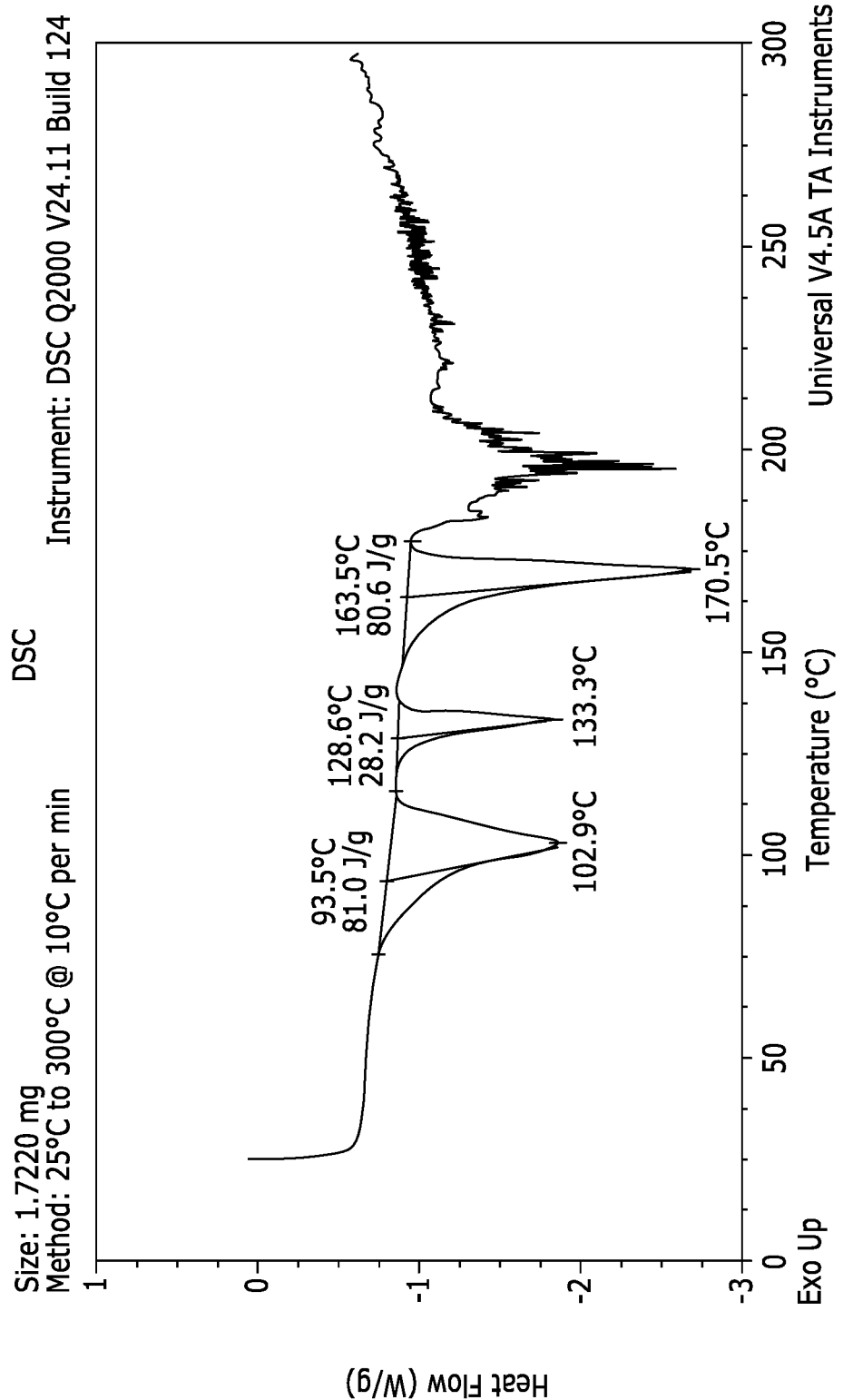
FIG. 27 shows a differential scanning calorimetry (DSC) profile of a tromethamine salt of fospropofol.
Figure 28:
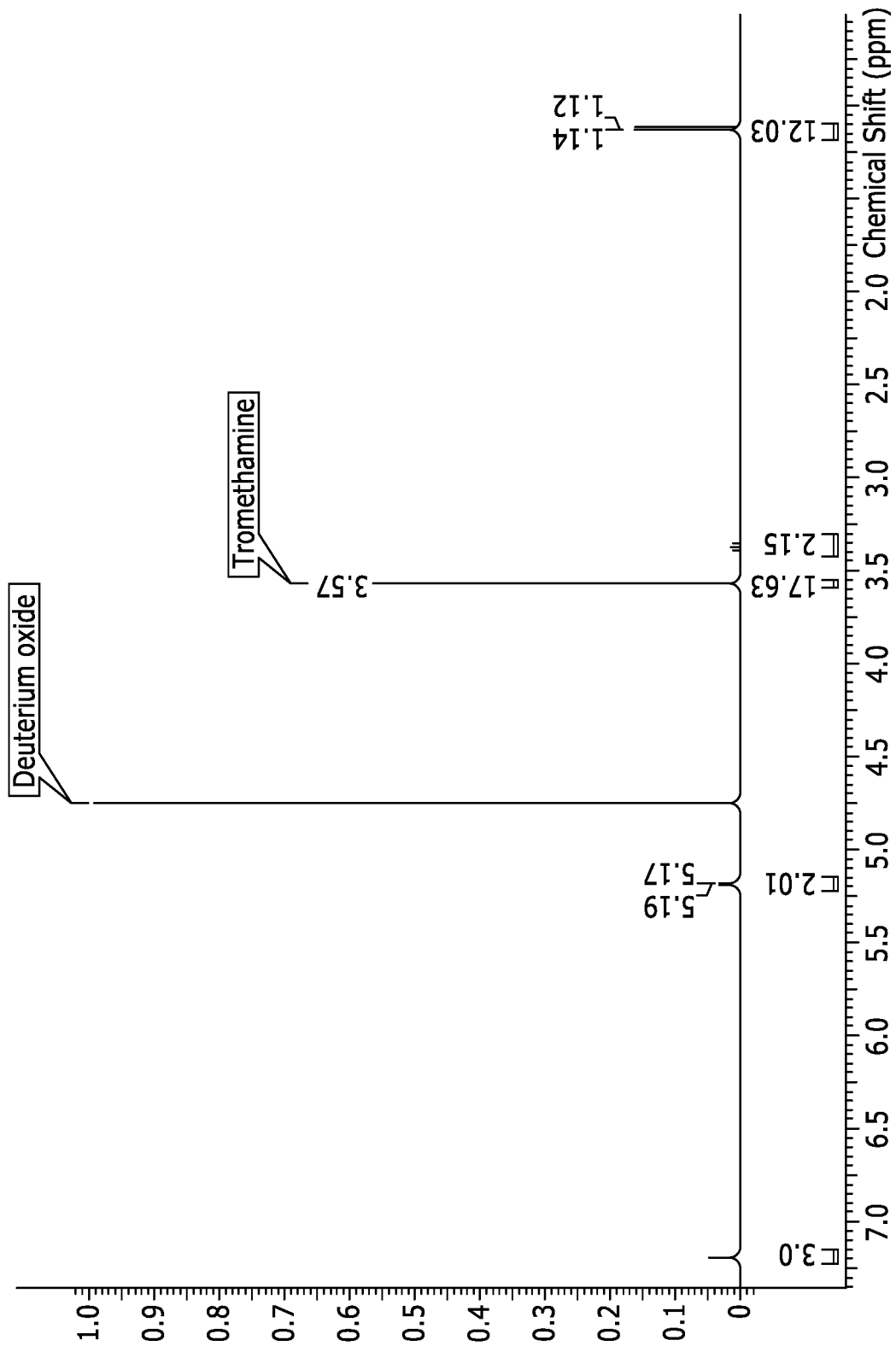
FIG. 28 shows a nuclear magnetic resonance (NMR) spectrum of a tromethamine salt of fospropofol.

The tromethamine salt of fospropofol can be characterized by a DSC thermogram substantially as shown in FIG. 27. As FIG. 27 shows, the tromethamine salt of fospropofol produced endothermic peaks at 102.9° C., 133.3° C., and 170.5° C. when heated at a rate of 10° C./min. In some embodiments of the present disclosure, the tromethamine salt of fospropofol is characterized by a DSC thermogram comprising an endothermic peaks at about 103° C., about 133° C., or about 171° C. when heated at a rate of 10° C./min.

In some embodiments of the present disclosure, the tromethamine salt of fospropofol is characterized by an XRPD pattern comprising peaks at one or more of 6.0, 10.0, 10.7, 16.6, 17.3, 18.3, 24.7, and 25.2 degrees±0.2 degrees 2-theta, and a DSC thermogram comprising an endothermic peak at about 103° C., about 133° C., or about 171° C. when heated at a rate of 10° C./min.

In some embodiments, the tromethamine salt of fospropofol can be characterized by an NMR spectrum substantially as shown in FIG. 26.

In some embodiments, the pharmaceutically acceptable salt of fospropofol is the benethamine (i.e., N-benzyl-2-phenylethanamine) salt.

Figure 29:
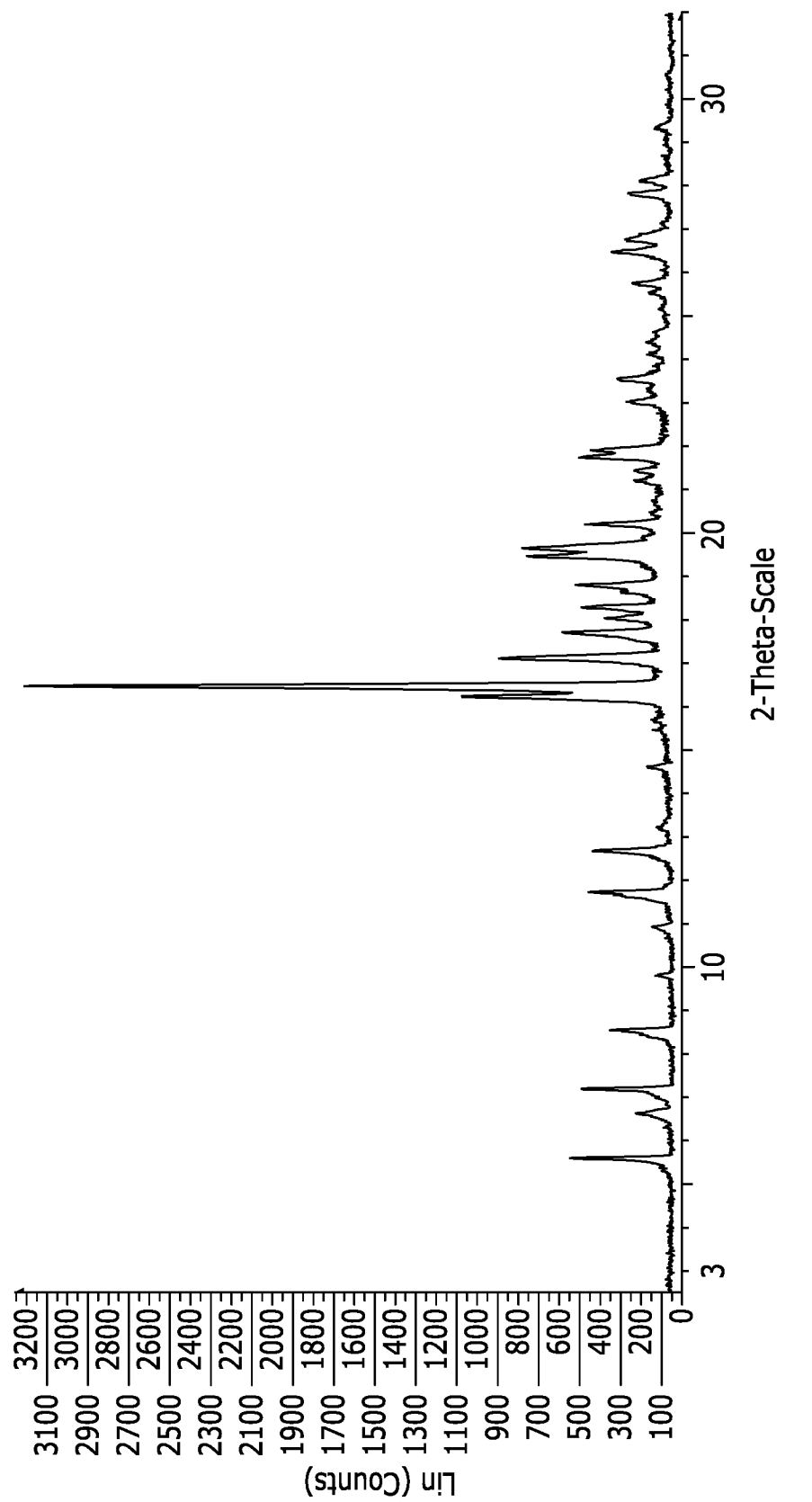
FIG. 29 shows an X-ray powder diffractogram (XRPD) of a benethamine salt of fospropofol.

In some embodiments, the benethamine salt of fospropofol has an XRPD substantially as shown in FIG. 29. The XRPD of the benethamine salt of fospropofol shown in FIG. 29 comprises reflection angles (degrees 2-theta±0.2 degrees 2-theta), and relative intensities as shown in Table 11:

TABLE 11

XRPD Data for benethamine salt of Fospropofol

| Angle (degrees 2-theta ± 0.2 degrees 2-theta) | Relative Intensity |
|---|---|
| 5.5 | 17.0 |
| 6.6 | 6.9 |
| 7.2 | 15.3 |

TABLE 11-continued

XRPD Data for benethamine salt of Fospropofol

| Angle (degrees 2-theta ± 0.2 degrees 2-theta) | Relative Intensity |
|---|---|
| 8.5 | 10.9 |
| 9.8 | 4.1 |
| 10.9 | 4.8 |
| 11.7 | 14.5 |
| 12.6 | 13.6 |
| 14.6 | 5.3 |
| 16.2 | 33.5 |
| 16.4 | 100.0 |
| 17.1 | 28.1 |
| 17.7 | 18.4 |
| 18.0 | 12.0 |
| 18.3 | 15.4 |
| 18.8 | 16.2 |
| 19.5 | 23.5 |
| 19.6 | 24.4 |
| 20.2 | 14.8 |
| 21.2 | 7.4 |
| 21.4 | 7.3 |
| 21.7 | 15.7 |
| 21.9 | 14.0 |
| 23.0 | 8.5 |
| 23.5 | 9.9 |
| 25.5 | 4.8 |
| 25.8 | 7.4 |
| 26.5 | 11.0 |
| 26.7 | 8.5 |
| 27.8 | 8.3 |
| 28.1 | 6.5 |

In some embodiments of the present disclosure, the benethamine salt of fospropofol is characterized by an XRPD pattern comprising a peak at one of the angles listed in Table 11. In other aspects, the benethamine salt of fospropofol is characterized by an XRPD pattern comprising more than one peak at one of the angles listed in Table 11 above. In other aspects, the benethamine salt of fospropofol is characterized by an XRPD pattern comprising two peaks selected from the angles listed in Table 11 above. In other aspects, the benethamine salt of fospropofol is characterized by an XRPD pattern comprising three peaks selected from the angles listed in Table 11 above. In other aspects, the benethamine salt of fospropofol is characterized by an XRPD pattern comprising four peaks selected from the angles listed in Table 11 above. In other aspects, the benethamine salt of fospropofol is characterized by an XRPD pattern comprising five peaks selected from the angles listed in Table 11 above. In other aspects, the benethamine salt of fospropofol is characterized by an XRPD pattern comprising six peaks selected from the angles listed in Table 11 above. In other aspects, the benethamine salt of fospropofol is characterized by an XRPD pattern comprising seven peaks selected from the angles listed in Table 11 above. In other aspects, the benethamine salt of fospropofol is characterized by an XRPD pattern comprising eight peaks selected from the angles listed in Table 11 above. In other aspects, the benethamine salt of fospropofol is characterized by an XRPD pattern comprising nine peaks selected from the angles listed in Table 11 above. In other aspects, the benethamine salt of fospropofol is characterized by an XRPD pattern comprising ten peaks selected from the angles listed in Table 11 above. In other aspects, the benethamine salt of fospropofol is characterized by an XRPD pattern comprising more than ten peaks selected from the angles listed in Table 11 above.

In some embodiments, the benethamine salt of fospropofol is characterized by an XRPD pattern comprising a peak at 16.4 degrees±0.2 degrees 2-theta. In other embodiments, the benethamine salt of fospropofol is characterized by an XRPD pattern comprising peaks at 8.5, 11.7, 12.6, and 16.4 degrees±0.2 degrees 2-theta. In other embodiments, the benethamine salt of fospropofol is characterized by an XRPD pattern comprising peaks at 5.5, 7.2, 8.5, 11.7, 12.6, and 16.4 degrees±0.2 degree 2-theta. In yet other embodiments, the benethamine salt of fospropofol is characterized by an XRPD pattern comprising peaks at 5.5, 7.2, 8.5, 11.7, 12.6, 16.4, 17.7, and 19.6 degrees±0.2 degree 2-theta.

In some embodiments of the present disclosure, the benethamine salt of fospropofol is characterized by an XRPD pattern comprising peaks at three or more of 5.5, 7.2, 8.5, 11.7, 12.6, 16.4, 17.7, and 19.6 degrees±0.2 degrees 2-theta. In some embodiments of the present disclosure, the benethamine salt of fospropofol is characterized by an XRPD pattern comprising peaks at four or more of 5.5, 7.2, 8.5, 11.7, 12.6, 16.4, 17.7, and 19.6 degrees±0.2 degrees 2-theta. In some embodiments of the present disclosure, the benethamine salt of fospropofol is characterized by an XRPD pattern comprising peaks at five or more of 5.5, 7.2, 8.5, 11.7, 12.6, 16.4, 17.7, and 19.6 degrees±0.2 degrees 2-theta. In some embodiments of the present disclosure, the benethamine salt of fospropofol is characterized by an XRPD pattern comprising peaks at six or more of 5.5, 7.2, 8.5, 11.7, 12.6, 16.4, 17.7, and 19.6 degrees±0.2 degrees 2-theta.

Figure 30:
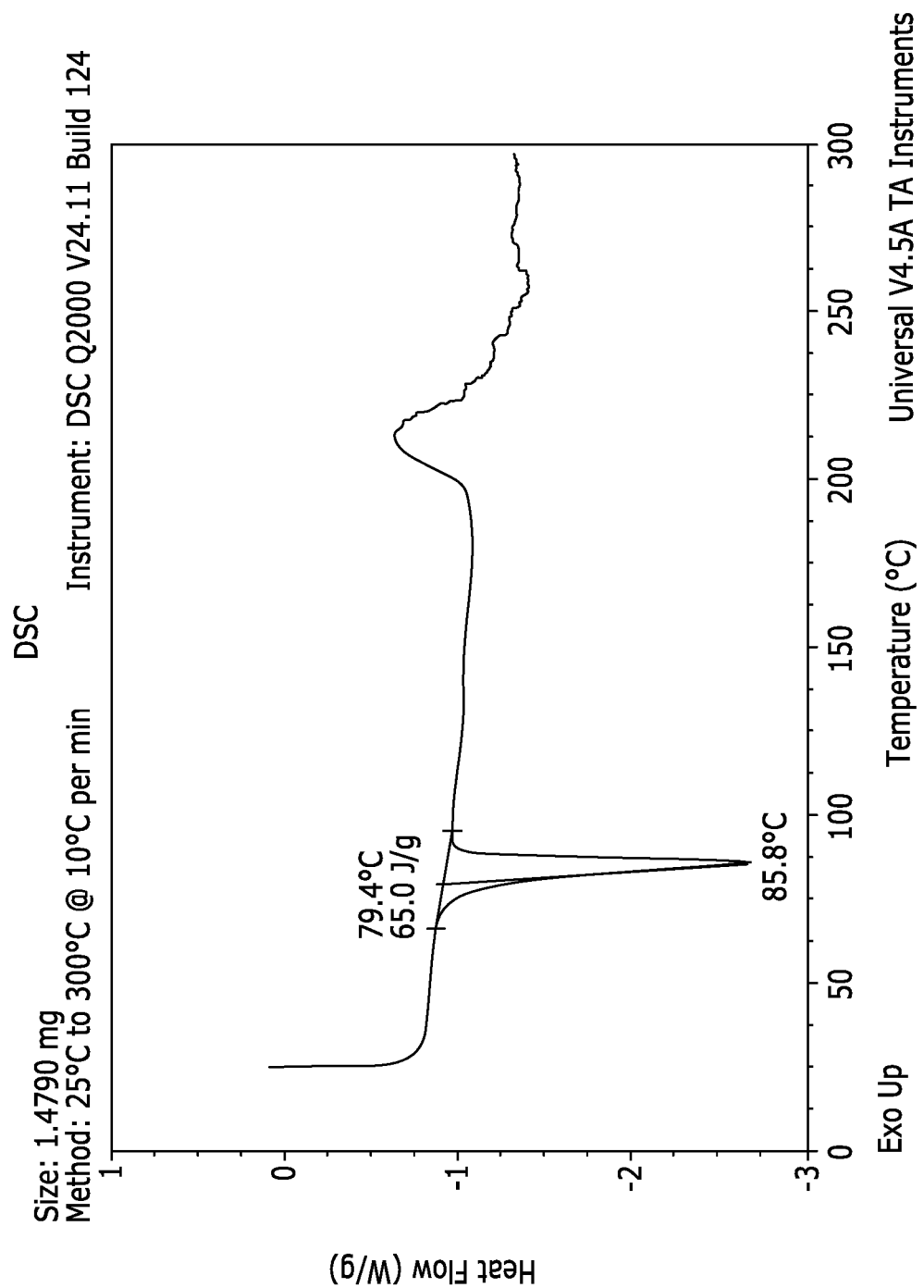
FIG. 30 shows a differential scanning calorimetry (DSC) profile of a benethamine salt of fospropofol.

The benethamine salt of fospropofol can be characterized by a DSC thermogram substantially as shown in FIG. 30. As FIG. 30 shows, the benethamine salt of fospropofol produced endothermic peaks at 85.8° C. when heated at a rate of 10° C./min. In some embodiments of the present disclosure, the benethamine salt of fospropofol is characterized by a DSC thermogram comprising an endothermic peaks at about 86° C. when heated at a rate of 10° C./min.

In some embodiments of the present disclosure, the benethamine salt of fospropofol is characterized by an XRPD pattern comprising peaks at one or more of 5.5, 7.2, 8.5, 11.7, 12.6, 16.4, 17.7, and 19.6 degrees±0.2 degrees 2-theta, and a DSC thermogram comprising an endothermic peak at about 86° C. when heated at a rate of 10° C./min.

Figure 31:
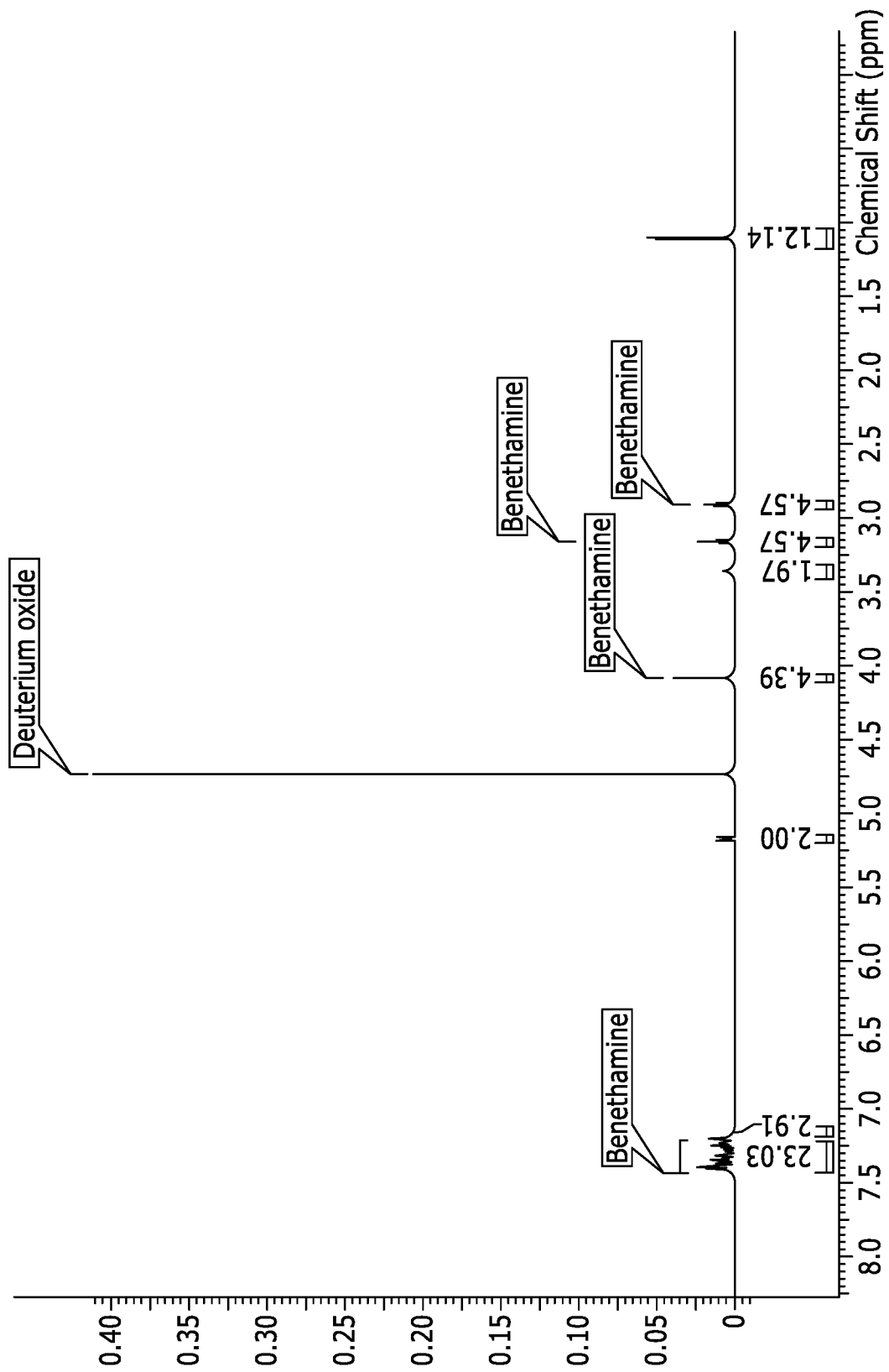
FIG. 31 shows a nuclear magnetic resonance (NMR) spectrum of a benethamine salt of fospropofol.

In some embodiments, the benethamine salt of fospropofol can be characterized by an NMR spectrum substantially as shown in FIG. 31.

In some embodiments, the pharmaceutically acceptable salt of fospropofol is the histidine salt.

Figure 32:
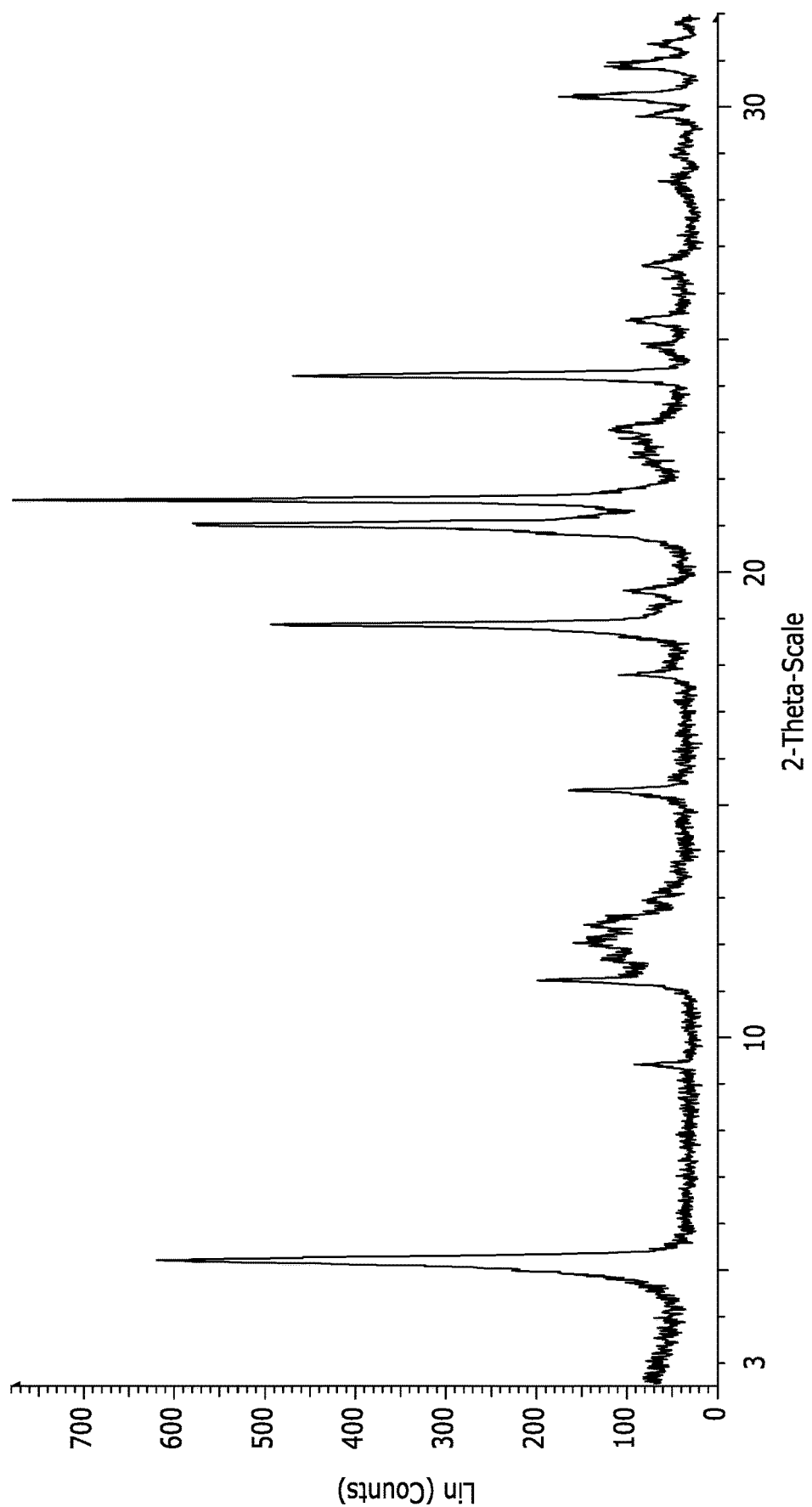
FIG. 32 shows an X-ray powder diffractogram (XRPD) of a histidine salt of fospropofol.

In some embodiments, the histidine salt of fospropofol has an XRPD substantially as shown in FIG. 32. The XRPD of the histidine salt of fospropofol shown in FIG. 32 comprises reflection angles (degrees 2-theta±0.2 degrees 2-theta), and relative intensities as shown in Table 12:

TABLE 12

| XRPD Data for histidine salt of Fospropofol | |
|---|---|
| Angle (degrees 2-theta ± 0.2 degrees 2-theta) | Relative Intensity |
| 5.2 | 79.7 |
| 9.4 | 11.6 |
| 11.2 | 25.7 |
| 11.7 | 16.3 |
| 12.0 | 20.3 |
| 12.4 | 19.0 |
| 15.3 | 20.8 |

TABLE 12-continued

| XRPD Data for histidine salt of Fospropofol | |
|---|---|
| Angle (degrees 2-theta ± 0.2 degrees 2-theta) | Relative Intensity |
| 17.8 | 14.3 |
| 18.9 | 63.5 |
| 19.6 | 13.1 |
| 21.1 | 74.3 |
| 21.5 | 100.0 |
| 23.1 | 15.3 |
| 24.2 | 60.4 |
| 25.4 | 12.9 |
| 26.6 | 10.3 |
| 29.8 | 11.7 |
| 30.2 | 22.3 |
| 30.9 | 15.9 |
| 31.4 | 10.0 |

In some embodiments of the present disclosure, the histidine salt of fospropofol is characterized by an XRPD pattern comprising a peak at one of the angles listed in Table 12. In other aspects, the histidine salt of fospropofol is characterized by an XRPD pattern comprising more than one peak at one of the angles listed in Table 12 above. In other aspects, the histidine salt of fospropofol is characterized by an XRPD pattern comprising two peaks selected from the angles listed in Table 12 above. In other aspects, the histidine salt of fospropofol is characterized by an XRPD pattern comprising three peaks selected from the angles listed in Table 12 above. In other aspects, the histidine salt of fospropofol is characterized by an XRPD pattern comprising four peaks selected from the angles listed in Table 12 above. In other aspects, the histidine salt of fospropofol is characterized by an XRPD pattern comprising five peaks selected from the angles listed in Table 12 above. In other aspects, the histidine salt of fospropofol is characterized by an XRPD pattern comprising six peaks selected from the angles listed in Table 12 above. In other aspects, the histidine salt of fospropofol is characterized by an XRPD pattern comprising seven peaks selected from the angles listed in Table 12 above. In other aspects, the histidine salt of fospropofol is characterized by an XRPD pattern comprising eight peaks selected from the angles listed in Table 12 above. In other aspects, the histidine salt of fospropofol is characterized by an XRPD pattern comprising nine peaks selected from the angles listed in Table 12 above. In other aspects, the histidine salt of fospropofol is characterized by an XRPD pattern comprising ten peaks selected from the angles listed in Table 12 above. In other aspects, the histidine salt of fospropofol is characterized by an XRPD pattern comprising more than ten peaks selected from the angles listed in Table 12 above.

In some embodiments, the histidine salt of fospropofol is characterized by an XRPD pattern comprising a peak at 11.2, 15.3, and 18.9 degrees±0.2 degrees 2-theta. In other embodiments, the histidine salt of fospropofol is characterized by an XRPD pattern comprising peaks at 18.9, 21.1, 21.5, and 24.2 degrees±0.2 degrees 2-theta. In other embodiments, the histidine salt of fospropofol is characterized by an XRPD pattern comprising peaks at 18.9, 21.1, 21.5, 24.2, and 30.2 degrees±0.2 degree 2-theta. In yet other embodiments, the histidine salt of fospropofol is characterized by an XRPD pattern comprising peaks at 11.2, 15.3, 18.9, 21.1, 21.5, 24.2, and 30.2 degrees±0.2 degree 2-theta.

In some embodiments of the present disclosure, the histidine salt of fospropofol is characterized by an XRPD pattern comprising peaks at three or more of 11.2, 15.3, 18.9, 21.1, 21.5, 24.2, and 30.2 degrees±0.2 degrees 2-theta. In some embodiments of the present disclosure, the histidine salt of fospropofol is characterized by an XRPD pattern comprising peaks at four or more of 11.2, 15.3, 18.9, 21.1, 21.5, 24.2, and 30.2 degrees±0.2 degrees 2-theta. In some embodiments of the present disclosure, the histidine salt of fospropofol is characterized by an XRPD pattern comprising peaks at five or more of 11.2, 15.3, 18.9, 21.1, 21.5, 24.2, and 30.2 degrees±0.2 degrees 2-theta. In some embodiments of the present disclosure, the histidine salt of fospropofol is characterized by an XRPD pattern comprising peaks at six or more of 11.2, 15.3, 18.9, 21.1, 21.5, 24.2, and 30.2 degrees±0.2 degrees 2-theta.

Figure 33:
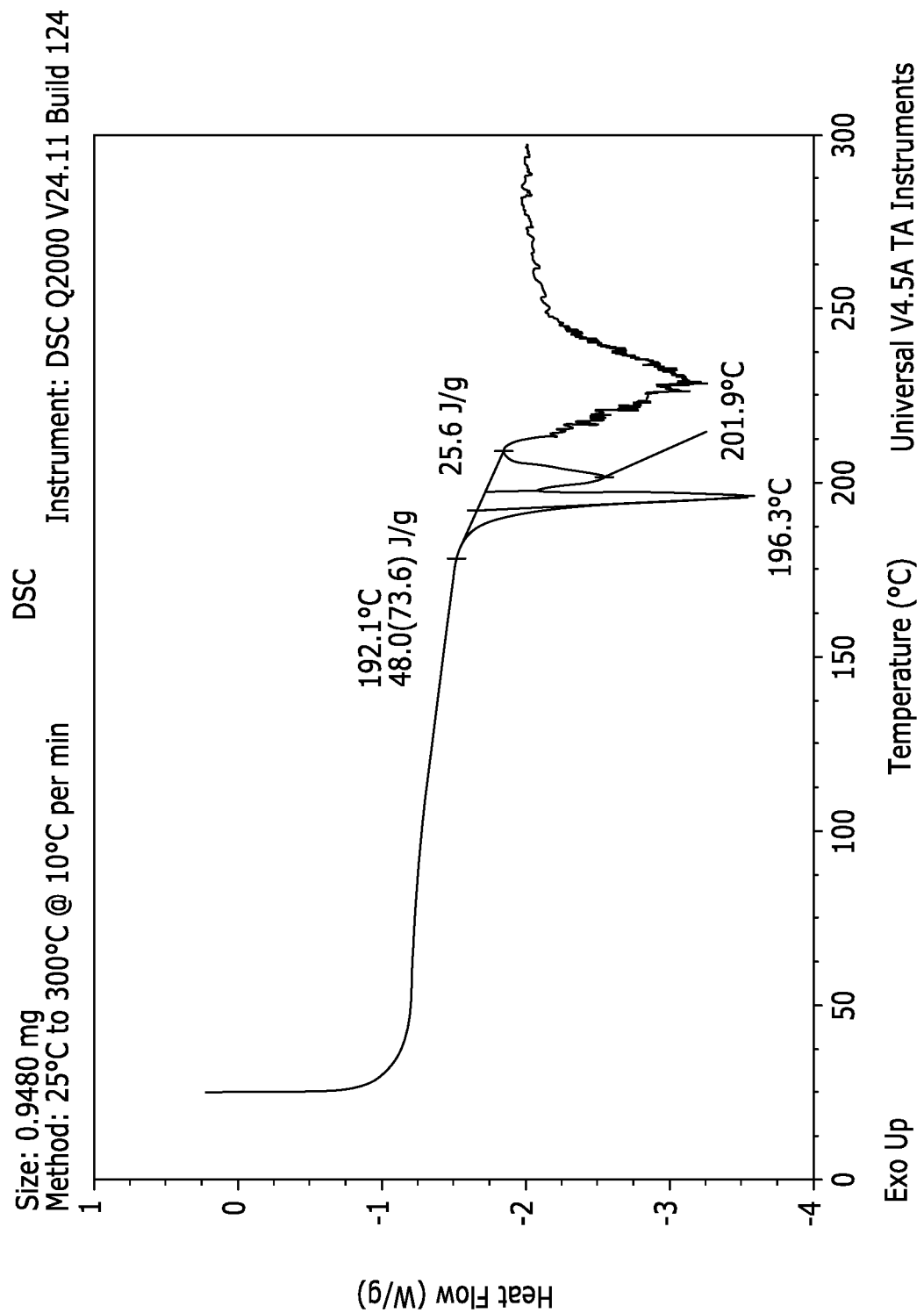
FIG. 33 shows a differential scanning calorimetry (DSC) profile of a histidine salt of fospropofol.

The histidine salt of fospropofol can be characterized by a DSC thermogram substantially as shown in FIG. 33. As FIG. 33 shows, the histidine salt of fospropofol produced endothermic peaks at 196.3° C. and 201.9° C. when heated at a rate of 10° C./min. In some embodiments of the present disclosure, the histidine salt of fospropofol is characterized by a DSC thermogram comprising an endothermic peaks at about 196° C. or 202° C. when heated at a rate of 10° C./min.

In some embodiments of the present disclosure, the histidine salt of fospropofol is characterized by an XRPD pattern comprising peaks at one or more of 11.2, 15.3, 18.9, 21.1, 21.5, 24.2, and 30.2 degrees±0.2 degrees 2-theta, and a DSC thermogram comprising an endothermic peak at about 196° C. or 202° C. when heated at a rate of 10° C./min.

Figure 34:
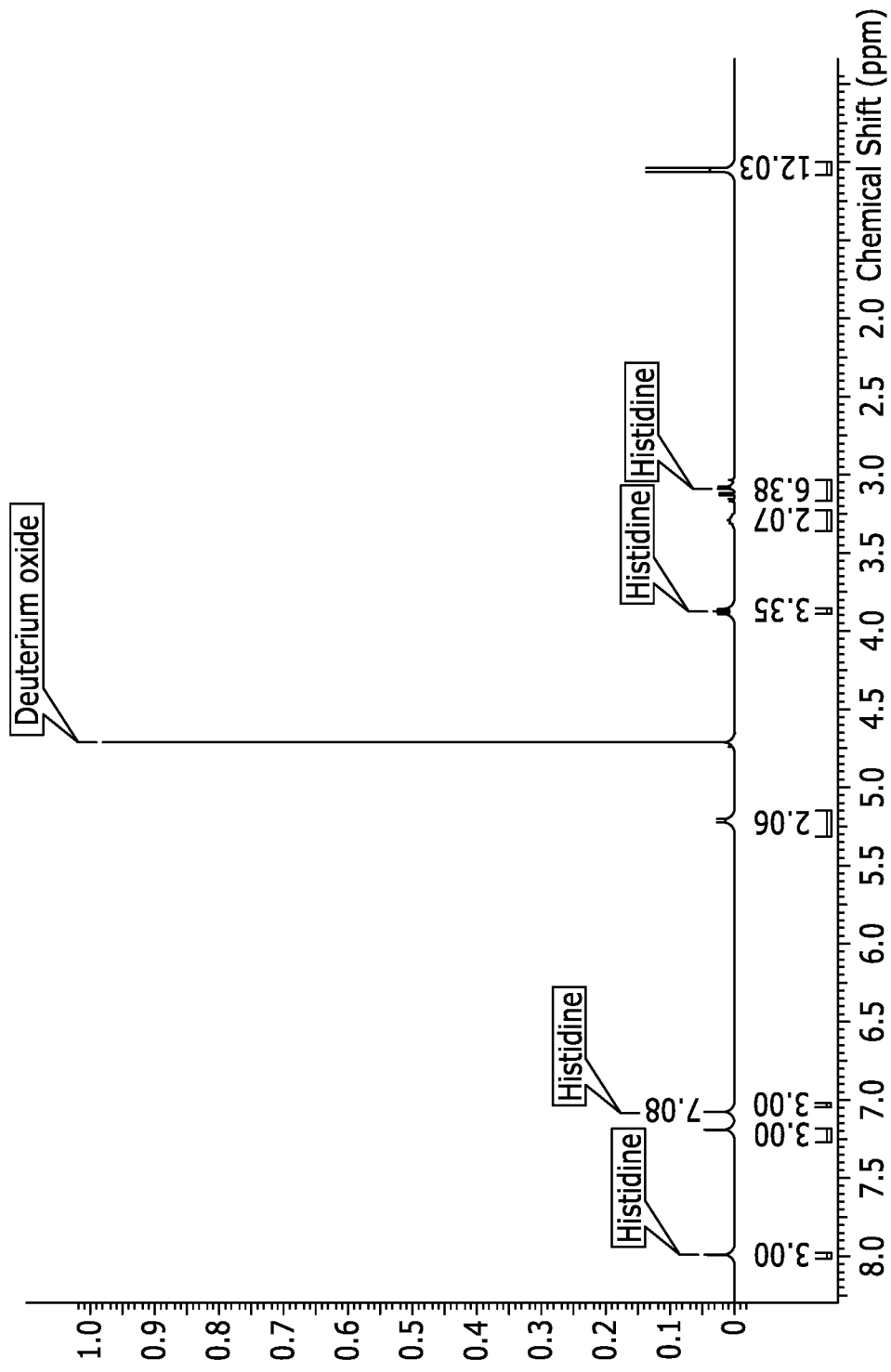
FIG. 34 shows a nuclear magnetic resonance (NMR) spectrum of a histidine salt of fospropofol.

In some embodiments, the histidine salt of fospropofol can be characterized by an NMR spectrum substantially as shown in FIG. 34.

In some embodiments, the pharmaceutically acceptable salt of fospropofol is the calcium salt.

Figure 35:
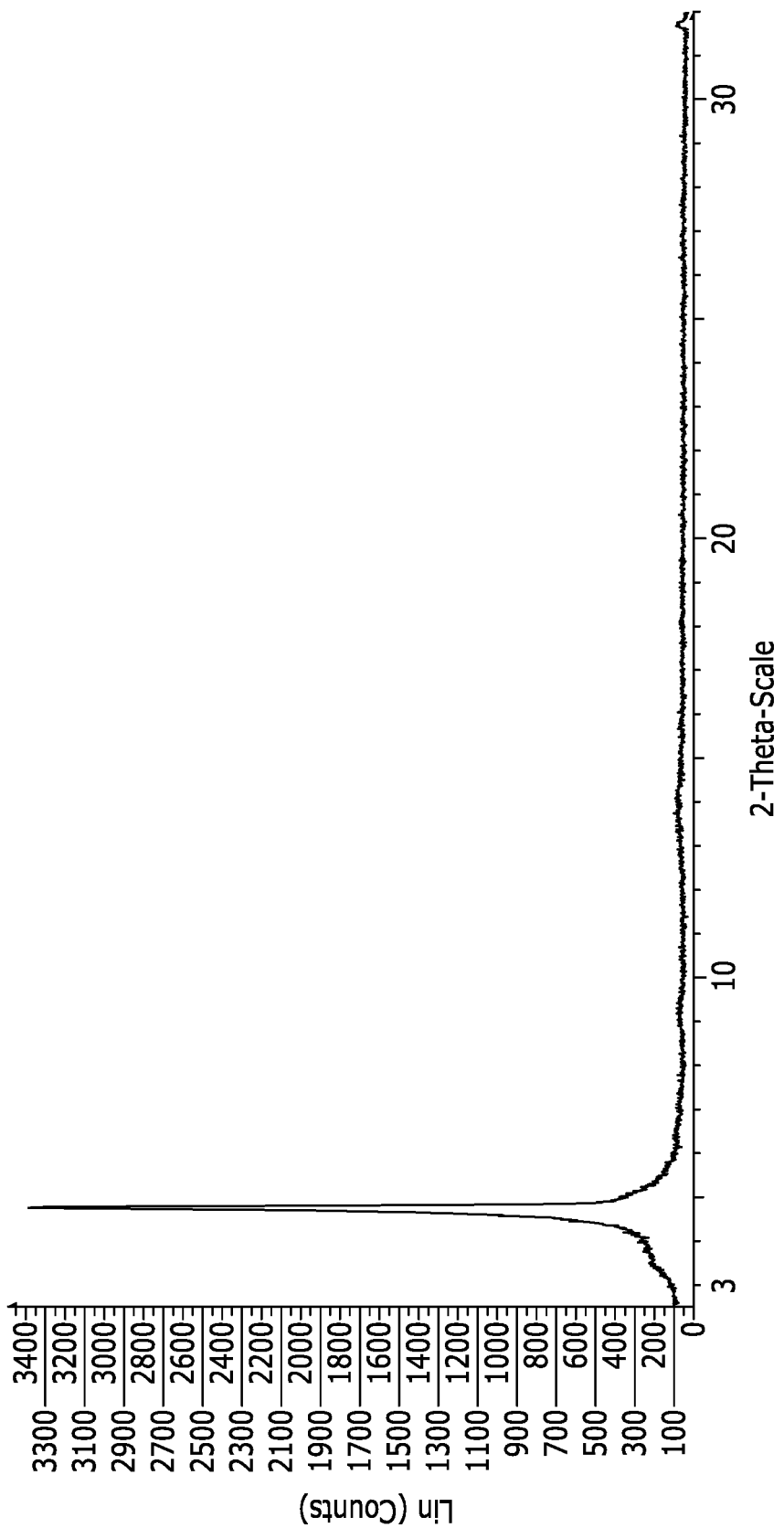
FIG. 35 shows an X-ray powder diffractogram (XRPD) of a calcium salt of fospropofol (Form I).

In some embodiments, the calcium salt of fospropofol (Form I) has an XRPD substantially as shown in FIG. 35. The Form I calcium salt of fospropofol has a single peak at 4.7 degrees 2-theta±0.2 degrees 2-theta.

Figure 36:
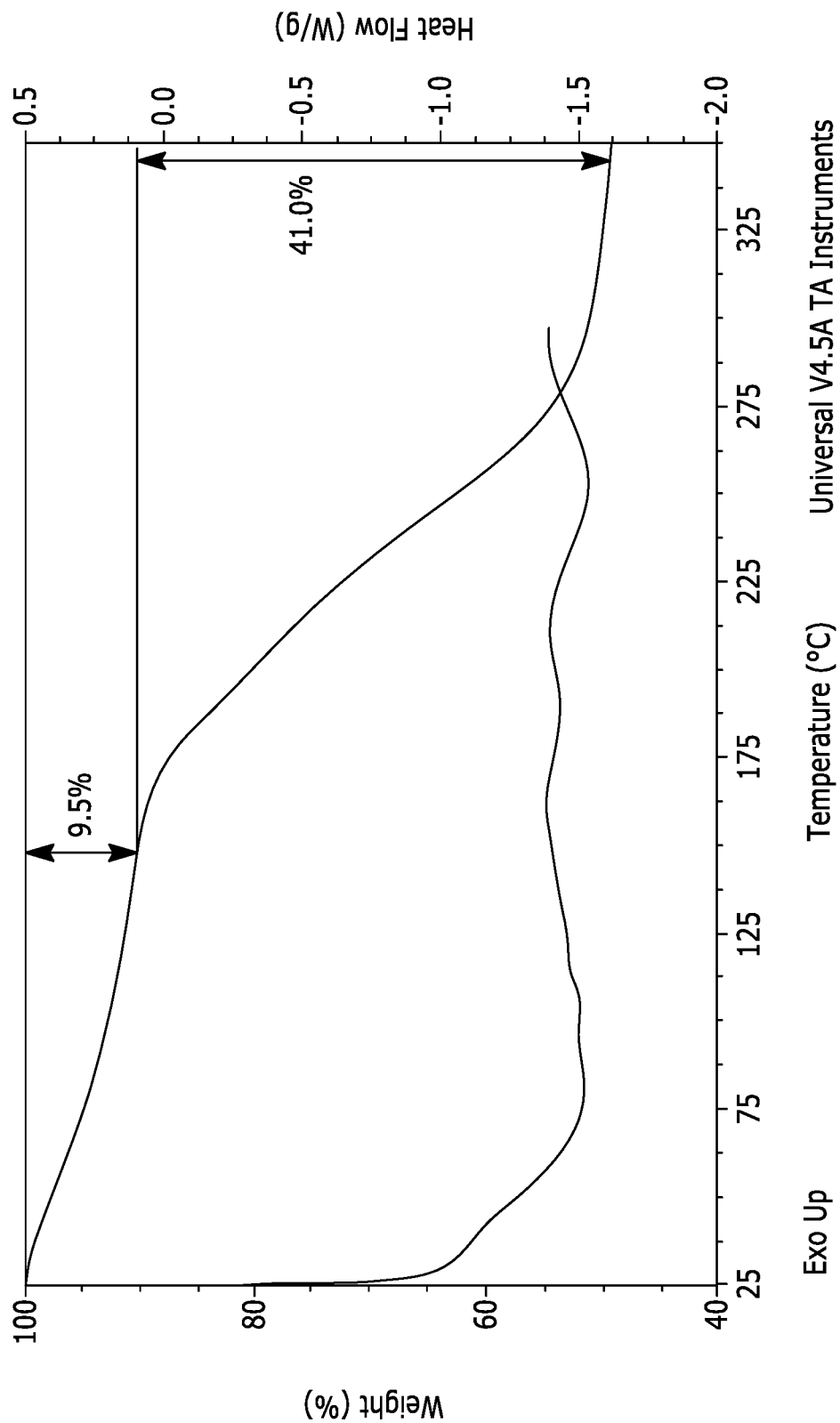
FIG. 36 shows a thermogravimetric analysis (TGA) profile of a calcium salt of fospropofol (Form I).

In some embodiments, the Form I calcium salt of fospropofol can be characterized by a DSC thermogram substantially as shown in FIG. 36.

In other embodiments, the Form I calcium salt of fospropofol can be characterized by a TGA profile substantially as shown in FIG. 36. As FIG. 36 shows, the Form I calcium salt of fospropofol lost about 9.5% of its weight upon heating to 125° C., and about 41% of its weight upon heating to 325° C. a rate of 10° C./min.

Figure 37:
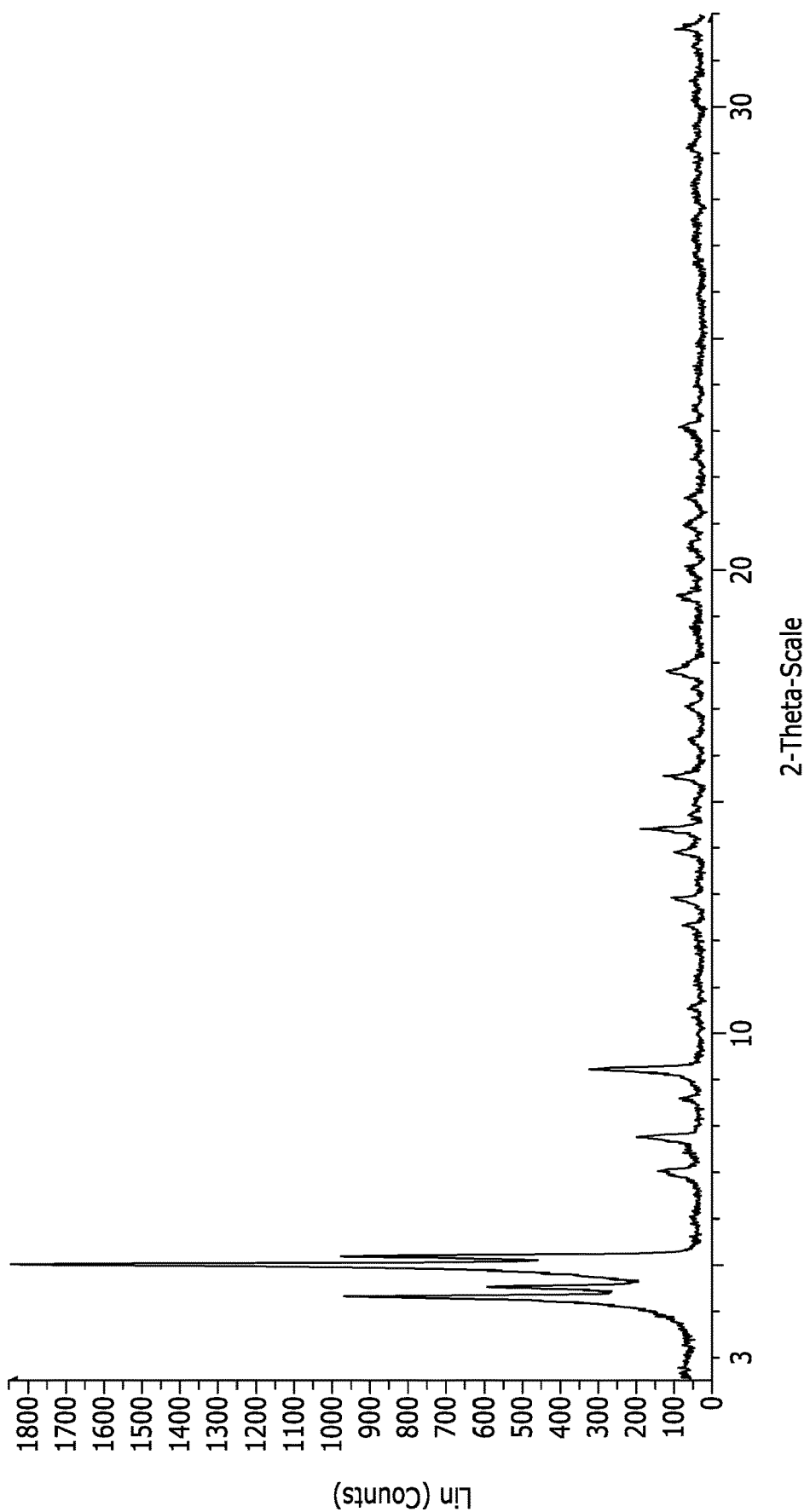
FIG. 37 shows an X-ray powder diffractogram (XRPD) of a calcium salt of fospropofol (Form II).

In other embodiments, the calcium salt of fospropofol (Form II) has an XRPD substantially as shown in FIG. 37. The XRPD of the Form II calcium salt of fospropofol shown in FIG. 37 comprises reflection angles (degrees 2-theta±0.2 degrees 2-theta), and relative intensities as shown in Table 13 Å:

TABLE 13A

| XRPD Data for Form II calcium salt of Fospropofol | |
|---|---|
| Angle (degrees 2-theta ± 0.2 degrees 2-theta) | Relative Intensity |
| 4.3 | 52.7 |
| 4.5 | 32.0 |
| 5.0 | 100.0 |
| 5.1 | 52.9 |
| 7.0 | 7.7 |
| 7.7 | 11.1 |
| 8.6 | 4.8 |
| 9.2 | 17.6 |
| 12.3 | 4.3 |
| 12.9 | 5.9 |
| 13.9 | 5.3 |
| 14.4 | 10.5 |
| 15.6 | 7.1 |
| 16.3 | 3.4 |
| 17.1 | 3.9 |
| 17.8 | 6.5 |
| 19.4 | 4.6 |
| 20.0 | 3.9 |
| 20.5 | 3.2 |
| 21.0 | 4.2 |
| 21.5 | 4.0 |

In some embodiments of the present disclosure, the calcium salt of fospropofol is characterized by an XRPD pattern comprising a peak at one of the angles listed in Table 13A. In other aspects, the calcium salt of fospropofol is characterized by an XRPD pattern comprising more than one peak at one of the angles listed in Table 13A above. In other aspects, the calcium salt of fospropofol is characterized by an XRPD pattern comprising two peaks selected from the angles listed in Table 13A above. In other aspects, the calcium salt of fospropofol is characterized by an XRPD pattern comprising three peaks selected from the angles listed in Table 13A above. In other aspects, the calcium salt of fospropofol is characterized by an XRPD pattern comprising four peaks selected from the angles listed in Table 13A above. In other aspects, the calcium salt of fospropofol is characterized by an XRPD pattern comprising five peaks selected from the angles listed in Table 13A above. In other aspects, the calcium salt of fospropofol is characterized by an XRPD pattern comprising six peaks selected from the angles listed in Table 13A above. In other aspects, the calcium salt of fospropofol is characterized by an XRPD pattern comprising seven peaks selected from the angles listed in Table 13A above. In other aspects, the calcium salt of fospropofol is characterized by an XRPD pattern comprising eight peaks selected from the angles listed in Table 13A above. In other aspects, the calcium salt of fospropofol is characterized by an XRPD pattern comprising nine peaks selected from the angles listed in Table 13A above. In other aspects, the calcium salt of fospropofol is characterized by an XRPD pattern comprising ten peaks selected from the angles listed in Table 13A above. In other aspects, the calcium salt of fospropofol is characterized by an XRPD pattern comprising more than ten peaks selected from the angles listed in Table 13A above.

In some embodiments, the calcium salt of fospropofol is characterized by an XRPD pattern comprising a peak at 5.1, 7.0, 7.7, 8.6, 9.2, and 14.4 degrees±0.2 degrees 2-theta. In other embodiments, the calcium salt of fospropofol is characterized by an XRPD pattern comprising peaks at 5.0, 5.1, 7.0, 7.7, 8.6, and 9.2 degrees±0.2 degrees 2-theta. In other embodiments, the calcium salt of fospropofol is characterized by an XRPD pattern comprising peaks at 5.0, 5.1, 7.0, 7.7, 8.6, 9.2, and 14.4 degrees±0.2 degree 2-theta. In yet other embodiments, the calcium salt of fospropofol is characterized by an XRPD pattern comprising peaks at 4.3, 4.5, 5.0, 5.1, 7.0, 7.7, 8.6, 9.2, and 14.4 degrees±0.2 degree 2-theta.

In some embodiments of the present disclosure, the calcium salt of fospropofol is characterized by an XRPD pattern comprising peaks at three or more of 4.3, 4.5, 5.0, 5.1, 7.0, 7.7, 8.6, 9.2, and 14.4 degrees±0.2 degrees 2-theta. In some embodiments of the present disclosure, the calcium salt of fospropofol is characterized by an XRPD pattern comprising peaks at four or more of 4.3, 4.5, 5.0, 5.1, 7.0, 7.7, 8.6, 9.2, and 14.4 degrees±0.2 degrees 2-theta. In some embodiments of the present disclosure, the calcium salt of fospropofol is characterized by an XRPD pattern comprising peaks at five or more of 4.3, 4.5, 5.0, 5.1, 7.0, 7.7, 8.6, 9.2, and 14.4 degrees±0.2 degrees 2-theta. In some embodiments of the present disclosure, the calcium salt of fospropofol is characterized by an XRPD pattern comprising peaks at six or more of 4.3, 4.5, 5.0, 5.1, 7.0, 7.7, 8.6, 9.2, and 14.4 degrees±0.2 degrees 2-theta.

Figure 38:
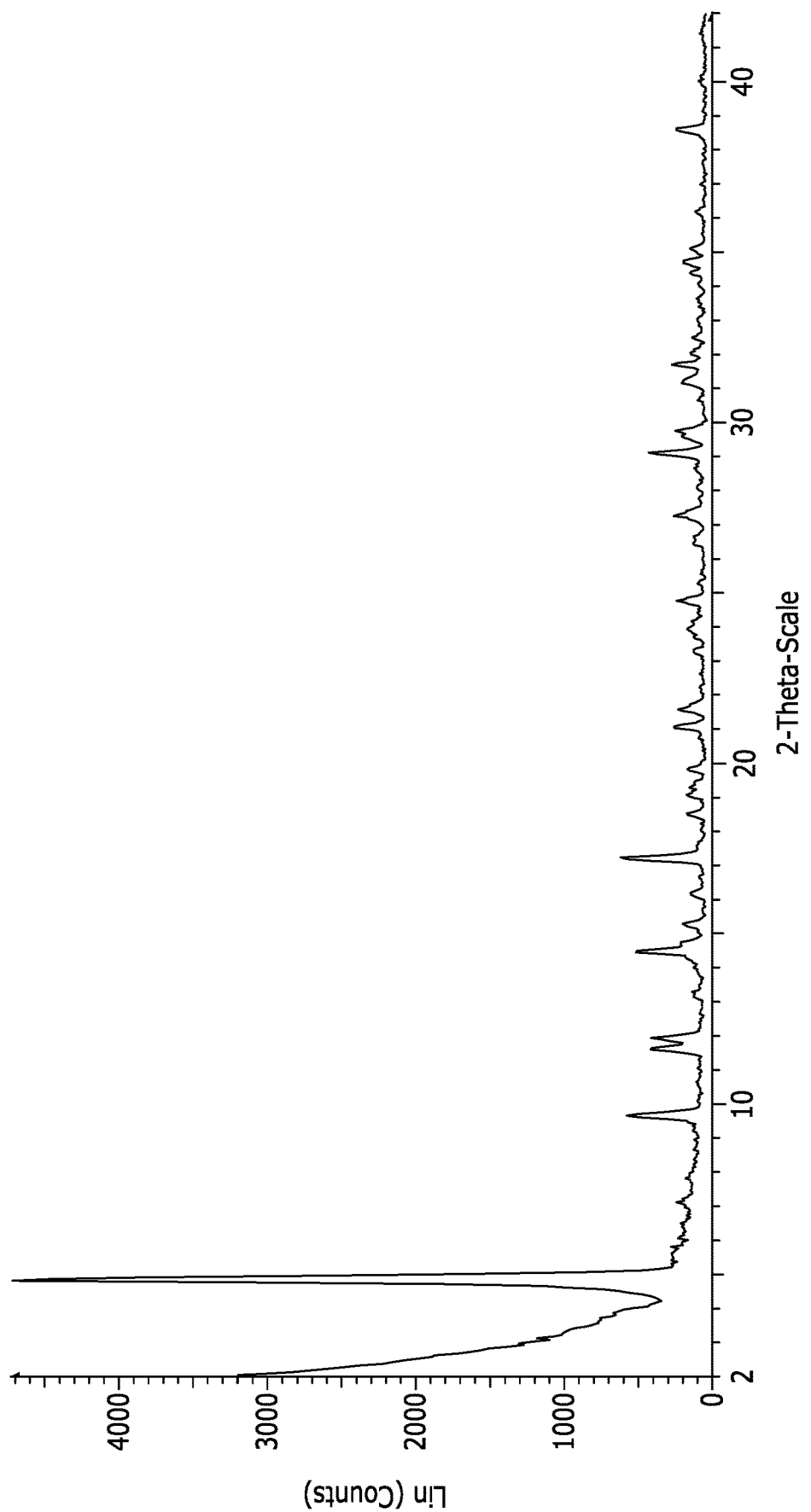
FIG. 38 shows an X-ray powder diffractogram (XRPD) of a calcium salt of fospropofol (Form III).

In yet other embodiments, the calcium salt of fospropofol (Form III) has an XRPD substantially as shown in FIG. 38. The XRPD of the Form III calcium salt of fospropofol shown in FIG. 38 comprises reflection angles (degrees 2-theta±0.2 degrees 2-theta), and relative intensities as shown in Table 13:

TABLE 13

XRPD Data for Form III calcium salt of Fospropofol

| Angle (degrees 2-theta ± 0.2 degrees 2-theta) | Relative Intensity |
| --- | --- |
| 4.8 | 100.0 |
| 9.7 | 12.0 |
| 11.6 | 9.3 |
| 11.9 | 8.8 |
| 13.2 | 2.9 |
| 14.5 | 11.3 |
| 15.3 | 4.0 |
| 16.1 | 3.2 |
| 17.2 | 13.0 |
| 18.3 | 3.7 |
| 19.1 | 3.2 |
| 19.3 | 3.4 |
| 19.8 | 3.9 |
| 21.1 | 5.4 |
| 21.6 | 4.8 |
| 23.3 | 2.6 |
| 24.0 | 3.5 |
| 24.8 | 4.9 |
| 26.5 | 2.6 |
| 27.3 | 5.2 |
| 29.1 | 9.3 |
| 29.6 | 4.6 |
| 29.8 | 5.7 |
| 31.2 | 4.2 |
| 31.7 | 5.9 |
| 34.5 | 3.1 |
| 34.8 | 4.3 |
| 35.1 | 3.2 |
| 38.6 | 5.1 |

In some embodiments of the present disclosure, the calcium salt of fospropofol is characterized by an XRPD pattern comprising a peak at one of the angles listed in Table 13. In other aspects, the calcium salt of fospropofol is characterized by an XRPD pattern comprising more than one peak at one of the angles listed in Table 13 above. In other aspects, the calcium salt of fospropofol is characterized by an XRPD pattern comprising two peaks selected from the angles listed in Table 13 above. In other aspects, the calcium salt of fospropofol is characterized by an XRPD pattern comprising three peaks selected from the angles listed in Table 13 above. In other aspects, the calcium salt of fospropofol is characterized by an XRPD pattern comprising four peaks selected from the angles listed in Table 13 above. In other aspects, the calcium salt of fospropofol is characterized by an XRPD pattern comprising five peaks selected from the angles listed in Table 13 above. In other aspects, the calcium salt of fospropofol is characterized by an XRPD pattern comprising six peaks selected from the angles listed in Table 13 above. In other aspects, the calcium salt of fospropofol is characterized by an XRPD pattern comprising seven peaks selected from the angles listed in Table 13 above. In other aspects, the calcium salt of fospropofol is characterized by an XRPD pattern comprising eight peaks selected from the angles listed in Table 13 above. In other aspects, the calcium salt of fospropofol is characterized by an XRPD pattern comprising nine peaks selected from the angles listed in Table 13 above. In other aspects, the calcium salt of fospropofol is characterized by an XRPD pattern comprising ten peaks selected from the angles listed in Table 13 above. In other aspects, the calcium salt of fospropofol is characterized by an XRPD pattern comprising more than ten peaks selected from the angles listed in Table 13 above.

In some embodiments, the calcium salt of fospropofol is characterized by an XRPD pattern comprising a peak at 4.8, and 9.7 degrees±0.2 degrees 2-theta. In other embodiments, the calcium salt of fospropofol is characterized by an XRPD pattern comprising peaks at 9.7, 11.6, 11.9, 14.5, and 17.2 degrees±0.2 degrees 2-theta. In other embodiments, the calcium salt of fospropofol is characterized by an XRPD pattern comprising peaks at 11.6, 11.9, 14.5, and 17.2 degrees±0.2 degree 2-theta. In yet other embodiments, the calcium salt of fospropofol is characterized by an XRPD pattern comprising peaks at 4.8, 9.7, 11.6, 11.9, 14.5, 17.2, and 29.1 degrees±0.2 degree 2-theta.

In some embodiments of the present disclosure, the calcium salt of fospropofol is characterized by an XRPD pattern comprising peaks at three or more of 4.8, 9.7, 11.6, 11.9, 14.5, 17.2, and 29.1 degrees±0.2 degrees 2-theta. In some embodiments of the present disclosure, the calcium salt of fospropofol is characterized by an XRPD pattern comprising peaks at four or more of 4.8, 9.7, 11.6, 11.9, 14.5, 17.2, and 29.1 degrees±0.2 degrees 2-theta. In some embodiments of the present disclosure, the calcium salt of fospropofol is characterized by an XRPD pattern comprising peaks at five or more of 4.8, 9.7, 11.6, 11.9, 14.5, 17.2, and 29.1 degrees±0.2 degrees 2-theta. In some embodiments of the present disclosure, the calcium salt of fospropofol is characterized by an XRPD pattern comprising peaks at six or more of 4.8, 9.7, 11.6, 11.9, 14.5, 17.2, and 29.1 degrees±0.2 degrees 2-theta.

In some embodiments, the pharmaceutically acceptable salt of fospropofol is the magnesium salt.

Figure 39:
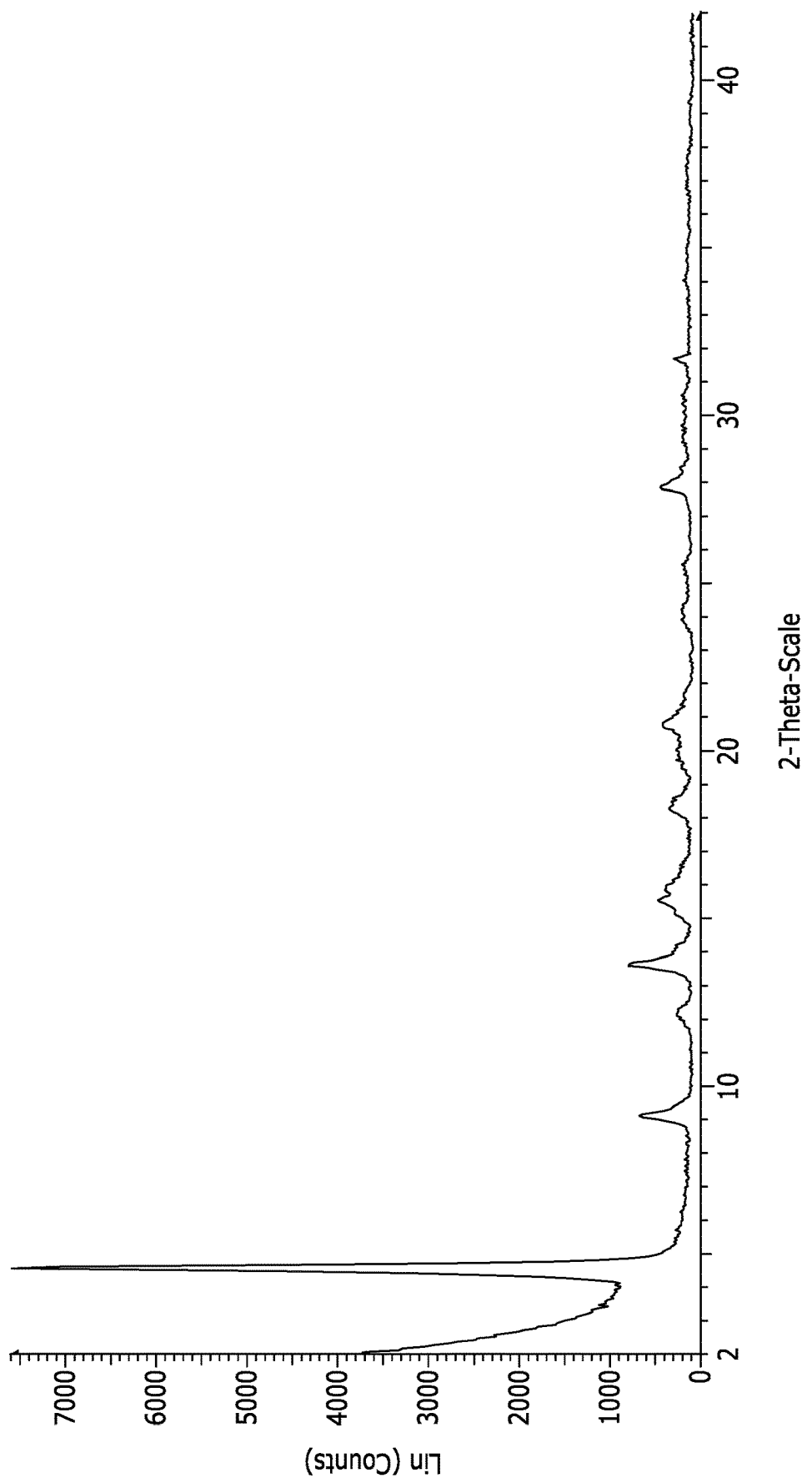
FIG. 39 shows an X-ray powder diffractogram (XRPD) of a magnesium salt of fospropofol.

In some embodiments, the magnesium salt of fospropofol has an XRPD substantially as shown in FIG. 39. The XRPD of the magnesium salt of fospropofol shown in FIG. 39 comprises reflection angles (degrees 2-theta±0.2 degrees 2-theta), and relative intensities as shown in Table 14:

TABLE 14

XRPD Data for magnesium salt of Fospropofol

| Angle (degrees 2-theta ± 0.2 degrees 2-theta) | Relative Intensity |
| --- | --- |
| 4.5 | 100.0 |
| 9.1 | 8.8 |
| 12.2 | 3.5 |
| 13.6 | 10.3 |
| 15.5 | 6.2 |
| 18.3 | 4.8 |
| 20.8 | 5.9 |
| 24.1 | 3.2 |

TABLE 14-continued

XRPD Data for magnesium salt of Fospropofol

| Angle (degrees 2-theta ± 0.2 degrees 2-theta) | Relative Intensity |
|---|---|
| 27.9 | 5.9 |
| 31.7 | 3.9 |

In some embodiments of the present disclosure, the magnesium salt of fospropofol is characterized by an XRPD pattern comprising a peak at one of the angles listed in Table 14. In other aspects, the magnesium salt of fospropofol is characterized by an XRPD pattern comprising more than one peak at one of the angles listed in Table 14 above. In other aspects, the magnesium salt of fospropofol is characterized by an XRPD pattern comprising two peaks selected from the angles listed in Table 14 above. In other aspects, the magnesium salt of fospropofol is characterized by an XRPD pattern comprising three peaks selected from the angles listed in Table 14 above. In other aspects, the magnesium salt of fospropofol is characterized by an XRPD pattern comprising four peaks selected from the angles listed in Table 14 above. In other aspects, the magnesium salt of fospropofol is characterized by an XRPD pattern comprising five peaks selected from the angles listed in Table 14 above. In other aspects, the magnesium salt of fospropofol is characterized by an XRPD pattern comprising six peaks selected from the angles listed in Table 14 above. In other aspects, the magnesium salt of fospropofol is characterized by an XRPD pattern comprising seven peaks selected from the angles listed in Table 14 above. In other aspects, the magnesium salt of fospropofol is characterized by an XRPD pattern comprising eight peaks selected from the angles listed in Table 14 above. In other aspects, the magnesium salt of fospropofol is characterized by an XRPD pattern comprising nine peaks selected from the angles listed in Table 14 above. In other aspects, the magnesium salt of fospropofol is characterized by an XRPD pattern comprising ten peaks selected from the angles listed in Table 14 above. In other aspects, the magnesium salt of fospropofol is characterized by an XRPD pattern comprising more than ten peaks selected from the angles listed in Table 14 above.

In some embodiments, the magnesium salt of fospropofol is characterized by an XRPD pattern comprising a peak at 4.5 degrees±0.2 degrees 2-theta. In other embodiments, the magnesium salt of fospropofol is characterized by an XRPD pattern comprising peaks at 4.5, 9.1, and 13.6 degrees±0.2 degrees 2-theta. In other embodiments, the magnesium salt of fospropofol is characterized by an XRPD pattern comprising peaks at 4.5, 9.1, 13.6, and 20.8 degrees±0.2 degree 2-theta. In yet other embodiments, the magnesium salt of fospropofol is characterized by an XRPD pattern comprising peaks at 4.5, 9.1, 13.6, 20.8, and 27.9 degrees±0.2 degree 2-theta.

In some embodiments of the present disclosure, the magnesium salt of fospropofol is characterized by an XRPD pattern comprising peaks at two or more of 4.5, 9.1, 13.6, 20.8, and 27.9 degrees±0.2 degrees 2-theta. In some embodiments of the present disclosure, the magnesium salt of fospropofol is characterized by an XRPD pattern comprising peaks at three or more of 4.5, 9.1, 13.6, 20.8, and 27.9 degrees±0.2 degrees 2-theta. In some embodiments of the present disclosure, the magnesium salt of fospropofol is characterized by an XRPD pattern comprising peaks at four or more of 4.5, 9.1, 13.6, 20.8, and 27.9 degrees±0.2 degrees 2-theta.

Figure 40:
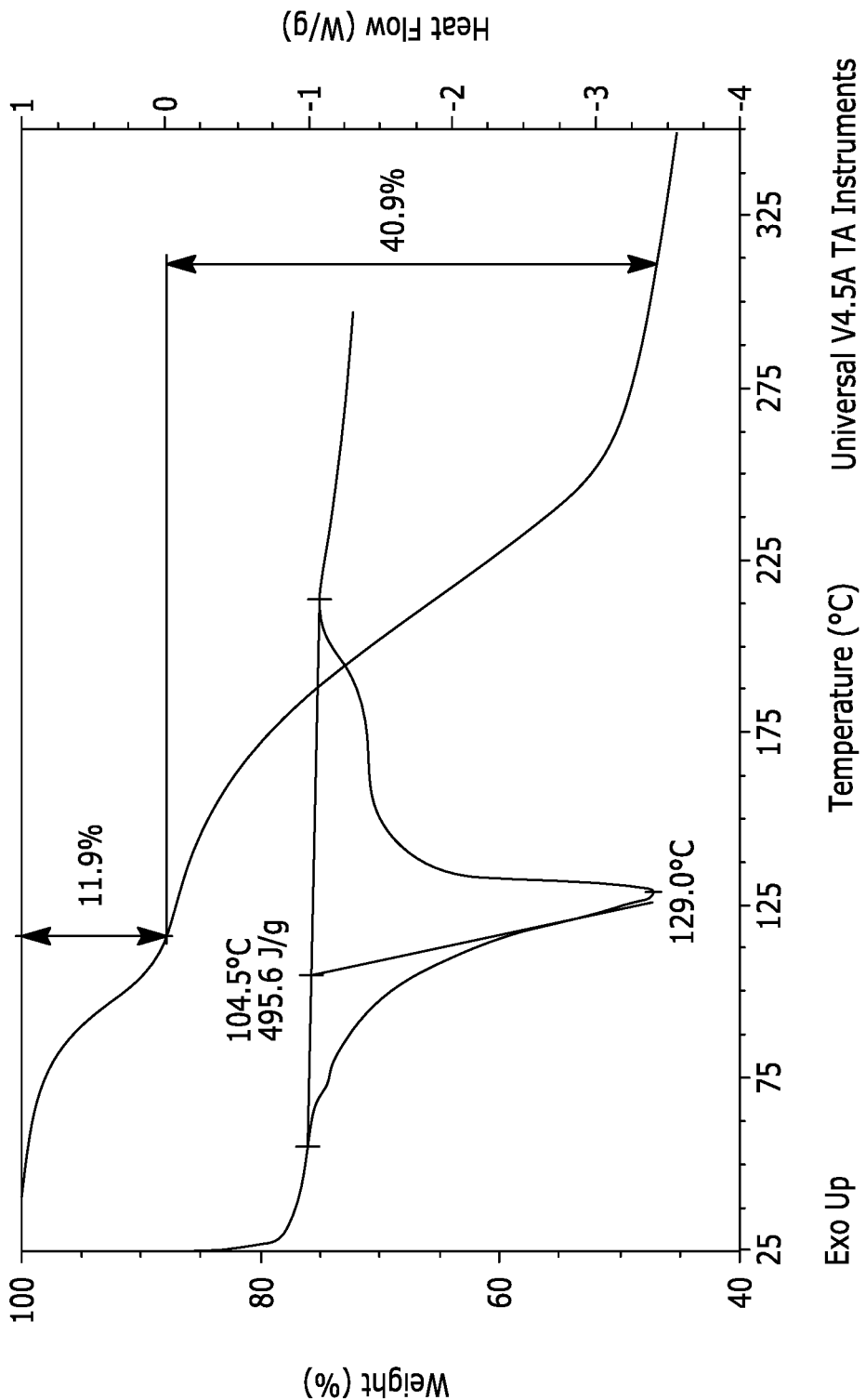
FIG. 40 shows a differential scanning calorimetry (DSC) profile and a thermogravimetric analysis profile (TGA) of a magnesium salt of fospropofol.

In some embodiments, the magnesium salt of fospropofol can be characterized by a DSC thermogram substantially as shown in FIG. 40. As FIG. 40 shows, the magnesium salt of fospropofol produced an endothermic peak at 129.0° C. when heated at a rate of 10° C./min. In some embodiments of the present disclosure, the magnesium salt of fospropofol is characterized by a DSC thermogram comprising an endothermic peak at about 129° C. when heated at a rate of 10° C./min.

In other embodiments, the magnesium salt of fospropofol can be characterized by a TGA profile substantially as shown in FIG. 40. As FIG. 40 shows, the magnesium salt of fospropofol lost about 12% of its weight upon heating to 125° C., and about 41% of its weight upon heating to 325° C. a rate of 10° C./min.

In some embodiments of the present disclosure, the magnesium salt of fospropofol is characterized by an XRPD pattern comprising peaks at 4.5, 9.1, 13.6, 20.8, and 27.9 degrees±0.2 degrees 2-theta, and a DSC thermogram comprising an endothermic peak at about 129° C. when heated at a rate of 10° C./min.

In some embodiments, the pharmaceutically acceptable salt of fospropofol is the zinc salt.

Figure 41:
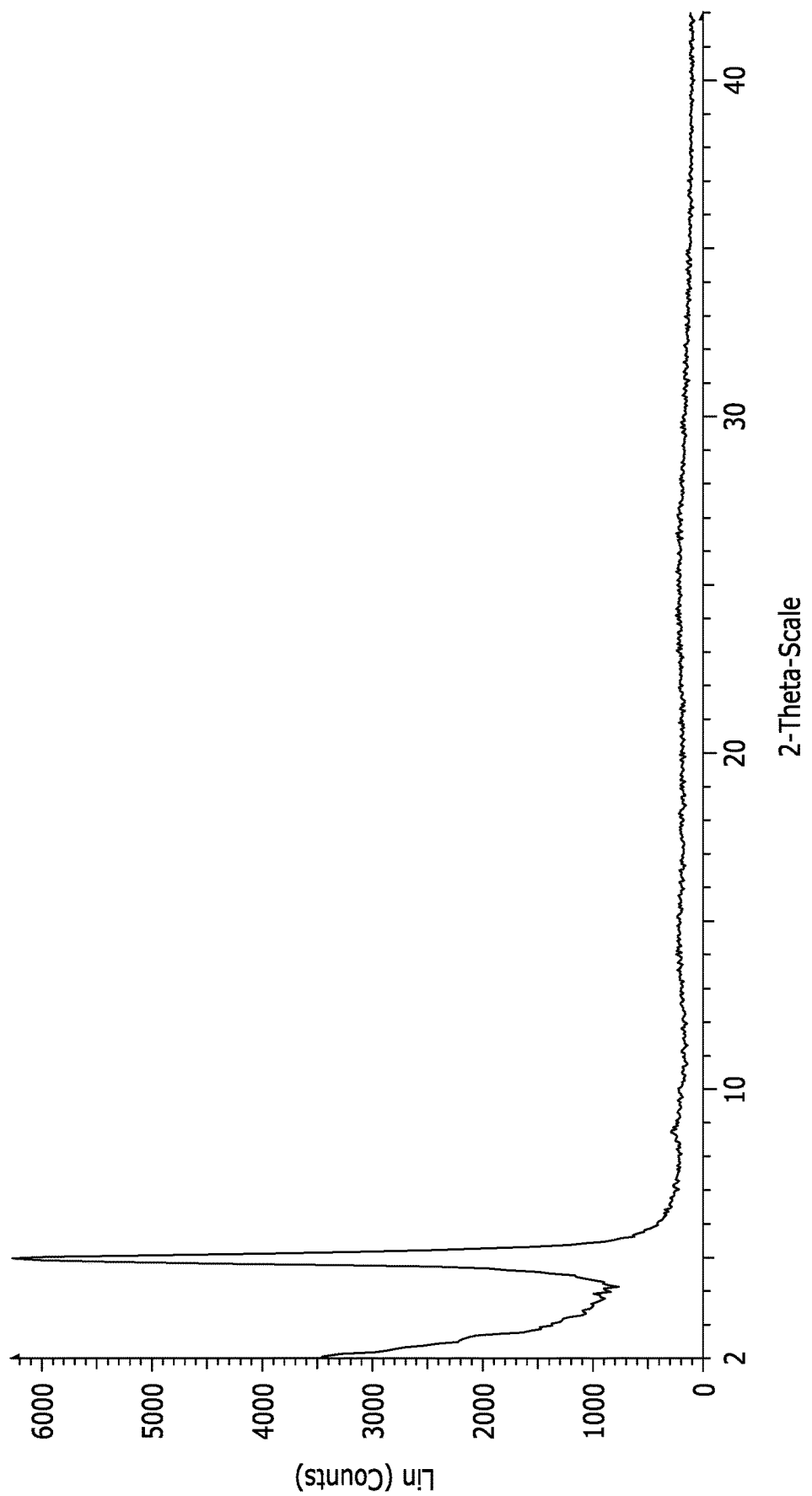
FIG. 41 shows an X-ray powder diffractogram (XRPD) of a zinc salt of fospropofol (Form II).

In some embodiments, the zinc salt of fospropofol (Form II) has an XRPD substantially as shown in FIG. 41. Form II of the zinc salt has a single peak at 4.9 degrees 2-theta±0.2 degrees 2-theta.

Figure 42:
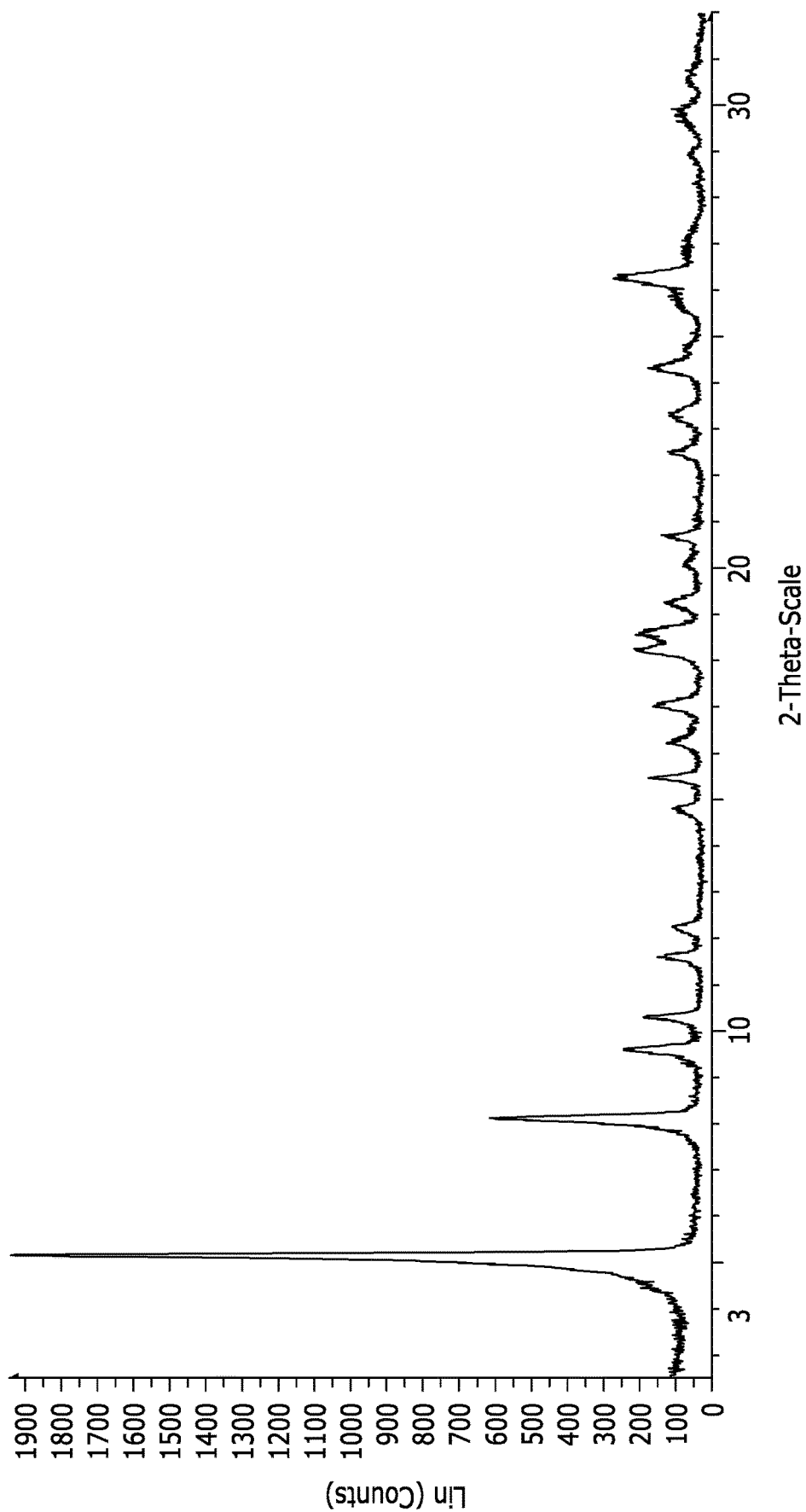
FIG. 42 shows an X-ray powder diffractogram (XRPD) of a zinc salt of fospropofol (Form I).

In some embodiments, the zinc salt of fospropofol (Form I) has an XRPD substantially as shown in FIG. 42. The XRPD of the Form I zinc salt of fospropofol shown in FIG. 42 comprises reflection angles (degrees 2-theta±0.2 degrees 2-theta), and relative intensities as shown in Table 15:

TABLE 15

XRPD Data for Form I zinc salt of Fospropofol

| Angle (degrees 2-theta ± 0.2 degrees 2-theta) | Relative Intensity |
|---|---|
| 5.1 | 100.0 |
| 8.1 | 32.0 |
| 9.6 | 12.5 |
| 10.3 | 9.7 |
| 11.6 | 7.5 |
| 12.2 | 5.7 |
| 14.8 | 5.7 |
| 15.5 | 9.2 |
| 16.2 | 6.3 |
| 17.0 | 8.2 |
| 18.2 | 10.9 |
| 18.6 | 10.5 |
| 19.2 | 6.0 |
| 20.1 | 4.3 |
| 20.7 | 6.5 |
| 22.5 | 5.7 |
| 23.3 | 6.2 |
| 24.3 | 8.9 |
| 26.3 | 13.8 |

In some embodiments of the present disclosure, the Form I zinc salt of fospropofol is characterized by an XRPD pattern comprising a peak at one of the angles listed in Table 15. In other aspects, the zinc salt of fospropofol is characterized by an XRPD pattern comprising more than one peak at one of the angles listed in Table 15 above. In other aspects, the zinc salt of fospropofol is characterized by an XRPD pattern comprising two peaks selected from the angles listed in Table 15 above. In other aspects, the zinc salt of fospropofol is characterized by an XRPD pattern comprising three peaks selected from the angles listed in Table 15 above.

In other aspects, the zinc salt of fospropofol is characterized by an XRPD pattern comprising four peaks selected from the angles listed in Table 15 above. In other aspects, the zinc salt of fospropofol is characterized by an XRPD pattern comprising five peaks selected from the angles listed in Table 15 above. In other aspects, the zinc salt of fospropofol is characterized by an XRPD pattern comprising six peaks selected from the angles listed in Table 15 above. In other aspects, the zinc salt of fospropofol is characterized by an XRPD pattern comprising seven peaks selected from the angles listed in Table 15 above. In other aspects, the zinc salt of fospropofol is characterized by an XRPD pattern comprising eight peaks selected from the angles listed in Table 15 above. In other aspects, the zinc salt of fospropofol is characterized by an XRPD pattern comprising nine peaks selected from the angles listed in Table 15 above. In other aspects, the zinc salt of fospropofol is characterized by an XRPD pattern comprising ten peaks selected from the angles listed in Table 15 above. In other aspects, the zinc salt of fospropofol is characterized by an XRPD pattern comprising more than ten peaks selected from the angles listed in Table 15 above.

In some embodiments, the Form I zinc salt of fospropofol is characterized by an XRPD pattern comprising a peak at 8.1, 9.6, and 10.3 degrees±0.2 degrees 2-theta. In other embodiments, the zinc salt of fospropofol is characterized by an XRPD pattern comprising peaks at 18.2, 18.6, and 26.3 degrees±0.2 degrees 2-theta. In other embodiments, the zinc salt of fospropofol is characterized by an XRPD pattern comprising peaks at 8.1, 9.6, 10.3, 11.6, and 12.2 degrees±0.2 degree 2-theta. In yet other embodiments, the zinc salt of fospropofol is characterized by an XRPD pattern comprising peaks at 5.1, 8.1, 9.6, 10.3, 11.6, 12.2, 18.2, 18.6, and 26.3 degrees±0.2 degree 2-theta.

In some embodiments of the present disclosure, the Form I zinc salt of fospropofol is characterized by an XRPD pattern comprising peaks at three or more of 5.1, 8.1, 9.6, 10.3, 11.6, 12.2, 18.2, 18.6, and 26.3 degrees±0.2 degrees 2-theta. In some embodiments of the present disclosure, the zinc salt of fospropofol is characterized by an XRPD pattern comprising peaks at four or more of 5.1, 8.1, 9.6, 10.3, 11.6, 12.2, 18.2, 18.6, and 26.3 degrees±0.2 degrees 2-theta. In some embodiments of the present disclosure, the zinc salt of fospropofol is characterized by an XRPD pattern comprising peaks at five or more of 5.1, 8.1, 9.6, 10.3, 11.6, 12.2, 18.2, 18.6, and 26.3 degrees±0.2 degrees 2-theta. In some embodiments of the present disclosure, the zinc salt of fospropofol is characterized by an XRPD pattern comprising peaks at six or more of 5.1, 8.1, 9.6, 10.3, 11.6, 12.2, 18.2, 18.6, and 26.3 degrees±0.2 degrees 2-theta. In some embodiments of the present disclosure, the zinc salt of fospropofol is characterized by an XRPD pattern comprising peaks at seven or more of 5.1, 8.1, 9.6, 10.3, 11.6, 12.2, 18.2, 18.6, and 26.3 degrees±0.2 degrees 2-theta.

Figure 43:
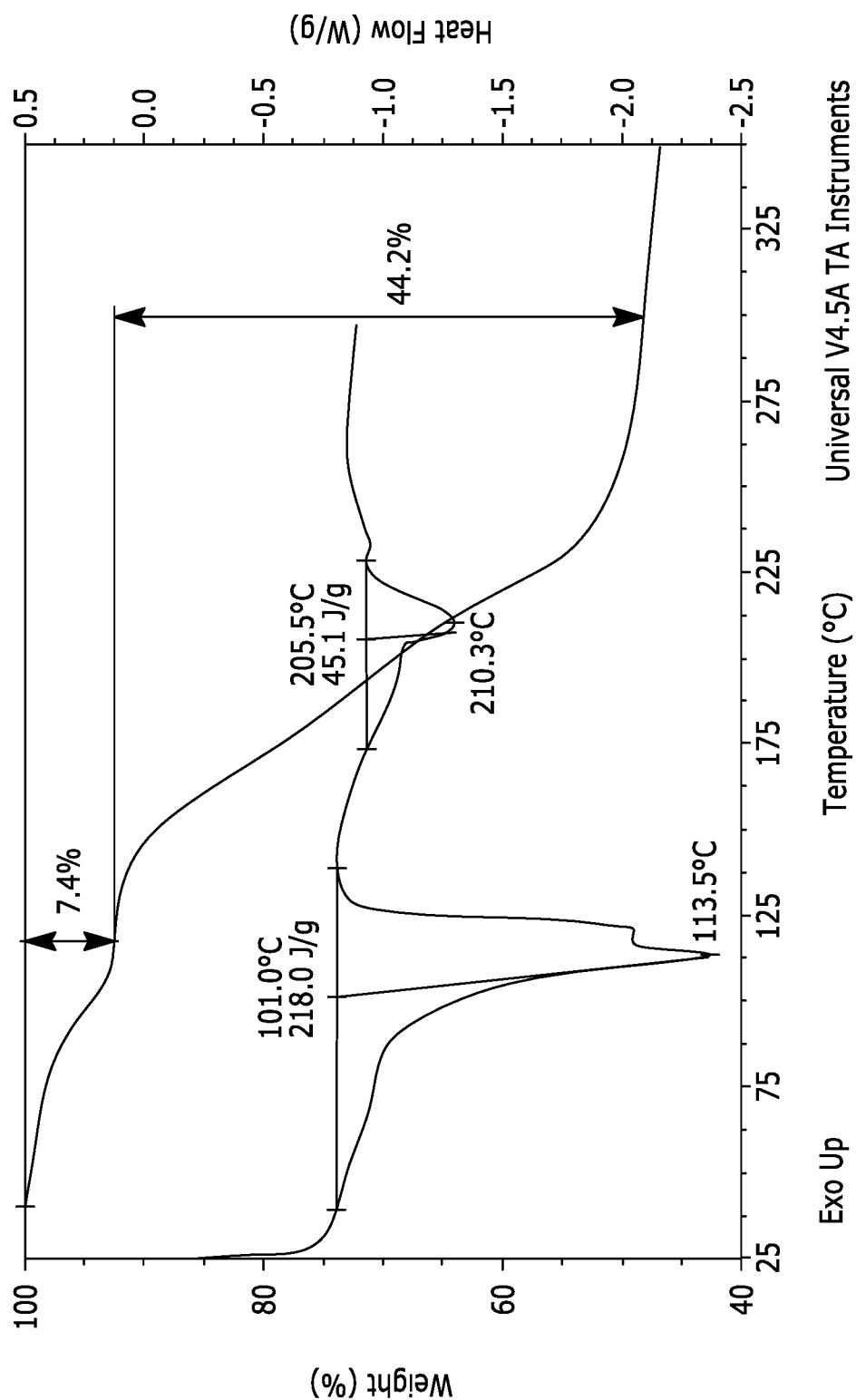
FIG. 43 shows a differential scanning calorimetry (DSC) profile and a thermogravimetric analysis profile (TGA) of a zinc salt of fospropofol (Form I).

The Form I zinc salt of fospropofol can be characterized by a DSC thermogram substantially as shown in FIG. 43. As FIG. 43 shows, the zinc salt of fospropofol produced an endothermic peaks at 113.5° C. and 210.3° C. when heated at a rate of 10° C./min. In some embodiments of the present disclosure, the zinc salt of fospropofol is characterized by a DSC thermogram comprising endothermic peaks at about 114° C. or about 210° C. when heated at a rate of 10° C./min.

In other embodiments, the Form I zinc salt of fospropofol can be characterized by a TGA profile substantially as shown in FIG. 43. As FIG. 43 shows, the magnesium salt of fospropofol lost about 7.4% of its weight upon heating to 125° C., and about 44% of its weight upon heating to 325° C. a rate of 10° C./min.

In some embodiments of the present disclosure, the Form I zinc salt of fospropofol is characterized by an XRPD pattern comprising peaks at 5.1, 8.1, 9.6, 10.3, 11.6, 12.2, 18.2, 18.6, and 26.3 degrees±0.2 degrees 2-theta, and a DSC thermogram comprising endothermic peaks at 114° C. and 210° C. when heated at a rate of 10° C./min.

Methods of Use

In some aspects, the present disclosure is directed to methods of treating migraine in a patient in need thereof, comprising administering to said patient an effective amount of a pharmaceutically acceptable salt of fospropofol wherein the pharmaceutically acceptable salt is a potassium, diethyl amine, t-butyl amine, ethylene diamine, benzathine, piperazine, ethanolamine, diethanolamine, ammonium, tromethamine, benethamine, histidine, calcium, magnesium, or zinc salt.

In some embodiments, the patient's migraine is migraine with aura. Migraine with aura (also referred to as classic migraine) is characterized by focal neurological symptoms that typically precede, or sometimes accompany, the headache.

In other embodiments, the patient's migraine is migraine without aura. Migraine without aura (also referred to as common migraine) is characterized by the absence of focal neurological symptoms that typically precede, or sometimes accompany, the headache.

In other embodiments, the patient's migraine is cluster headache.

In other embodiments, the patient's migraine is intractable migraine.

In some embodiments of the disclosed methods, the patient's migraine is refractory migraine.

Refractory migraine may fail to respond one or more types of pharmacologic treatment. Examples of pharmacologic treatment to which refractory migraine may fail to respond include CGRP inhibitors (e.g., gepants, including Ubrogepant (MK-1602) and Rimegepant (BMS-927711); anti-CGRP antibodies such as Aimovig® (erenumab), a IgG2 humanized monoclonal antibody; Emgaliyt® Galcanezumab, an IgG4 Kappa-chain dimer monoclonal antibody; and Ajovy® (fremanezumab), an IgG2 Δa/kappa humanized monoclonal antibody), triptans (e.g., sumatriptan (Imitrex), rizatriptan (Maxalt), almotriptan (Axert), naratriptan (Amerge), zolmitriptan (Zomig), frovatriptan (Frova) and eletripan (Relpax)), antidepressant and mood stabilizers (e.g., Amitriptyline), anticonvulsants and mood stabilizers (e.g., Topiramate, Valproate, and Gabapentin), and NSAIDS (e.g., diclofenac and ketorolac).

In some embodiments of the disclosed methods, the patient's refractory migraine may fail to respond to CGRP inhibitors, and is referred to as CGRP inhibitor-refractory migraine.

In some embodiments, the patient's CGRP-inhibitor refractory migraine fails to respond to gepant treatment, and is referred to as gepant-refractory migraine. In other embodiments, the patient's CGRP-inhibitor refractory migraine fails to respond to anti-CGRP antibodies, and is referred to as anti-CGRP antibody-refractory migraine.

In other embodiments of the disclosed methods, the patient's refractory migraine may fail to respond to triptans, and is referred to as triptan-refractory migraine.

In other embodiments of the disclosed methods, the patient's refractory migraine may fail to respond to NSAIDs and is referred to as NSAID-refractory migraine.

In other embodiments of the disclosed methods, the patient's refractory migraine may fail to respond to dihydroergotamine (DHE) and is referred to as DHE-refractory migraine.

In other embodiments, the patient's migraine is catamenial migraine.

In some aspects, the methods of the disclosure are directed to treating migraine in a patient in need thereof. The methods of the disclosure, therefore, are performed on patients suffering from migraine.

In some embodiments, the patient is a mammal.

In other embodiments, the patient is a human.

In some embodiments, the patient is female.

In other embodiments, the patient is male.

In some embodiments, the patient is 18 years of age or older.

In other embodiments, the patient is between 6 and 17 years of age.

In other embodiments, the patient is less than 6 years of age.

In some embodiments, the patient was diagnosed with migraine at least one year prior to being administered fospropofol in accordance with the disclosed methods.

In some embodiments, the administering is oral.

In some embodiments, the administering is peroral.

In other embodiments, the administering is subcutaneous.

In other embodiments, the administering is intramuscular.

In other embodiments, the administering is intravenous.

In other embodiments, the administering is rectal.

Pharmaceutical Compositions

In some aspects, the disclosure is directed to pharmaceutical compositions comprising a pharmaceutically acceptable salt of fospropofol wherein the pharmaceutically acceptable salt is a potassium, diethyl amine, t-butyl amine, ethylene diamine, benzathine, piperazine, ethanolamine, diethanolamine, ammonium, tromethamine, benethamine, histidine, calcium, magnesium, or zinc salt, or mixtures thereof, and a pharmaceutically acceptable excipient.

In some embodiments, the pharmaceutical composition is a solid.

In other embodiments, the pharmaceutical composition is a liquid.

In other embodiments, the pharmaceutical composition is a suspension.

The pharmaceutical compositions of the present disclosure may take any physical form suitable for the mode of administration.

In some embodiments, the physical form of the pharmaceutical composition is a capsule (gelatin or non-gelatin), enteric capsules, cachets, tablets, beads, or powders.

In some embodiments, the physical form of the pharmaceutical composition is coated beads.

In other embodiments, the physical form of the pharmaceutical composition is tablets.

In some embodiments, the physical form of the pharmaceutical composition is coated tablets.

In some embodiments, the physical form of the pharmaceutical composition is enteric coated tablets.

In some embodiments, the physical form of the pharmaceutical composition is multilayer tablets.

In some embodiments, the physical form of the pharmaceutical composition is multilayer coated tablets.

In some embodiments, the physical form of the pharmaceutical composition is coated multilayer uncoated tablets.

In some embodiments, the physical form of the pharmaceutical composition is a tablet within a tablet.

In some embodiments, the physical form of the pharmaceutical composition is a capsule.

In some embodiments, the physical form of the pharmaceutical composition is a capsule containing pellets or beads.

In some embodiments, the physical form of the pharmaceutical composition is a capsule containing pellets or beads, wherein the pellets or beads are heterogenous with respect to release of fospropofol.

In some embodiments, the physical form of the pharmaceutical composition is a capsule containing tablets, wherein the tablets are heterogenous with respect to release of fospropofol.

In other embodiments, the physical form of the pharmaceutical composition is a gel, water soluble jellies, creams, lotions, suspensions, foams, powders, slurries, ointments, solutions, oils, pastes, suppositories, sprays, or emulsions.

In some embodiments, the physical form of the pharmaceutical composition is a modified release dosage form.

In some aspects, the pharmaceutical compositions of the disclosure comprises a pharmaceutically acceptable excipient.

In some embodiments, the pharmaceutically acceptable excipient may be water, glycols, oils, alcohols, flavoring agents, preservatives, coloring agents, starches, sugars, micro-crystalline cellulose, surfactants, polymers, diluents, granulating agents, lubricants, binders, fillers, and disintegrants.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, dicalcium phosphate, hydroxypropyl methyl cellulose, microcrystalline cellulose, and mixtures thereof.

Fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, dicalcium phosphate, pre-gelatinized starch, and mixtures thereof.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof.

In some embodiments, the solid pharmaceutical dosage form is uncoated or coated to delay disintegration and absorption in the gastrointestinal tract. For example, a time delay material such as glyceryl monostearate or glyceryl distearate can be employed.

Surfactant which can be used to form pharmaceutical compositions and dosage forms of the invention include, but are not limited to, hydrophilic surfactants, lipophilic surfactants, ionic surfactants, and mixtures thereof.

Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof, lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phytol sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof.

Solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-allylpiperidine, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Release modifiers may include coatings or matrix materials.

Release modifying coatings include but are not limited to polymer coating materials, such as cellulose acetate phthalate, cellulose acetate trimaleate, hydroxy propyl methylcellulose phthalate, polyvinyl acetate phthalate, ammonio methacrylate copolymers such as those sold under the Trade Mark Eudragit® RS and RL, poly acrylic acid and poly acrylate and methacrylate copolymers such as those sold under the Trade Mark Eudragite S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based cross-linked polymers—in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, aminoacyl-methacrylate copolymer (Eudragit® RS-PM, Rohm & Haas), pullulan, collagen, casein, agar, gum arabic, sodium carboxymethyl cellulose, (swellable hydrophilic polymers) poly(hydroxyalkyl methacrylate) (m. wt. ~5 k-5,000 k), polyvinylpyrrolidone (m. wt. ~10 k-360 k), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (m. wt. ~30 k-300 k), polysaccharides such as agar, acacia, karaya, tragacanth, algins and guar, polyacrylamides, Polyox® polyethylene oxides (m. wt. ~100 k-5,000 k), AquaKeep® acrylate polymers, diesters of polyglucan, crosslinked polyvinyl alcohol and poly N-vinyl-2-pyrrolidone, sodium starch glucolate (e.g. Explotab®; Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. Polyox®, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. Eudragit®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof. As will be appreciated by the person skilled in the art, excipients such as plasticisers, lubricants, solvents and the like may be added to the coating. Suitable plasticisers include for example acetylated monoglycerides; butyl phthalyl butyl glycolate; dibutyl tartrate; ethyl phthalyl ethyl glycolate; glycerin; propylene glycol; triacetin; citrate; tripropionin; diacetin; acetyl monoglyceride; polyethylene glycols; castor oil; triethyl citrate; polyhydric alcohols, glycerol, acetate esters, gylcerol triacetate, acetyl triethyl citrate, dioctyl azelate, epoxidised tallate, triisooctyl trimellitate, tri-2-ethylhexyl trimellitate, di-2-ethylhexyl adipate, di-2-ethylhexyl sebacate, di-2-ethylhexyl azelate, dibutyl sebacate.

Release-modifying matrix materials include hydrophilic polymers, hydrophobic polymers and mixtures thereof, dicalcium phosphate, microcrystalline cellulose, sodium carboxymethylcellulose, hydroxyalkylcelluloses such as hydroxypropylmethylcellulose and hydroxypropylcellulose, polyethylene oxide, alkylcelluloses such as methylcellulose and ethylcellulose, polyethylene glycol, polyvinylpyrrolidone, cellulose acetate, cellulose acetate butyrate, cellulose acetate phthalate, cellulose acetate trimellitate, polyvinylacetate phthalate, polyalkylmethacrylates, polyvinyl acetate, Poly(2-hydroxy ethyl methacrylate), Poly(N-vinyl pyrrolidone), Poly(methyl methacrylate), Poly(vinyl alcohol), Poly (acrylic acid), Polyacrylamide, Poly(ethylene-co-vinyl acetate), Poly(ethylene glycol), Poly(methacrylic acid), Polylactides (PLA), Polyglycolides (PGA), Poly(lactide-co-glycolides) (PLGA), Polyanhydrides, and Polyorthoesters, and mixture thereof.

EXAMPLES

Example 1

Instrumental Methods

XRPD diffractograms were collected on a Bruker D8 diffractometer using Cu Kα radiation (40 kV, 40 mA) and a 0-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder. The sample was prepared on a polished, zero-background (510) silicon wafer by gently pressing onto the flat surface or packed into a cut cavity. The sample was rotated in its own plane. The details of the standard Pharmorphix data collection method are:
  Angular range: 2 to 42° 2θ
  Step size: 0.05° 2θ
  Collection time: 0.5 s/step (total collection time: 6.40 min)

XRPD diffractograms were also collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel30 detector, placed on the diffracted beam, was fitted with a receiving slit and 0.04 rad Soller slits. The software used for data collection was X'Pert Data Collector using X'Pert Operator Interface. The data were analysed and presented using Diffrac Plus EVA or HighScore Plus.

Samples were prepared and analysed in either a metal or Millipore 96 well-plate in transmission mode. X-ray transparent film was used between the metal sheets on the metal well-plate and powders (approximately 1-2 mg) were used. The Millipore plate was used to isolate and analyse solids from suspensions by adding a small amount of suspension directly to the plate before filtration under a light vacuum. The scan mode for the metal plate used the gonio scan axis, whereas a 2θ scan was utilised for the Millipore plate. The details of the standard screening data collection method are:
  Angular range: 2.5 to 32.0° 2θ
  Step size: 0.0130° 2θ
  Collection time: 12.75 s/step (total collection time of 2.07 min)

Solution State NMR $^1$H NMR and/or $^{13}$C NMR spectra were collected on a Bruker 400 MHz instrument equipped with an auto-sampler and controlled by a DRX400 console. Samples were prepared in DMSO-$d_6$ solvent, unless otherwise stated. Automated experiments were acquired using ICON-NMR configuration within Topspin software, using standard Bruker-loaded experiments ($^1$H, $^{13}$C $\{^1$H$\}$, DEPT135). Off-line analysis was performed using ACD Spectrus Processor.

Differential Scanning Calorimetry (DSC)

DSC data were collected on a TA Instruments Q2000 equipped with a 50 position auto-sampler. Typically, 0.5-3 mg of each sample, in a pin-holed aluminium pan, was heated at 10° C./min from 25° C. to 300° C. A purge of dry nitrogen at 50 ml/min was maintained over the sample. The instrument control software was Advantage for Q Series and Thermal Advantage and the data were analysed using Universal Analysis or TRIOS.

Thermal Gravimetric Analysis

TGA data were collected on a TA Instruments Discovery TGA, equipped with a 25 position auto-sampler. Typically, 5-10 mg of each sample was loaded onto a pre-tared aluminium DSC pan and heated at 10° C./min from ambient temperature to 350° C. A nitrogen purge at 25 ml/min was maintained over the sample. The instrument control software was TRIOS and the data were analysed using TRIOS or Universal Analysis.

Example 2

Preparation of Fospropofol
Procedure 1

Fospropofol disodium (100 mg, ±1 mg) was weighed into 3 HPLC vials and dissolved in water (5 vol. 0.5 ml) at RT. Hydrochloric acid, sulfuric acid or phosphoric acid (2.1 eq. 1 M in THF) was added to the samples and stirred for 5 minutes and no solids were observed. Samples were cooled to 5° C. and still no solids were observed. The sample containing hydrochloric acid was selected to extract the product using DCM (3× extraction with 0.5 ml DCM). The organic layers were collected and concentrated under rotary evaporator at 50° C. resulting in a clear colourless oil. This oil was analysed by 1H NMR, HPLC and scanning ion chromatography.

Procedure 2

Fospropofol disodium (2.0 g) was dissolved in water (5 vol) at RT. Once a clear solution was obtained HCl (2.1 eq., 0.5 Min water) was added and a cloudy solution was formed. The sample was transferred to a separating funnel and DCM (30 ml) added to extract the free acid but instead formed a thick white emulsion with no phase separation. DCM (130 ml) was added to try and increase phase separation and water (100 ml) was added to solubilise any NaCl precipitating out of solution. The thick white emulsion remained so THF was added to disrupt the emulsion, resulting in separation of the aqueous and organic phases both cloudy solutions. The organic layer was collected and the aqueous layer washed with THF:DCM 25:75 (2×40 ml). The organic layer was concentrated under vacuum resulting in a clear oil.

Example 3

The following procedure was used to make the potassium (from KOH), diethylamine, t-butylamine, ethylene diamine, benzathine, piperazine, ethanolamine, diethanolamine, ammonium (from $NH_4OH$), tromethamine, benethamine, and histidine salts.

Fospropofol free acid (25 mg) was dissolved in EtOH (20 vol, 500 µl) at RT. The solutions were treated with the corresponding base (2 mol eq., added as a stock solution) at 25° C. After 10 minutes at 25° C., the mixtures were cooled to 5° C. at 0.1° C./min. After 48 hrs at 5° C. solids were filtered, air dried and analysed by XRPD, solutions were allowed to evaporate at RT. Solids formed from evaporation were analysed by XRPD, gums and oils were placed under vacuum for 3 hours. Solids were analysed by XRPD and remaining gums and oils matured at 50° C./RT in 4 hours temperature cycles for 48 hrs.

XRPD was again taken after 7 days storage at 40° C./75% RH. Form II of the diethylamine salt and Form II of the ethanolamine salt were formed by conversion of Form I of the respective salts after 7 days storage at 40° C./75% RH.

Example 4

The following procedures were used to make the calcium (from $CaCl_2$), magnesium (from $MgCl_2$), and zinc ($ZnCl_2$) salts.

Small Scale: Fospropofol disodium (50 mg) was dissolved in water (10 vol, 500 µl). The solutions were treated with the corresponding base (1 mol eq., added as a stock solution). Additional ethanol (500 µl) was added after the formation of a thick suspension and samples stirred for 1 hour before being filtered and dried in a vacuum oven for 2 hours at 40° C. Form I of the calcium salt and Form I of the zinc salt were produced under these conditions.

Form II of the calcium salt was produced from Form I of the calcium salt after 7 days storage at 40° C./75% RH.

Scale Up: Fospropofol disodium (500 mg) was dissolved in water (10 vol, 5 ml). The solutions were treated with the corresponding base (1 mol eq. $CaCl_2$, $MgCl_2$, or $ZnCl_2$). Additional ethanol* (5 ml) was added after the formation of a thick suspension and samples stirred for 1 hour before being filtered and dried in a vacuum oven for 2 hours at 40° C. *ethanol (5 ml) was added three times for the sample containing the calcium counter ion as thick precipitate continued to stop stirring. This procedure produced Form III of the calcium salt and Form II of the zinc salt. Ion chromatography of the product salts indicated that the calcium and magnesium salts each contained 1 eq. of the metal counterion, and the zinc salt contained 2 eq. of the metal counterion.

Example 5

Preparation of Ethylene Diamine Salt

The free acid (500 mg) was dissolved in EtOH (20 vol, 10 ml) at 50° C. The solution was treated with ethylene diamine (2 mol eq.) at 50° C. The sample was cooled to 5° C. at 0.1° C./min. After 48 hrs at 5° C. solids were filtered and dried in a vacuum oven for 2 hours at 40° C.

Example 6—Intrinsic Dissolution Rate at pH 4.5

Intrinsic Dissolution Rate was measure in GI tract buff (pH—4.5 buffer): 2.99 g sodium acetate trihydrate was dissolved in 14.0 ml 2N acetic acid in a 1000 ml volumetric flask, and then made to volume with deionised water.

Data were collected on a Sirius inform instrument fitted with a dual UV DipProbe attachment and Ag/AgCl combination pH electrode. The electrode was calibrated using the four plus parameters derived from a blank titration. The base titrant was standardised by titration with TRIS. 0.5 M HCl and NaOH aqueous solutions were used as the acid and base titrants respectively for the testing. Stirring was facilitated by a dual overhead stirrer to allow thorough mixing within the vessel, and media was introduced via a capillary bundle attached to a dispensing bank comprised of six precision dispensing units. A Peltier heating jacket was used to maintain the temperature of the titration vessel. Discs were introduced to the vessel via the tablet picker housed in the probe arm, after the desired temperature of the media had been reached. Sirius inform Assay Design, Control and Refine software were used to design, run and refine data respectively.

The reference sample was prepared as a 20.1 mM stock solution in water. One MEC data sets were then collected using five additions each of the water stock using 250, 500 and three times 750 µl aliquots, respectively. UV Spectra were then collected after each addition of the water stock to build a multi-point MEC calibration, using a 20 mm path length probe. The MEC data set was then imported into the dissolution data files in order to convert the UV absorbance measured to concentration. The concentration range for UV data collected was 124.8 µM-1.4 mM. MEC data were collected at 37° C. to match the dissolution experiments. Same MEC data was used as for faSSGf IDR experiments due to there being no change in the UV profile at this pH.

Intrinsic Dissolution Rate (IDR): Approximately. 10-20 mg of the sample was compressed in a 3 mm disc recess, under 100 kg for 2 minutes, with greaseproof paper on the compression base, to form nondisintegrating discs. The discs were then plugged with a bung so that only one surface was exposed to the media during analysis and transferred to the Sirius inform dissolution apparatus. Analysis was performed at 37° C. in 36 ml water and 4 ml GI media with the pH set to 4.5, for 1 hour with UV spectra collected every 10 seconds. A stir speed of 100 rpm was used with a 20 mm path length probe. The IDR was calculated based on the surface area of the 3 mm disc recess used (7.07 mm2 surface area). XRPD analysis was performed on all samples, both after compression of the material into the disc recess, and post dissolution analysis to observe any change in form. All analysis was performed using XRPD 2.

X-Ray Powder Diffraction (XRPD2): XRPD diffractograms were collected on a Bruker AXS C2 GADDS diffractometer using Cu Ka radiation (40 kV, 40 mA), an automated XYZ stage, a laser video microscope for auto sample positioning and a Vantec-500 2-dimensional area detector. X-ray optics consists of a single Gobel multilayer mirror coupled with a pinhole collimator of 0.3 mm. The beam divergence, i.e. the effective size of the X-ray beam on the sample, was approximately 4 mm. A 9-9 continuous scan mode was employed with a sample—detector distance of 20 cm which gives an effective 2θ range of 1.5°-32.5°. The sample was exposed to the X-ray beam for 120 seconds under ambient conditions. The software used for data collection and analysis was GADDS for Win7/XP and Diffrac Plus EVA respectively.

The results are shown in the Table below.

| Salt | Average pH | IDR (mg/min/cm$^2$) Duplicate | Average | XRPD Analysis Post Dissolution |
|---|---|---|---|---|
| Sodium | 4.6 | 38.04, 35.67 | 37 | Not Performed |
| Ethylene Diamine (Example 5) | 4.5 | 0.76, 0.78 | 0.77 | Amorphous |
| Calcium (Example 4) | 4.5 | 0.51, 0.37 | 0.44 | Amorphous |
| Magnesium (Example 4) | 4.5 | 0.47, 0.44 | 0.46 | Amorphous |
| Zinc (Example 4) | 4.5 | 0.19, 0.18 | 0.18 | Amorphous |

Example 7—Intrinsic Dissolution Rate at pH 1.9

Intrinsic Dissolution Rate was Determined in Simulated Intestinal Fluid at pH Base Buffer (FaSSGF):

Sodium chloride (2.0 g) and deionized water added to a 1000 ml volumetric flask, pH adjusted to 1.6 with concentrated hydrochloric FaSSGF acid, made up to volume with deionised water.

FaSSGF Media:

Phares SIF (simulated intestinal fluid) powder (0.06 g) was added to a 1 L volumetric flask and made to volume with base buffer.

Data were collected on a Sirius inform instrument fitted with a dual UV Dip Probe attachment and Ag/AgCl combination pH electrode. The electrode was calibrated using the four plus parameters derived from a blank titration. The base titrant was standardised by titration with TRIS. 0.5 M HCl and NaOH aqueous solutions were used as the acid and base titrants respectively for the testing. Stirring was facilitated by a dual overhead stirrer to allow thorough mixing within the vessel, and media was introduced via a capillary bundle attached to a dispensing bank comprised of six precision dispensing units. A Peltier heating jacket was used to maintain the temperature of the titration vessel. Discs were introduced to the vessel via the tablet picker housed in the probe arm, after the desired temperature of the media had been reached. Sirius inform Assay Design, Control and Refine software were used to design, run and refine data respectively.

Molar Extinction Coefficient (MEC): The reference sample was prepared as a 20.1 mM stock solution in water. One MEC data sets were then collected using five additions each of the water stock using 250, 500 and three times 750 µl aliquots, respectively. UV Spectra were then collected after each addition of the water stock to build a multi-point MEC calibration, using a 20 mm path length probe. The MEC data set was then imported into the dissolution data files in order to convert the UV absorbance measured to concentration. The concentration range for UV data collected was 124.8 µM-1.4 mM. MEC data were collected in the dissolution media {faSSGf} and at 37° C. to match the dissolution experiments.

Intrinsic Dissolution Rate (IDR): Ca. 10-20 mg of the sample was compressed in a 3 mm disc recess, under 100 kg for 2 minutes, with greaseproof paper on the compression base, to form nondisintegrating discs. The discs were then plugged with a bung so that only one surface was exposed to the media during analysis and transferred to the Sirius inform dissolution apparatus. Analysis was performed at 37° C. in 40 ml faSSGf media for 1 hour with UV spectra collected every 30 seconds. A stir speed of 100 rpm was used with a 20 mm path length probe. The IDR was calculated based on the surface area of the 3 mm disc recess used (7.07 mm2 surface area). XRPD analysis was performed on all samples, both after compression of the material into the disc recess, and post dissolution analysis to observe any change in form. All analysis was performed using XRPD 2.

X-Ray Powder Diffraction (XRPD2): XRPD diffractograms were collected on a Bruker AXS C2 GADDS diffractometer using Cu Ka radiation (40 kV, 40 mA), an automated XYZ stage, a laser video microscope for auto sample positioning and a Vantec-500 2-dimensional area detector. X-ray optics consists of a single Gobel multilayer mirror coupled with a pinhole collimator of 0.3 mm. The beam divergence, i.e. the effective size of the X-ray beam on the sample, was approximately 4 mm. A 9-9 continuous scan mode was employed with a sample—detector distance of 20 cm which gives an effective 2θ range of 1.5°-32.5°. The sample was exposed to the X-ray beam for 120 seconds under ambient conditions. The software used for data collection and analysis was GADDS for Win7/XP and Diffrac Plus EVA respectively.

The results are shown in the Table below.

| Salt | Average pH | IDR (mg/min/cm$^2$) Duplicate | Average | XRPD Analysis Post Dissolution |
|---|---|---|---|---|
| Sodium | 1.8 | 41.5, 44.2 | 43 | Not Performed |

| Salt | Average pH | IDR (mg/min/cm$^2$) Duplicate | Average | XRPD Analysis Post Dissolution |
|---|---|---|---|---|
| Ethylene Diamine (Example 5) | 1.6 | 1.16, 1.29 | 1.2 | Amorphous |
| Calcium (Example 4) | 1.8 | 1.15, 1.14 | 1.2 | Amorphous |
| Magnesium (Example 4) | 1.8 | 1.51, 1.67 | 1.6 | Amorphous |
| Zinc (Example 4) | 1.8 | 1.22, 1.31 | 1.3 | Amorphous |

Example 8

A fospropofol calcium salt tablet within a tablet can be prepared as follows. The core tablet contains fospropofol calcium salt (200 mg; 20% by wt. dosage form), microcrystalline cellulose (100 mg; 10% by wt. of dosage form), pregelatinized starch (e.g., Starch 1500)(97.5 mg; 9.75% by weight of dosage form), magnesium stearate (2.5 mg; 0.25% by wt. of dosage form). The outer layer, which surrounds the core tablet, contains fospropofol calcium salt (400 mg; 40% by wt. of dosage form), microcrystalline cellulose (100 mg; 10% wt. of dosage form), pregelatinized starch (e.g., Starch 1500)(97.5 mg; 9.75% by wt. of dosage form), magnesium stearate (2.5 mg; 0.25% by wt. of dosage form). This is a modified-release dosage form. The outer layer dissolves rapidly in the stomach. The core tablet dissolves slowly in the stomach, and further dissolves in the intestines.

Example 9

A fospropofol magnesium salt bilayer tablet can be prepared as follows.

One layer contains fospropofol magnesium salt (200 mg; 20% by wt. of bilayer tablet), microcrystalline cellulose (100 mg; 10% by wt. of bilayer tablet), pregelatinized starch (e.g., Starch 1500)(97.5 mg; 9.75% by wt. of bilayer tablet), magnesium stearate (2.5 mg; 0.25% by wt. of bilayer tablet).

The other layer contains fospropofol magnesium salt (400 mg; 40% by wt. of bilayer tablet), microcrystalline cellulose (100 mg; 10% by wt. of bilayer tablet), pregelatinized starch (e.g., Starch 1500)(97.5 mg; 9.75% by wt. of bilayer tablet), magnesium stearate (2.5 mg; 0.25% by wt. of bilayer tablet).

This is a modified-release dosage form. One layer dissolves rapidly in the stomach. The other layer dissolves slowly in the stomach, and further dissolves in the intestines.

Example 10

A Fospropofol Dosage form with immediate release and delayed release components can be prepared as follows.

The delayed release component contains fospropofol zinc salt (200 mg; 20% by wt. of final dosage form), microcrystalline cellulose (100 mg; 10% by wt. of final dosage form), pregelatinized starch (e.g., Starch 1500)(17.5 mg; 1.75% by wt. of final dosage form), HMPC (80 mg; 8% by wt. of final dosage form), magnesium stearate (2.5 mg; 0.25% by wt. of final dosage form).

The immediate release component contains fospropofol zinc salt (400 mg; 40% by wt. of final dosage form), microcrystalline cellulose (100 mg; 10% by wt. of final dosage form), pregelatinized starch (e.g., Starch 1500)(97.5 mg; 9.75% by wt. of final dosage form), and magnesium stearate (2.5 mg; 0.25% by wt. of final dosage form).

This is a modified-release dosage form. The delayed release component granules and the immediate release component granules may be combined and pressed into a tablet, or may be combined in a capsule.

Example 11

A Fospropofol Dosage form with immediate release and enteric coated components can be prepared as follows.

The enteric coated component contains fospropofol ethylene diamine salt (200 mg; 20% by wt. of final dosage form), microcrystalline cellulose (100 mg; 10% by wt. of final dosage form), pregelatinized starch (e.g., Starch 1500) (47.5 mg; 4.75% by wt. of final dosage form), magnesium stearate (2.5 mg; 0.25% by wt. of final dosage form), Eudragit L (50 mg; 5% by wt. of final dosage form).

The immediate release component contains fospropofol ethylene diamine (400 mg; 40% by wt. of final dosage form), microcrystalline cellulose (100 mg; 10% by wt. of final dosage form), pregelatinized starch (e.g., Starch 1500)(97.5 mg; 9.75% by wt. of final dosage form), and magnesium stearate (2.5 mg; 0.25% by wt. of final dosage form).

This is a modified-release dosage form. The enteric coated component granules and the immediate release component granules or beads may be combined and pressed into a tablet, or may be combined in a capsule.

Example 11

Randomized, double blind, parallel group, comparative evaluation of the safety-tolerability, pharmacokinetics, and efficacy of 3 dosage forms of PO fospropofol salt administered to young healthy male and female volunteers for the acute treatment of moderate or severe migraine headache is conducted as follows.

This study will assess the safety-tolerability, pharmacokinetics, and efficacy (pain relief), in a similar population as in Example 1, of a single administration of one of three dosage forms (the dosage forms of Examples 8, 9, and 10).

The study will also assess the efficacy for relief of associated symptoms (nausea, photophobia, phonophobia) of a single administration of one of three dosage forms (the dosage forms of Examples 8, 9, and 10).

Inclusion criteria: Male and female volunteers, age 18-65 years inclusive with an established diagnosis of migraine, with or without aura, according to IHS criteria. The age at the time of initial migraine diagnosis<50 yo, and the time since initial diagnosis of migraine>one year. The estimated frequency of migraine episodes classified as moderate or severe is at least one per month on average over the past year. Subjects with coexisting headache other than migraine are eligible provided that these headaches are distinguishable from the subject's migraine headaches. No relevant contraindication to use of fospropofol or propofol according to FDA approved labeling. Concomitant medications intended to reduce the frequency of migraine are permitted provided that the dose is stable for at least 3 months prior to enrolment and estimated headache frequency meets the criterion above. If concomitant medications intended to reduce the frequency of migraine are discontinued prior to the study, these medications must be discontinued at least one month prior to enrolment. Patients will also have an absence of any clinically significant medical condition that, in the opinion of the investigator or the Sponsor, may be potentially associated with an increased risk from participation in the study.

Exclusion criteria: Subjects with any medical condition (e.g., sleep apnea) which, in the opinion of the investigator or the Sponsor, may be potentially associated with an increased risk from the administration of study drug. Subjects with a contraindication to use of fospropofol or propofol according to FDA approved labeling. Subjects with any medical condition, which, in the opinion of the investigator or the Sponsor, may be potentially associated with an increased risk from participation in the study. Subjects who require concomitant medications, the use of which, in the opinion of the investigator or the Sponsor, may be potentially associated with an increased risk from participation in the study. Subjects unable or unwilling to provide informed consent. Women of childbearing potential must be on adequate, reliable contraception.

A separate cohort of 36 subjects will be randomized to receive one of 3 regimens (N=12/group) under double-blind conditions, each regimen comprising a single administration of one of the dosage forms of Example 8, 9, or 10. Double-blinding will be preserved by administering an appropriate number of active and placebo capsules for the second dose.

The subject's blood will be sampled pre-dose (within 15 min of dosing) and post-dose: 5, 10, 20, 30, 45, 90 minutes and 2, 4, 6, and 9 hours post-dose. Plasma samples will be assayed for fospropofol and propofol using validated analytical method(s) according to the principles of Good Laboratory Practice.

The following parameters will be calculated with fospropofol and propofol plasma concentrations: AUC0-30 min, AUC0-2 h, AUC0-t, AUC0-inf, Cmax, Residual area, Tmax, T½ el, Kel, Cl/F, Vd/F, and Vd/F/kg.

Subject's will assess headache pain utilizing a 4-point Likert Scale to be assessed at baseline (within 15 min of dosing), and post-dose at 15 min, 30 min, 1 h, 1.5 h, 2 h, 4 h, 6 h, 8 h, 10 h (in clinic) and following discharge (by diary) at 24 h and 48 h post-dosing. Subjects will be asked to record by patient diary any recurrence or worsening of headache pain, and time of onset or worsening. (Note that a qualifying headache must be of at least moderate severity.)

Subjects will assess presence/absence of the most bothersome associated symptom for the presenting headache at baseline (within 15 min of dosing), and post-dose at 15 min, 30 min, 1 h, 1.5 h, 2 h, 4 h, 6 h, 8 h, 10 h (in clinic) and following discharge (by diary) at 24 h and 48 h post-dosing. Subjects will be asked to record by patient diary any recurrence or worsening of the most bothersome symptom, and time of onset or worsening.

Subject's will assess the presence/absence of nausea/vomiting, photophobia, and/or phonophobia at baseline (within 15 min of dosing), and post-dose at 15 min, 30 min, 1 h, 1.5 h, 2 h, 4 h, 6 h, 8 h, 10 h (in clinic) and following discharge (by diary) at 12 h, 24 h and 48 h post-dosing. Subjects will be asked to record by patient diary any recurrence or worsening of the most bothersome symptom, and time of onset or worsening.

Subjects will be instructed to report any adverse events directly to the investigators or clinic staff. Subjects will be instructed to record in the patient diary any adverse events emerging following discharge. All subjects will have telephone access to the investigator or investigator staff to report any urgent concerns in the course of the study.

In order to detect the possible emergence of any clinically significant cardiac arrhythmia or other abnormality cardiac telemetry will be monitored from pre-dose until 10 hours post-dose. Volunteers with any clinically significant ECG abnormality at baseline (pre-dose) will be excluded.

Blood pressure (BP), heart rate (HR), respiratory rate (RR), and pulse oximetry will be recorded within 15 min pre-dose and at approximately 30 min, and 1, 1.5, 2, 2.5, 3, 4, 5, 6, 8, and 10 hours after dosing.

Modified Observer's Assessment of Alertness/Sedation (OAA/S) score within 15 min pre-dose and at approximately 15 min, 30 min, and 1, 1.5, 2, 2.5, 3, 4, 5, 6, 8, and 10 hours after dosing will be assessed.

Hematology, biochemistry, and urinalysis will be assessed at screening and end of study participation.

Alcohol breath test, urine cotinine determination, and urine drug screen will be assessed at check-in.

A physical examination will be conducted at screening and end of study. An abbreviated physical exam will be conducted at clinic check-in.

Subjects will be monitored throughout the study by clinic staff for adverse events. A physician will be on site for each drug administration and until 10 hours post-dose, and available on call for the remainder of the study.

This study will demonstrate that each of the dosage forms of Examples 8, 9, or 10, is safe and effective in treating migraine.

In some embodiments, the disclosure is directed to the following aspects:

Aspect 1. A pharmaceutically acceptable salt of fospropofol, wherein said salt is a potassium, diethylamine, t-butylamine, ethylene diamine, benzathine, piperazine, ethanolamine, diethanolamine, ammonium, tromethamine, benethamine, histidine, calcium, magnesium, or zinc salt.

Aspect 2. The pharmaceutically acceptable salt of fospropofol according to aspect 1, wherein said salt is a potassium salt.

Aspect 3. The potassium salt of aspect 2, wherein said salt is characterized by an X-ray powder diffraction pattern substantially as shown in FIG. 1.

Aspect 4. The potassium salt of aspect 2 or aspect 3, wherein said salt is characterized by an X-ray powder diffraction pattern comprising peaks at 12.3, 17.3, and 20.9 degrees±0.2 degrees 2-theta, on the 2-theta scale with lambda=1.54 angstroms (Cu Kα).

Aspect 5. The potassium salt of any one of aspects 2-4, wherein said salt is characterized by an X-ray powder diffraction pattern comprising peaks at three or more of 12.3, 15.5, 16.2, 16.4, 17.3, 18.0, 18.7, 19.5, 20.0, 20.9, 23.1, 28.1, and 28.7 degrees±0.2 degrees 2-theta, on the 2-theta scale with lambda=1.54 angstroms (Cu Kα).

Aspect 6. The potassium salt of any one of aspects 2-5, wherein said salt is characterized by a differential scanning calorimetry (DSC) thermogram substantially as shown in FIG. 2 when heated at a rate of 10° C./min.

Aspect 7. The potassium salt of any one of aspects 2-6, wherein said salt is characterized by a differential scanning calorimetry (DSC) thermogram comprising an endothermic peak at about 62° C., about 144° C., or about 262° C. when heated at a rate of 10° C./min.

Aspect 8. The pharmaceutically acceptable salt of fospropofol according to aspect 1, wherein said salt is a diethylamine salt.

Aspect 9. The diethylamine salt of aspect 8, wherein said salt is the Form II salt characterized by an X-ray powder diffraction pattern substantially as shown in FIG. 3.

Aspect 10. The diethylamine salt of either aspect 8 or aspect 9, wherein said salt is characterized by an X-ray powder diffraction pattern comprising peaks at 5.8 and 11.0 degrees±0.2 degrees 2-theta, on the 2-theta scale with lambda=1.54 angstroms (Cu Kα).

Aspect 11. The diethylamine salt of any one of aspects 8-10, wherein said salt is characterized by an X-ray powder diffraction pattern comprising peaks at two or more of 5.8, 11.0, 11.5, 14.6, 17.6, 22.0, 23.0, and 24.1 degrees±0.2 degrees 2-theta, on the 2-theta scale with lambda=1.54 angstroms (Cu Kα).

Aspect 12. The diethylamine salt of aspect 8, wherein said salt is the Form I salt characterized by an X-ray powder diffraction pattern substantially as shown in FIG. 4.

Aspect 13. The diethylamine salt of either aspect 8 or aspect 12, wherein said salt is characterized by an X-ray powder diffraction pattern comprising peaks at 10.9 and 11.4 degrees±0.2 degrees 2-theta, on the 2-theta scale with lambda=1.54 angstroms (Cu Kα).

Aspect 14. The diethylamine salt of any one of aspects 8, 12, or 13, wherein said salt is characterized by an X-ray powder diffraction pattern comprising peaks at two or more of 10.9, 11.4, 14.6, 24.2, 25.9, and 27.5 degrees±0.2 degrees 2-theta, on the 2-theta scale with lambda=1.54 angstroms (Cu Kα).

Aspect 15. The diethylamine salt of any one of aspects 8, or 12-14, wherein said salt is characterized by a differential scanning calorimetry (DSC) thermogram substantially as shown in FIG. 5 when heated at a rate of 10° C./min.

Aspect 16. The diethylamine salt of any one of aspects 8, or 12-15, wherein said salt is characterized by a differential scanning calorimetry (DSC) thermogram comprising an endothermic peak at about 98° C. when heated at a rate of 10° C./min.

Aspect 17. The pharmaceutically acceptable salt of fospropofol according to aspect 1, wherein said salt is the t-butylamine salt.

Aspect 18. The t-butylamine salt of aspect 17, wherein said salt is characterized by an X-ray powder diffraction pattern substantially as shown in FIG. 7.

Aspect 19. The t-butylamine salt of either aspect 17 or aspect 18, wherein said salt is characterized by an X-ray powder diffraction pattern comprising peak at 12.2 degrees±0.2 degrees 2-theta, on the 2-theta scale with lambda=1.54 angstroms (Cu Kα).

Aspect 20. The t-butylamine salt of any one of aspects 17-19, wherein said salt is characterized by an X-ray powder diffraction pattern comprising peaks at three or more of 9.0, 9.6, 12.2, 17.1, 19.5, 21.3, 21.7, 23.9, 26.4, 28.3, and 28.8 degrees±0.2 degrees 2-theta, on the 2-theta scale with lambda=1.54 angstroms (Cu Kα).

Aspect 21. The t-butylamine salt of any one of aspects 17-20, wherein said salt is characterized by a differential scanning calorimetry (DSC) thermogram substantially as shown in FIG. 8 when heated at a rate of 10° C./min.

Aspect 22. The t-butylamine salt of any one of aspects 17-21, wherein said salt is characterized by a differential scanning calorimetry (DSC) thermogram comprising an endothermic peak at about 58° C., or at about 195° C. when heated at a rate of 10° C./min.

Aspect 23. The pharmaceutically acceptable salt of fospropofol according to aspect 1, wherein said salt is the ethylene diamine salt.

Aspect 24. The ethylene diamine salt of aspect 23, wherein said salt is characterized by an X-ray powder diffraction pattern substantially as shown in FIG. 10.

Aspect 25. The ethylene diamine salt of either aspect 23 or aspect 24, wherein said salt is characterized by an X-ray powder diffraction pattern comprising peak at 12.6 degrees±0.2 degrees 2-theta, on the 2-theta scale with lambda=1.54 angstroms (Cu Kα).

Aspect 26. The ethylene diamine salt of any one of aspects 23-25, wherein said salt is characterized by an X-ray powder diffraction pattern comprising peaks at three or more of 11.9, 12.6, 13.7, 15.1, 17.8, 20.1, 23.6, and 23.9 degrees±0.2 degrees 2-theta, on the 2-theta scale with lambda=1.54 angstroms (Cu Kα).

Aspect 27. The ethylene diamine salt of any one of aspects 23-26, wherein said salt is characterized by a differential scanning calorimetry (DSC) thermogram substantially as shown in FIG. 11 when heated at a rate of 10° C./min.

Aspect 28. The ethylene diamine salt of any one of aspects 23-27, wherein said salt is characterized by a differential scanning calorimetry (DSC) thermogram comprising an endothermic peak at about 89° C. or at about 192° C. when heated at a rate of 10° C./min.

Aspect 29. The pharmaceutically acceptable salt of fospropofol according to aspect 1, wherein said salt is the benzathine salt.

Aspect 30. The benzathine salt of aspect 29, wherein said salt is characterized by a differential scanning calorimetry (DSC) thermogram substantially as shown in FIG. 13 when heated at a rate of 10° C./min.

Aspect 31. The benzathine salt of either aspect 29 or aspect 30, wherein said salt is characterized by a differential scanning calorimetry (DSC) thermogram comprising an endothermic peak at about 111° C. when heated at a rate of 10° C./min.

Aspect 32. The pharmaceutically acceptable salt of fospropofol according to aspect 1, wherein said salt is the piperazine salt.

Aspect 33. The piperazine salt of aspect 32, wherein said salt is characterized by an x-ray powder diffraction pattern substantially as shown in FIG. 15.

Aspect 34. The piperazine salt of either aspect 32 or aspect 33, wherein said salt is characterized by an X-ray powder diffraction pattern comprising peaks at 4.9, 9.2, and 10.9 degrees±0.2 degrees 2-theta, on the 2-theta scale with lambda=1.54 angstroms (Cu Kα).

Aspect 35. The piperazine salt of any one of aspects 32-34, wherein said salt is characterized by an X-ray powder diffraction pattern comprising peaks at three or more of 4.9, 9.2, 10.9, 13.0, 16.3, 17.4, 20.0, 20.4, 21.3, 21.9, 23.2, and 24.3 degrees±0.2 degrees 2-theta, on the 2-theta scale with lambda=1.54 angstroms (Cu Kα).

Aspect 36. The piperazine salt of any one of aspects 32-35, wherein said salt is characterized by a differential scanning calorimetry (DSC) thermogram substantially as shown in FIG. 16 when heated at a rate of 10° C./min.

Aspect 37. The piperazine salt of any one of aspects 32-36, wherein said salt is characterized by a differential scanning calorimetry (DSC) thermogram comprising an endothermic peak at about 96° C., about 151° C., or about 195° C. when heated at a rate of 10° C./min.

Aspect 38. The pharmaceutically acceptable salt of fospropofol according to aspect 1, wherein said salt is the ethanolamine salt.

Aspect 39. The ethanolamine salt of aspect 38, wherein said salt is the Form II salt characterized by an X-ray powder diffraction pattern substantially as shown in FIG. 18.

Aspect 40. The ethanolamine salt of either aspect 38 or aspect 39, wherein said salt is characterized by an X-ray powder diffraction pattern comprising peaks at 12.5, and 14.2 degrees±0.2 degrees 2-theta, on the 2-theta scale with lambda=1.54 angstroms (Cu Kα).

Aspect 41. The ethanolamine salt of any one of aspects 38-40, wherein said salt is characterized by an X-ray powder diffraction pattern comprising peaks at two or more of 4.8, 12.5, 14.2, 21.9, and 25.1 degrees±0.2 degrees 2-theta, on the 2-theta scale with lambda=1.54 angstroms (Cu Kα).

Aspect 42. The ethanolamine salt of aspect 38, wherein said salt is the Form I salt characterized by an X-ray powder diffraction pattern substantially as shown in FIG. 19.

Aspect 43. The ethanolamine salt of either aspect 38 or aspect 42, wherein said salt is characterized by an X-ray powder diffraction pattern comprising peak at 10.0 degrees±0.2 degrees 2-theta, on the 2-theta scale with lambda=1.54 angstroms (Cu Kα).

Aspect 44. The ethanolamine salt of any one of aspects 38, 42, or 43, wherein said salt is characterized by an X-ray powder diffraction pattern comprising peaks at two or more of 10.0, 15.3, 15.9, 17.0, 18.5, 19.6, and 20.9 degrees±0.2 degrees 2-theta, on the 2-theta scale with lambda=1.54 angstroms (Cu Kα).

Aspect 45. The ethanolamine salt of any one of aspects 38, or 42-44, wherein said salt is characterized by a differential scanning calorimetry (DSC) thermogram substantially as shown in FIG. 20 when heated at a rate of 10° C./min.

Aspect 46. The ethanolamine salt of any one of aspects 38, or 42-45, wherein said salt is characterized by a differential scanning calorimetry (DSC) thermogram comprising an endothermic peak at about 96° C., or about 174° C. when heated at a rate of 10° C./min.

Aspect 47. The pharmaceutically acceptable salt of fospropofol according to aspect 1, wherein said salt is the diethanolamine salt.

Aspect 48. The diethanolamine salt of aspect 47, wherein said salt is characterized by a differential scanning calorimetry (DSC) thermogram substantially as shown in FIG. 22 when heated at a rate of 10° C./min Aspect 49. The diethanolamine salt of either aspect 47 or aspect 48, wherein said salt is characterized by a differential scanning calorimetry (DSC) thermogram comprising an endothermic peak at about 57° C. when heated at a rate of 10° C./min.

Aspect 50. The pharmaceutically acceptable salt of fospropofol according to aspect 1, wherein said salt is the ammonium salt.

Aspect 51. The ammonium salt of aspect 50, wherein said salt is characterized by an x-ray powder diffraction pattern substantially as shown in FIG. 24.

Aspect 52. The ammonium salt of either aspect 50 or aspect 51, wherein said salt is characterized by an X-ray powder diffraction pattern comprising peak at 18.1 degrees±0.2 degrees 2-theta, on the 2-theta scale with lambda=1.54 angstroms (Cu Kα).

Aspect 53. The ammonium salt of any one of aspects 50-52, wherein said salt is characterized by an X-ray powder diffraction pattern comprising peaks at three or more of 12.2, 14.2, 15.9, 18.1, 18.5, 19.2, 21.1, 21.8, and 25.8 degrees±0.2 degrees 2-theta, on the 2-theta scale with lambda=1.54 angstroms (Cu Kα).

Aspect 54. The ammonium salt of any one of aspects 50-53, wherein said salt is characterized by a differential scanning calorimetry (DSC) thermogram substantially as shown in FIG. 25 when heated at a rate of 10° C./min.

Aspect 55. The ammonium salt of any one of aspects 50-54, wherein said salt is characterized by a differential scanning calorimetry (DSC) thermogram comprising an endothermic peak at about 76° C. when heated at a rate of 10° C./min.

Aspect 56. The pharmaceutically acceptable salt of fospropofol according to aspect 1, wherein said salt is the tromethamine salt.

Aspect 57. The tromethamine salt of aspect 56, wherein said salt is characterized by an x-ray powder diffraction pattern substantially as shown in FIG. 26.

Aspect 58. The tromethamine salt of either aspect 56 or aspect 57, wherein said salt is characterized by an X-ray powder diffraction pattern comprising peaks at 10.0, 16.6, and 17.3 degrees±0.2 degrees 2-theta, on the 2-theta scale with lambda=1.54 angstroms (Cu Kα).

Aspect 59. The tromethamine salt of any one of aspects 56-58, wherein said salt is characterized by an X-ray powder diffraction pattern comprising peaks at three or more of 6.0, 10.0, 10.7, 16.6, 17.3, 18.3, 24.7, and 25.2 degrees±0.2 degrees 2-theta, on the 2-theta scale with lambda=1.54 angstroms (Cu Kα).

Aspect 60. The tromethamine salt of any one of aspects 56-59, wherein said salt is characterized by a differential scanning calorimetry (DSC) thermogram substantially as shown in FIG. 27 when heated at a rate of 10° C./min.

Aspect 61. The tromethamine salt of any one of aspects 56-60, wherein said salt is characterized by a differential scanning calorimetry (DSC) thermogram comprising an endothermic peak at about 103° C., about 133° C., or about 171° C. when heated at a rate of 10° C./min.

Aspect 62. The pharmaceutically acceptable salt of fospropofol according to aspect 1, wherein said salt is the benethamine salt.

Aspect 63. The benethamine salt of aspect 62, wherein said salt is characterized by an x-ray powder diffraction pattern substantially as shown in FIG. 29.

Aspect 64. The benethamine salt of either aspect 62 or aspect 63, wherein said salt is characterized by an X-ray powder diffraction pattern comprising peak at 16.4 degrees±0.2 degrees 2-theta, on the 2-theta scale with lambda=1.54 angstroms (Cu Kα).

Aspect 65. The benethamine salt of any one of aspects 62-64, wherein said salt is characterized by an X-ray powder diffraction pattern comprising peaks at three or more of 5.5, 7.2, 8.5, 11.7, 12.6, 16.4, 17.7, and 19.6 degrees±0.2 degrees 2-theta, on the 2-theta scale with lambda=1.54 angstroms (Cu Kα).

Aspect 66. The benethamine salt of any one of aspects 62-65, wherein said salt is characterized by a differential scanning calorimetry (DSC) thermogram substantially as shown in FIG. 30 when heated at a rate of 10° C./min.

Aspect 67. The benethamine salt of any one of aspects 62-66, wherein said salt is characterized by a differential scanning calorimetry (DSC) thermogram comprising an endothermic peak at about 86° C. when heated at a rate of 10° C./min.

Aspect 68. The pharmaceutically acceptable salt of fospropofol according to aspect 1, wherein said salt is the histidine salt.

Aspect 69. The histidine salt of aspect 68, wherein said salt is characterized by an X-ray powder diffraction pattern substantially as shown in FIG. 32.

Aspect 70. The histidine salt of either aspect 68 or aspect 69, wherein said salt is characterized by an X-ray powder diffraction pattern comprising peaks at 11.2, 15.3, and 18.9 degrees±0.2 degrees 2-theta, on the 2-theta scale with lambda=1.54 angstroms (Cu Kα).

Aspect 71. The histidine salt of any one of aspects 68-70, wherein said salt is characterized by an X-ray powder diffraction pattern comprising peaks at three or more of 11.2, 15.3, 18.9, 21.1, 21.5, 24.2, and 30.2 degrees±0.2 degrees 2-theta, on the 2-theta scale with lambda=1.54 angstroms (Cu Kα).

Aspect 72. The histidine salt of any one of aspects 68-71, wherein said salt is characterized by a differential scanning calorimetry (DSC) thermogram substantially as shown in FIG. 33 when heated at a rate of 10° C./min.

Aspect 73. The histidine salt of any one of aspects 68-72, wherein said salt is characterized by a differential scanning calorimetry (DSC) thermogram comprising an endothermic peak at about 196° C. or at about 202° C. when heated at a rate of 10° C./min.

Aspect 74. The pharmaceutically acceptable salt of fospropofol according to aspect 1, wherein said salt is the calcium salt.

Aspect 75. The calcium salt of aspect 74, wherein said salt is the Form I salt characterized by an X-ray powder diffraction pattern substantially as shown in FIG. 35.

Aspect 76. The calcium salt of either aspect 74 or aspect 75, wherein said salt is characterized by an X-ray powder diffraction pattern comprising a peak at 4.7 degrees±0.2 degrees 2-theta, on the 2-theta scale with lambda=1.54 angstroms (Cu Kα).

Aspect 77. The calcium salt of any one of aspects 74-76, wherein said salt is characterized by a DSC thermogram substantially as shown in FIG. 36, or by a TGA profile substantially as shown in FIG. 36.

Aspect 78. The calcium salt of aspect 74, wherein said salt is the Form II salt characterized by an X-ray powder diffraction pattern substantially as shown in FIG. 37.

Aspect 79. The calcium salt of either aspect 74 or aspect 78, wherein said salt is characterized by an X-ray powder diffraction pattern comprising peaks at 5.1, 7.0, 7.7, 8.6, 9.2, and 14.4 degrees±0.2 degrees 2-theta, on the 2-theta scale with lambda=1.54 angstroms (Cu Kα).

Aspect 80. The calcium salt of any one of aspects 74, 78, or 79, wherein said salt is characterized by an X-ray powder diffraction pattern comprising peaks at three or more of 4.3, 4.5, 5.0, 5.1, 7.0, 7.7, 8.6, 9.2, and 14.4 degrees±0.2 degrees 2-theta, on the 2-theta scale with lambda=1.54 angstroms (Cu Kα).

Aspect 81. The calcium salt of aspect 74, wherein said salt is the Form III salt characterized by an X-ray powder diffraction pattern substantially as shown in FIG. 38.

Aspect 82. The calcium salt of either aspect 74 or aspect 81, wherein said salt is characterized by an X-ray powder diffraction pattern comprising peaks at 4.8, and 9.7 degrees±0.2 degrees 2-theta, on the 2-theta scale with lambda=1.54 angstroms (Cu Kα).

Aspect 83. The calcium salt of any one of aspects 74, 81, or 82, wherein said salt is characterized by an X-ray powder diffraction pattern comprising peaks at three or more of 4.8, 9.7, 11.6, 11.9, 14.5, 17.2, and 29.1 degrees±0.2 degrees 2-theta, on the 2-theta scale with lambda=1.54 angstroms (Cu Kα).

Aspect 84. The pharmaceutically acceptable salt of fospropofol according to aspect 1, wherein said salt is the magnesium salt.

Aspect 85. The magnesium salt of aspect 84, wherein said salt is characterized by an X-ray powder diffraction pattern substantially as shown in FIG. 39.

Aspect 86. The magnesium salt of either aspect 84 or aspect 85, wherein said salt is characterized by an X-ray powder diffraction pattern comprising a peak at 4.5 degrees±0.2 degrees 2-theta, on the 2-theta scale with lambda=1.54 angstroms (Cu Kα).

Aspect 87. The magnesium salt of any one of aspects 84-86, wherein said salt is characterized by an X-ray powder diffraction pattern comprising peaks at two or more of 4.5, 9.1, 13.6, 20.8, and 27.9 degrees±0.2 degrees 2-theta, on the 2-theta scale with lambda=1.54 angstroms (Cu Kα).

Aspect 88. The magnesium salt of any one of aspects 84-87, wherein said salt is characterized by a DSC thermogram substantially as shown in FIG. 40, or by a TGA profile substantially as shown in FIG. 40.

Aspect 89. The magnesium salt of any one of aspects 84-88, wherein said salt is characterized by a differential scanning calorimetry (DSC) thermogram comprising an endothermic peak at about 129° C. when heated at a rate of 10° C./min.

Aspect 90. The pharmaceutically acceptable salt of fospropofol according to aspect 1, wherein said salt is the zinc salt.

Aspect 91. The zinc salt of aspect 90, wherein said salt is the Form II salt characterized by an X-ray powder diffraction pattern substantially as shown in FIG. 41.

Aspect 92. The zinc salt of either aspect 90 or aspect 91, wherein said salt is characterized by an X-ray powder diffraction pattern comprising a peak at 4.9 degrees±0.2 degrees 2-theta, on the 2-theta scale with lambda=1.54 angstroms (Cu Kα).

Aspect 93. The zinc salt of aspect 90, wherein said salt is the Form I salt characterized by an X-ray powder diffraction pattern substantially as shown in FIG. 42.

Aspect 94. The zinc salt of either aspect 90 or aspect 93, wherein said salt is characterized by an X-ray powder diffraction pattern comprising peaks at 8.1, 9.6, and 10.3 degrees±0.2 degrees 2-theta, on the 2-theta scale with lambda=1.54 angstroms (Cu Kα).

Aspect 95. The zinc salt of any one of aspects 90, 93, or 94, wherein said salt is characterized by an X-ray powder diffraction pattern comprising peaks at three or more of 5.1, 8.1, 9.6, 10.3, 11.6, 12.2, 18.2, 18.6, and 26.3 degrees±0.2 degrees 2-theta, on the 2-theta scale with lambda=1.54 angstroms (Cu Kα).

Aspect 96. The zinc salt of any one of aspects 90, or 93-95, wherein said salt is characterized by a DSC thermogram substantially as shown in FIG. 43, or by a TGA profile substantially as shown in FIG. 43.

Aspect 97. The zinc salt of any one of aspects 90, or 93-96, wherein said salt is characterized by a differential scanning calorimetry (DSC) thermogram comprising an endothermic peak at about 114° C. or about 210° C. when heated at a rate of 10° C./min.

Aspect 98. A pharmaceutical composition comprising the fospropofol salt according to any one of aspects 1-97, and a pharmaceutically acceptable excipient.

Aspect 99. A method of treating migraine in a patient in need thereof, comprising administering to said patient an effective amount of the fospropofol salt according to any one of aspects 1-97.

Aspect 100. The method of aspect 99 wherein said patient's migraine is refractory migraine.

Aspect 101. The method of any one of aspects 99 or 100, wherein said effective amount of fospropofol salt is administered orally, perorally, subcutaneously, intramuscularly, intravenously, transmucosally, sublingually, buccally, transdermally, intraintestinally, rectally, or intrapulmonarily.

The invention claimed is:

1. A method of treating migraine in a patient in need thereof, comprising administering to the patient a pharmaceutical composition comprising an effective amount of a fospropofol salt, wherein the fospropofol salt is:
   a potassium salt characterized by an X-ray powder diffraction pattern comprising peaks at 12.3, 17.3, and 20.9 degrees±0.2 degrees 2-theta, on the 2-theta scale with lambda=1.54 angstroms (Cu Kα).

2. The method of claim 1 wherein the patient's migraine is refractory migraine.

3. The method of claim 1, wherein the effective amount of fospropofol salt is administered orally, perorally, subcutaneously, intramuscularly, intravenously, transmucosally, sublingually, buccally, transdermally, intraintestinally, rectally, or intrapulmonarily.

* * * * *